United States Patent [19]
Lemke et al.

[11] Patent Number: 5,837,448
[45] Date of Patent: Nov. 17, 1998

[54] PROTEIN-TYROSINE KINASE GENES

[75] Inventors: Greg E. Lemke, Del Mar; Cary H. C. Lai, La Jolla, both of Calif.

[73] Assignee: The Salk Institute for Biological Studies, La Jolla, Calif.

[21] Appl. No.: 237,401

[22] Filed: May 2, 1994

Related U.S. Application Data

[63] Continuation of Ser. No. 884,486, May 15, 1992, abandoned.

[51] Int. Cl.$^6$ .............................. C12Q 1/68; C07H 21/04
[52] U.S. Cl. ........................... 435/6; 435/252.3; 435/325; 435/320.1; 435/352; 536/23.5; 536/24.31; 536/24.33; 935/9; 935/11; 935/22; 935/78
[58] Field of Search ....................... 435/6, 172.3, 240.1, 435/240.2, 252.3, 320.1, 325, 352; 536/23.5, 24.31, 24.33, 25.4; 935/9, 11, 22, 78

[56] References Cited

U.S. PATENT DOCUMENTS 5,468,634  11/1995  Liu ........................................ 435/240.2

OTHER PUBLICATIONS

Stark et al. Development (Oct. 1991) 113 641–651.
Nada et al. Nature (2 May 1991) 391: 69–72.
Wilks et al. Gene (1989) 85: 67–74.
Raz et al. Oncogene (May 1991) 6: 753–760.
Rescigno, J. et al Oncogene (Oct. 1991) 6: 1909–13.
Sajjadi et al. New Biol. (Aug. 1991) 3: 769–78.
Gordon et al Proc. Natl Acad Sci. USA (1980) 77:7380.
Lai et al., An Extended Family of Protein–Tyrosine Kinase Genes Differentially Expressed in the Vertebrate Nervous System, Neuron, vol. 6, 691–704, May 1991.
Witte, Steel Locus Defines New Multipotent Growth Factor, Cell, vol. 63, 5–6, Oct. 5, 1990.
Basler et al., Control of Photoreceptor Cell Fate by the sevenless Protein Requires a Functional Tyrosine Kinase Domain, Cell, vol. 54, 299–31, Jul. 29, 1988.
Lindberg et al., cDNA Cloning and Characterization of eck, an Epithelial Cell Receptor . . . , Molecular and Cellular Biology, Dec. 1990, pp. 6316–6324.
Rubin, Development of the Drosophila Retina: Inductive Events Studied at Single Cell Resolution, Cell, vol. 57, 519–520, May 19, 1989.
Partanen, et al., Putative tyrosine kinases expressed in K–562 human leukemia cells, Proc. Natl. Acad. Sci. USA, vol. 87, pp. 8913–8917, Nov. 1990.
Hunter et al., Protein–Tyrosine Kinases and Their Substrates, Protein Design and the Development of New Therapeutics and Vaccines, Chap. 6, pp. 119–139.
Klein, et al., trkB, a novel tyrosine protein kinase receptor expressed during mouse neural development; The EMBO Journal, vol. 8, pp. 3701–3709, 1989.
Bargmann, et al., The neu oncogene encodes an epidermal growth factor receptor related protein, Nature, vol. 319, Jan. 16, 1986.
Janssen et al., A novel putative tyrosine kinase receptor with oncogenic potential, Oncogene (1991) 6, 2113–2120.
Letwin, et al., Novel protein–tyrosine kinase cDNAs related to fps/fes and epn cloned using anti–phosphotyrosine antibody, Oncogene (1988), 3, 621–627.
O'Bryan et al., axl, a Transforming Gene Isolated from Primary Human Myeloid Leukemia Cells . . . , Molecular and Cellular Biology, Oct. 1991, pp. 5016–5031.

*Primary Examiner*—Carla J. Myers
*Attorney, Agent, or Firm*—Fish & Richardson, P.C.

[57] ABSTRACT

The invention provides pure receptor protein tyrosine kinase (PTK) subtypes, tyro-1–8 and tyro-10–12, polynucleotides encoding these PTK subtypes and the use of oligonucleotides which align with the flanking regions of the receptor PTK subtypes, thereby allowing amplification of the polynucleotides encoding the receptor PTK subtype.

10 Claims, 3 Drawing Sheets

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
        ( A ) LENGTH: 165 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-1

( i x ) FEATURE:
        ( A ) NAME/KEY: CDS
        ( B ) LOCATION: 1..165

( x i ) SEQUENCE DESCRIPTION: SEQ ID NO:1:

```
AAC  ATT  CTG  GTA  AAC  AGC  AAC  TTG  GTC  TGC  AAG  GTG  TCT  GAT  TTC  GGC        48
Asn  Ile  Leu  Val  Asn  Ser  Asn  Leu  Val  Cys  Lys  Val  Ser  Asp  Phe  Gly
 1                   5                        10                      15

ATG  TCC  AGG  GTG  CTT  GAG  GAT  GAC  CCG  GAA  GCA  GCC  TAT  ACT  ACC  AGG        96
Met  Ser  Arg  Val  Leu  Glu  Asp  Asp  Pro  Glu  Ala  Ala  Tyr  Thr  Thr  Arg
                20                       25                       30

GGC  GGC  AAG  ATT  CCC  ATC  CGG  TGG  ACT  GCA  CCA  GAA  GCA  ATT  GCG  TAT       144
Gly  Gly  Lys  Ile  Pro  Ile  Arg  Trp  Thr  Ala  Pro  Glu  Ala  Ile  Ala  Tyr
           35                       40                       45

CGT  AAA  TTT  ACC  TCA  GCC  AGT                                                    165
Arg  Lys  Phe  Thr  Ser  Ala  Ser
 50                      55
```

( 2 ) INFORMATION FOR SEQ ID NO:2:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Asn Ile Leu Val Asn Ser Asn Leu Val Cys Lys Val Ser Asp Phe Gly
 1               5                  10                  15

Met Ser Arg Val Leu Glu Asp Asp Pro Glu Ala Ala Tyr Thr Thr Arg
                20                  25                  30

Gly Gly Lys Ile Pro Ile Arg Trp Thr Ala Pro Glu Ala Ile Ala Tyr
            35                  40                  45

Arg Lys Phe Thr Ser Ala Ser
            50              55
```

( 2 ) INFORMATION FOR SEQ ID NO:3:

( i ) SEQUENCE CHARACTERISTICS:
        ( A ) LENGTH: 2437 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-2

( i x ) FEATURE:
        ( A ) NAME/KEY: CDS
        ( B ) LOCATION: 3..2118

( x i ) SEQUENCE DESCRIPTION: SEQ ID NO:3:

```
CA  AAC TGT GTG GAG AAA TGT CCA GAT GGC CTA CAG GGA GCA AAC AGT        47
    Asn Cys Val Glu Lys Cys Pro Asp Gly Leu Gln Gly Ala Asn Ser
     1               5                  10                  15

TTC ATT TTT AAG TAT GCA GAT CAG GAT CGG GAG TGC CAC CCT TGC CAT        95
Phe Ile Phe Lys Tyr Ala Asp Gln Asp Arg Glu Cys His Pro Cys His
                20                  25                  30

CCA AAC TGC ACC CAG GGG TGT AAC GGT CCC ACT AGT CAT GAC TGC ATT       143
Pro Asn Cys Thr Gln Gly Cys Asn Gly Pro Thr Ser His Asp Cys Ile
            35                  40                  45

TAC TAC CCA TGG ACG GGC CAT TCC ACT TTA CCA CAA CAC GCT AGA ACT       191
Tyr Tyr Pro Trp Thr Gly His Ser Thr Leu Pro Gln His Ala Arg Thr
        50                  55                  60

CCA CTG ATT GCA GCC GGA GTC ATT GGA GGC CTC TTC ATC CTG GTG ATC       239
Pro Leu Ile Ala Ala Gly Val Ile Gly Gly Leu Phe Ile Leu Val Ile
    65                  70                  75

ATG GCT TTG ACA TTT GCT GTC TAT GTC AGA AGA AAG AGC ATC AAA AAG       287
Met Ala Leu Thr Phe Ala Val Tyr Val Arg Arg Lys Ser Ile Lys Lys
 80                  85                  90                  95

AAA CGT GCT TTG AGG AGA TTC CTG GAG ACA GAG CTG GTA GAG CCC TTA       335
Lys Arg Ala Leu Arg Arg Phe Leu Glu Thr Glu Leu Val Glu Pro Leu
                100                 105                 110

ACT CCC AGT GGC ACG GCA CCC AAT CAA GCT CAA CTT CGC ATT TTG AAG       383
Thr Pro Ser Gly Thr Ala Pro Asn Gln Ala Gln Leu Arg Ile Leu Lys
            115                 120                 125

GAA ACC GAA CTA AAG AGG GTA AAG GTC CTT GGC TCG GGA GCT TTT GGA       431
Glu Thr Glu Leu Lys Arg Val Lys Val Leu Gly Ser Gly Ala Phe Gly
        130                 135                 140
```

| | | | | | | | | | | | | | | | | |
|---|---|---|---|---|---|---|---|---|---|---|---|---|---|---|---|---|
| ACC | GTT | TAT | AAA | GGT | ATT | TGG | GTG | CCT | GAA | GGT | GAA | ACA | GTG | AAA | ATC | 479 |
| Thr | Val | Tyr | Lys | Gly | Ile | Trp | Val | Pro | Glu | Gly | Glu | Thr | Val | Lys | Ile | |
| | | 145 | | | | 150 | | | | | 155 | | | | | |
| CCT | GTG | GCT | ATA | AAG | ATC | CTC | AAT | GAA | ACA | ACT | GGC | CCC | AAA | GCC | AAC | 527 |
| Pro | Val | Ala | Ile | Lys | Ile | Leu | Asn | Glu | Thr | Thr | Gly | Pro | Lys | Ala | Asn | |
| 160 | | | | | 165 | | | | | 170 | | | | | 175 | |
| GTG | GAG | TTC | ATG | GAT | GAG | GCT | CTG | ATC | ATG | GCA | AGT | ATG | GAT | CAC | CCA | 575 |
| Val | Glu | Phe | Met | Asp | Glu | Ala | Leu | Ile | Met | Ala | Ser | Met | Asp | His | Pro | |
| | | | | 180 | | | | | 185 | | | | | 190 | | |
| CAC | CTA | GTT | CGC | CTA | TTG | GGA | GTG | TGT | CTG | AGT | CCC | ACT | ATC | CAG | TTG | 623 |
| His | Leu | Val | Arg | Leu | Leu | Gly | Val | Cys | Leu | Ser | Pro | Thr | Ile | Gln | Leu | |
| | | | 195 | | | | | 200 | | | | | 205 | | | |
| GTT | ACG | CAG | CTG | ATG | CCG | CAT | GCG | TGC | CTA | CTG | GAC | TAT | GTT | CAT | GAA | 671 |
| Val | Thr | Gln | Leu | Met | Pro | His | Ala | Cys | Leu | Leu | Asp | Tyr | Val | His | Glu | |
| | | 210 | | | | | 215 | | | | | 220 | | | | |
| CAC | AAG | GAT | AAC | ATT | GGA | TCA | CAG | CTG | CTG | TTG | AAC | TGG | TGT | GTC | CAG | 719 |
| His | Lys | Asp | Asn | Ile | Gly | Ser | Gln | Leu | Leu | Leu | Asn | Trp | Cys | Val | Gln | |
| | 225 | | | | | 230 | | | | | 235 | | | | | |
| ATT | GCT | AAG | GGA | ATG | ATG | TAC | CTA | GAA | GAA | AGA | CGG | CTT | GTT | CAT | CGG | 767 |
| Ile | Ala | Lys | Gly | Met | Met | Tyr | Leu | Glu | Glu | Arg | Arg | Leu | Val | His | Arg | |
| 240 | | | | | 245 | | | | | 250 | | | | | 255 | |
| GAT | CTG | GCA | GCC | CGC | AAT | GTC | TTA | GTG | AAA | TCT | CCA | AAT | CAT | GTT | AAA | 815 |
| Asp | Leu | Ala | Ala | Arg | Asn | Val | Leu | Val | Lys | Ser | Pro | Asn | His | Val | Lys | |
| | | | | 260 | | | | | 265 | | | | | 270 | | |
| ATC | ACA | GAT | TTT | GGA | CTG | GCC | CGG | CTC | TTG | GAA | GGA | GAT | GAA | AAA | GAA | 863 |
| Ile | Thr | Asp | Phe | Gly | Leu | Ala | Arg | Leu | Leu | Glu | Gly | Asp | Glu | Lys | Glu | |
| | | | 275 | | | | | 280 | | | | | 285 | | | |
| TAC | AAT | GCT | GAT | GGT | GGC | AAG | ATG | CCA | ATT | AAA | TGG | ATG | GCT | CTG | GAA | 911 |
| Tyr | Asn | Ala | Asp | Gly | Gly | Lys | Met | Pro | Ile | Lys | Trp | Met | Ala | Leu | Glu | |
| | | 290 | | | | | 295 | | | | | 300 | | | | |
| TGT | ATA | CAT | TAT | AGG | AAA | TTC | ACA | CAT | CAA | AGT | GAT | GTT | TGG | AGC | TAT | 959 |
| Cys | Ile | His | Tyr | Arg | Lys | Phe | Thr | His | Gln | Ser | Asp | Val | Trp | Ser | Tyr | |
| | 305 | | | | | 310 | | | | | 315 | | | | | |
| GGC | GTC | ACT | ATA | TGG | GAA | CTG | ATG | ACC | TTT | GGA | GGA | AAG | CCC | TAT | GAT | 1007 |
| Gly | Val | Thr | Ile | Trp | Glu | Leu | Met | Thr | Phe | Gly | Gly | Lys | Pro | Tyr | Asp | |
| 320 | | | | | 325 | | | | | 330 | | | | | 335 | |
| GGA | ATT | CCA | ACC | CGA | GAA | ATC | CCC | GAT | TTA | CTG | GAG | AAA | GGA | GAG | CGT | 1055 |
| Gly | Ile | Pro | Thr | Arg | Glu | Ile | Pro | Asp | Leu | Leu | Glu | Lys | Gly | Glu | Arg | |
| | | | | 340 | | | | | 345 | | | | | 350 | | |
| CTG | CCT | CAG | CCT | CCC | ATC | TGC | ACT | ATT | GAT | GTT | TAC | ATG | GTC | ATG | GTC | 1103 |
| Leu | Pro | Gln | Pro | Pro | Ile | Cys | Thr | Ile | Asp | Val | Tyr | Met | Val | Met | Val | |
| | | | 355 | | | | | 360 | | | | | 365 | | | |
| AAA | TGT | TGG | ATG | ATC | GAT | GCT | GAC | AGC | AGA | CCT | AAA | TTC | AAA | GAA | CTG | 1151 |
| Lys | Cys | Trp | Met | Ile | Asp | Ala | Asp | Ser | Arg | Pro | Lys | Phe | Lys | Glu | Leu | |
| | | 370 | | | | | 375 | | | | | 380 | | | | |
| GCT | GCT | GAG | TTT | TCA | AGA | ATG | GCT | AGA | GAC | CCT | CAA | AGA | TAC | CTA | GTT | 1199 |
| Ala | Ala | Glu | Phe | Ser | Arg | Met | Ala | Arg | Asp | Pro | Gln | Arg | Tyr | Leu | Val | |
| | 385 | | | | | 390 | | | | | 395 | | | | | |
| ATT | CAG | GGT | GAT | GAT | CGT | ATG | AAG | CTT | CCC | AGT | CCA | AAT | GAC | AGC | AAA | 1247 |
| Ile | Gln | Gly | Asp | Asp | Arg | Met | Lys | Leu | Pro | Ser | Pro | Asn | Asp | Ser | Lys | |
| 400 | | | | | 405 | | | | | 410 | | | | | 415 | |
| TTC | TTC | CAG | AAT | CTC | TTG | GAT | GAA | GAG | GAT | TTG | GAA | GAC | ATG | ATG | GAT | 1295 |
| Phe | Phe | Gln | Asn | Leu | Leu | Asp | Glu | Glu | Asp | Leu | Glu | Asp | Met | Met | Asp | |
| | | | | 420 | | | | | 425 | | | | | 430 | | |
| GCT | GAG | GAA | TAT | TTG | GTC | CCC | CAG | GCT | TTC | AAC | ATA | CCT | CCT | CCC | ATC | 1343 |
| Ala | Glu | Glu | Tyr | Leu | Val | Pro | Gln | Ala | Phe | Asn | Ile | Pro | Pro | Pro | Ile | |
| | | | 435 | | | | | 440 | | | | | 445 | | | |
| TAC | ACA | TCC | AGA | ACA | AGA | ATT | GAC | TCC | AAT | AGG | AAT | CAG | TTT | GTG | TAC | 1391 |
| Tyr | Thr | Ser | Arg | Thr | Arg | Ile | Asp | Ser | Asn | Arg | Asn | Gln | Phe | Val | Tyr | |
| | | 450 | | | | | 455 | | | | | 460 | | | | |

```
CAA GAT GGG GGC TTT GCT ACA CAA CAA GGA ATG CCC ATG CCC TAC AGA      1439
Gln Asp Gly Gly Phe Ala Thr Gln Gln Gly Met Pro Met Pro Tyr Arg
465                         470                 475

GCC ACA ACC AGC ACC ATA CCA GAG GCT CCA GTA GCT CAG GGT GCA ACG      1487
Ala Thr Thr Ser Thr Ile Pro Glu Ala Pro Val Ala Gln Gly Ala Thr
480                     485                 490                 495

GCT GAG ATG TTT GAT GAC TCC TGC TGT AAT GGT ACC CTA CGA AAG CCA      1535
Ala Glu Met Phe Asp Asp Ser Cys Cys Asn Gly Thr Leu Arg Lys Pro
                    500                 505                 510

GTG GCA CCC CAT GTC CAA GAG GAC AGT AGC ACT CAG AGG TAT AGT GCT      1583
Val Ala Pro His Val Gln Glu Asp Ser Ser Thr Gln Arg Tyr Ser Ala
                515                 520                 525

GAT CCC ACA GTG TTC GCC CCA GAA CGG AAT CCT CGA GGA GAA CTG GAT      1631
Asp Pro Thr Val Phe Ala Pro Glu Arg Asn Pro Arg Gly Glu Leu Asp
            530                 535                 540

GAA GAA GGC TAC ATG ACT CCA ATG CAT GAC AAG CCC AAA CAA GAA TAT      1679
Glu Glu Gly Tyr Met Thr Pro Met His Asp Lys Pro Lys Gln Glu Tyr
545                 550                 555

CTG AAT CCT GTG GAA GAG AAC CCT TTT GTG TCC CGA AGG AAG AAT GGA      1727
Leu Asn Pro Val Glu Glu Asn Pro Phe Val Ser Arg Arg Lys Asn Gly
560                 565                 570                 575

GAT CTT CAA GCT TTA GAT AAT CCG GAG TAT CAC AGT GCT TCC AGC GGT      1775
Asp Leu Gln Ala Leu Asp Asn Pro Glu Tyr His Ser Ala Ser Ser Gly
                580                 585                 590

CCA CCC AAG GCG GAG GAT GAA TAC GTG AAT GAG CCT CTA TAC CTC AAC      1823
Pro Pro Lys Ala Glu Asp Glu Tyr Val Asn Glu Pro Leu Tyr Leu Asn
            595                 600                 605

ACC TTC GCC AAT GCC TTG GGG AGT GCA GAG TAC ATG AAA AAC AGT GTA      1871
Thr Phe Ala Asn Ala Leu Gly Ser Ala Glu Tyr Met Lys Asn Ser Val
        610                 615                 620

CTG TCT GTG CCA GAG AAA GCC AAG AAA GCA TTT GAC AAC CCC GAC TAC      1919
Leu Ser Val Pro Glu Lys Ala Lys Lys Ala Phe Asp Asn Pro Asp Tyr
625                 630                 635

TGG AAC CAC AGC CTG CCA CCC CGG AGC ACC CTT CAG CAC CCA GAC TAC      1967
Trp Asn His Ser Leu Pro Pro Arg Ser Thr Leu Gln His Pro Asp Tyr
640                 645                 650                 655

CTG CAG GAA TAC AGC ACA AAA TAT TTT TAT AAA CAG AAT GGA CGG ATC      2015
Leu Gln Glu Tyr Ser Thr Lys Tyr Phe Tyr Lys Gln Asn Gly Arg Ile
                660                 665                 670

CGC CCC ATT GTG GCA GAG AAT CCT GAG TAC CTC TCG GAG TTC TCG CTG      2063
Arg Pro Ile Val Ala Glu Asn Pro Glu Tyr Leu Ser Glu Phe Ser Leu
            675                 680                 685

AAG CCT GGC ACT ATG CTG CCC CCT CCG CCC TAC AGA CAC CGG AAT ACT      2111
Lys Pro Gly Thr Met Leu Pro Pro Pro Pro Tyr Arg His Arg Asn Thr
                690                 695                 700

GTG GTG T GAGCTTGGCT AGAGTGTTAG GTGGAGAAAC ACACACCCAC TCCATTTCCC     2168
Val Val
705

TTCCCCCTCC TCTTTCTCTG GTGGTCTTCC TTCTTCTCCC AAGGCCAGTA GTTTTGACAC    2228

TTCCAAGTGG AAGCAGTAGA GATGCAATGA TAGTTCTGTG CTTACCTAAC TTGAATATTA    2288

GAAGGAAAGA CTGAAAGAGA AGACAGGGA TACACACACT GTTTCTTCGT TTCTTCATAT     2348

GGGTTGGTTA ACAGAGTGTC AAAGCTAGAG AAGGTCTAGG AAGTATAAGG CAATACTGCC    2408

TGCTGTCAAA GAGCCCCATC TTTCTTCTC                                      2437
```

( 2 ) INFORMATION FOR SEQ ID NO:4:

( i ) SEQUENCE CHARACTERISTICS:
      ( A ) LENGTH: 705 amino acids (B) TYPE: amino acid
(D) TOPOLOGY: linear (ii) MOLECULE TYPE: protein (xi) SEQUENCE DESCRIPTION: SEQ ID NO:4:

| Asn | Cys | Val | Glu | Lys | Cys | Pro | Asp | Gly | Leu | Gln | Gly | Ala | Asn | Ser | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ile | Phe | Lys | Tyr | Ala | Asp | Gln | Asp | Arg | Glu | Cys | His | Pro | Cys | His | Pro |
|     |     |     | 20  |     |     |     |     | 25  |     |     |     |     | 30  |     |     |
| Asn | Cys | Thr | Gln | Gly | Cys | Asn | Gly | Pro | Thr | Ser | His | Asp | Cys | Ile | Tyr |
|     |     | 35  |     |     |     |     | 40  |     |     |     |     | 45  |     |     |     |
| Tyr | Pro | Trp | Thr | Gly | His | Ser | Thr | Leu | Pro | Gln | His | Ala | Arg | Thr | Pro |
|     | 50  |     |     |     |     | 55  |     |     |     |     | 60  |     |     |     |     |
| Leu | Ile | Ala | Ala | Gly | Val | Ile | Gly | Gly | Leu | Phe | Ile | Leu | Val | Ile | Met |
| 65  |     |     |     |     | 70  |     |     |     |     | 75  |     |     |     |     | 80  |
| Ala | Leu | Thr | Phe | Ala | Val | Tyr | Val | Arg | Arg | Lys | Ser | Ile | Lys | Lys | Lys |
|     |     |     |     | 85  |     |     |     |     | 90  |     |     |     |     | 95  |     |
| Arg | Ala | Leu | Arg | Arg | Phe | Leu | Glu | Thr | Glu | Leu | Val | Glu | Pro | Leu | Thr |
|     |     |     |     | 100 |     |     |     |     | 105 |     |     |     |     | 110 |     |
| Pro | Ser | Gly | Thr | Ala | Pro | Asn | Gln | Ala | Gln | Leu | Arg | Ile | Leu | Lys | Glu |
|     |     |     | 115 |     |     |     |     | 120 |     |     |     |     | 125 |     |     |
| Thr | Glu | Leu | Lys | Arg | Val | Lys | Val | Leu | Gly | Ser | Gly | Ala | Phe | Gly | Thr |
|     |     | 130 |     |     |     |     | 135 |     |     |     |     | 140 |     |     |     |
| Val | Tyr | Lys | Gly | Ile | Trp | Val | Pro | Glu | Gly | Glu | Thr | Val | Lys | Ile | Pro |
| 145 |     |     |     |     | 150 |     |     |     |     | 155 |     |     |     |     | 160 |
| Val | Ala | Ile | Lys | Ile | Leu | Asn | Glu | Thr | Thr | Gly | Pro | Lys | Ala | Asn | Val |
|     |     |     |     | 165 |     |     |     |     | 170 |     |     |     |     | 175 |     |
| Glu | Phe | Met | Asp | Glu | Ala | Leu | Ile | Met | Ala | Ser | Met | Asp | His | Pro | His |
|     |     |     | 180 |     |     |     |     | 185 |     |     |     |     | 190 |     |     |
| Leu | Val | Arg | Leu | Leu | Gly | Val | Cys | Leu | Ser | Pro | Thr | Ile | Gln | Leu | Val |
|     |     | 195 |     |     |     |     | 200 |     |     |     |     | 205 |     |     |     |
| Thr | Gln | Leu | Met | Pro | His | Ala | Cys | Leu | Leu | Asp | Tyr | Val | His | Glu | His |
|     | 210 |     |     |     |     | 215 |     |     |     |     | 220 |     |     |     |     |
| Lys | Asp | Asn | Ile | Gly | Ser | Gln | Leu | Leu | Leu | Asn | Trp | Cys | Val | Gln | Ile |
| 225 |     |     |     |     | 230 |     |     |     |     | 235 |     |     |     |     | 240 |
| Ala | Lys | Gly | Met | Met | Tyr | Leu | Glu | Glu | Arg | Arg | Leu | Val | His | Arg | Asp |
|     |     |     |     | 245 |     |     |     |     | 250 |     |     |     |     | 255 |     |
| Leu | Ala | Ala | Arg | Asn | Val | Leu | Val | Lys | Ser | Pro | Asn | His | Val | Lys | Ile |
|     |     |     | 260 |     |     |     |     | 265 |     |     |     |     | 270 |     |     |
| Thr | Asp | Phe | Gly | Leu | Ala | Arg | Leu | Leu | Glu | Gly | Asp | Glu | Lys | Glu | Tyr |
|     |     | 275 |     |     |     |     | 280 |     |     |     |     | 285 |     |     |     |
| Asn | Ala | Asp | Gly | Gly | Lys | Met | Pro | Ile | Lys | Trp | Met | Ala | Leu | Glu | Cys |
|     | 290 |     |     |     |     | 295 |     |     |     |     | 300 |     |     |     |     |
| Ile | His | Tyr | Arg | Lys | Phe | Thr | His | Gln | Ser | Asp | Val | Trp | Ser | Tyr | Gly |
| 305 |     |     |     |     | 310 |     |     |     |     | 315 |     |     |     |     | 320 |
| Val | Thr | Ile | Trp | Glu | Leu | Met | Thr | Phe | Gly | Gly | Lys | Pro | Tyr | Asp | Gly |
|     |     |     |     | 325 |     |     |     |     | 330 |     |     |     |     | 335 |     |
| Ile | Pro | Thr | Arg | Glu | Ile | Pro | Asp | Leu | Leu | Glu | Lys | Gly | Glu | Arg | Leu |
|     |     |     | 340 |     |     |     |     | 345 |     |     |     |     | 350 |     |     |
| Pro | Gln | Pro | Pro | Ile | Cys | Thr | Ile | Asp | Val | Tyr | Met | Val | Met | Val | Lys |
|     |     | 355 |     |     |     |     | 360 |     |     |     |     | 365 |     |     |     |
| Cys | Trp | Met | Ile | Asp | Ala | Asp | Ser | Arg | Pro | Lys | Phe | Lys | Glu | Leu | Ala |
|     | 370 |     |     |     |     | 375 |     |     |     |     | 380 |     |     |     |     |
| Ala | Glu | Phe | Ser | Arg | Met | Ala | Arg | Asp | Pro | Gln | Arg | Tyr | Leu | Val | Ile |

|  | 385 |  |  |  |  | 390 |  |  |  |  | 395 |  |  |  |  | 400 |
|---|---|---|---|---|---|---|---|---|---|---|---|---|---|---|---|---|
| Gln | Gly | Asp | Asp | Arg<br>405 | Met | Lys | Leu | Pro | Ser<br>410 | Pro | Asn | Asp | Ser | Lys<br>415 | Phe |
| Phe | Gln | Asn | Leu<br>420 | Leu | Asp | Glu | Glu<br>425 | Leu | Glu | Asp | Met | Met<br>430 | Asp | Ala |
| Glu | Glu | Tyr<br>435 | Leu | Val | Pro | Gln<br>440 | Ala | Phe | Asn | Ile | Pro<br>445 | Pro | Ile | Tyr |
| Thr | Ser<br>450 | Arg | Thr | Arg | Ile<br>455 | Asp | Ser | Asn | Arg | Asn<br>460 | Gln | Phe | Val | Tyr | Gln |
| Asp<br>465 | Gly | Gly | Phe | Ala | Thr<br>470 | Gln | Gln | Gly | Met | Pro<br>475 | Met | Pro | Tyr | Arg | Ala<br>480 |
| Thr | Thr | Ser | Thr | Ile<br>485 | Pro | Glu | Ala | Pro | Val<br>490 | Ala | Gln | Gly | Ala | Thr<br>495 | Ala |
| Glu | Met | Phe | Asp<br>500 | Asp | Ser | Cys | Cys | Asn<br>505 | Gly | Thr | Leu | Arg | Lys<br>510 | Pro | Val |
| Ala | Pro | His<br>515 | Val | Gln | Glu | Asp<br>520 | Ser | Thr | Gln | Arg | Tyr<br>525 | Ser | Ala | Asp |
| Pro | Thr<br>530 | Val | Phe | Ala | Pro | Glu<br>535 | Arg | Asn | Pro | Arg | Gly<br>540 | Glu | Leu | Asp | Glu |
| Glu<br>545 | Gly | Tyr | Met | Thr | Pro<br>550 | Met | His | Asp | Lys | Pro<br>555 | Lys | Gln | Glu | Tyr | Leu<br>560 |
| Asn | Pro | Val | Glu | Glu<br>565 | Asn | Pro | Phe | Val | Ser<br>570 | Arg | Arg | Lys | Asn | Gly<br>575 | Asp |
| Leu | Gln | Ala | Leu<br>580 | Asp | Asn | Pro | Glu | Tyr<br>585 | His | Ser | Ala | Ser | Ser<br>590 | Gly | Pro |
| Pro | Lys | Ala<br>595 | Glu | Asp | Glu | Tyr<br>600 | Val | Asn | Glu | Pro | Leu<br>605 | Tyr | Leu | Asn | Thr |
| Phe | Ala<br>610 | Asn | Ala | Leu | Gly<br>615 | Ser | Ala | Glu | Tyr | Met<br>620 | Lys | Asn | Ser | Val | Leu |
| Ser<br>625 | Val | Pro | Glu | Lys | Ala<br>630 | Lys | Lys | Ala | Phe | Asp<br>635 | Asn | Pro | Asp | Tyr | Trp<br>640 |
| Asn | His | Ser | Leu | Pro<br>645 | Pro | Arg | Ser | Thr | Leu<br>650 | Gln | His | Pro | Asp | Tyr<br>655 | Leu |
| Gln | Glu | Tyr | Ser<br>660 | Thr | Lys | Tyr | Phe | Tyr<br>665 | Lys | Gln | Asn | Gly | Arg<br>670 | Ile | Arg |
| Pro | Ile | Val<br>675 | Ala | Glu | Asn | Pro | Glu<br>680 | Tyr | Leu | Ser | Glu | Phe<br>685 | Ser | Leu | Lys |
| Pro | Gly<br>690 | Thr | Met | Leu | Pro | Pro<br>695 | Pro | Pro | Tyr | Arg | His<br>700 | Arg | Asn | Thr | Val |
| Val<br>705 |

( 2 ) INFORMATION FOR SEQ ID NO:5:

( i ) SEQUENCE CHARACTERISTICS:
        ( A ) LENGTH: 3307 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-3

( i x ) FEATURE:
        ( A ) NAME/KEY: CDS
        ( B ) LOCATION: 237..2859

( x i ) SEQUENCE DESCRIPTION: SEQ ID NO:5:

| | | | | | | |
|---|---|---|---|---|---|---|
| CGGCGGCGGC | GGCGGCTGTG | GAAGGAGCGC | GGTGGCCCAG | CCGCAGCCCC | GGGGACTCCT | 60 |
| CGCTGCTGAC | GGCGGTGGCC | GCGGCTCTAG | GCGGCCGCGG | GTCCGGACG | CCCGGGCCGA | 120 |
| GCGCCGCCCC | CCGCCCCTCC | CGCGGGCCTC | CCGCCCCTCC | TCCGCCACCC | TCCTCTCTGC | 180 |
| GCTCGCGGGC | CGGGCCCGGC | ATGGTGCGGC | GTCGCCGCCG | ATGGCTGAGG | CGGAGC | 236 |

| | | | | | | | | | | | | | | | | |
|---|---|---|---|---|---|---|---|---|---|---|---|---|---|---|---|---|
| ATG | GGG | TGG | CCG | GGG | CTC | CGG | CCG | CTG | CTG | CTG | GCG | GGA | CTG | GCT | TCT | 284 |
| Met | Gly | Trp | Pro | Gly | Leu | Arg | Pro | Leu | Leu | Leu | Ala | Gly | Leu | Ala | Ser | |
| 1 | | | | 5 | | | | | 10 | | | | | | 15 | |
| CTG | CTG | CTC | CCC | GGG | TCT | GCG | GCC | GCA | GGC | CTG | AAG | CTC | ATG | GGC | GCC | 332 |
| Leu | Leu | Leu | Pro | Gly | Ser | Ala | Ala | Ala | Gly | Leu | Lys | Leu | Met | Gly | Ala | |
| | | | 20 | | | | | 25 | | | | | 30 | | | |
| CCA | GTG | AAG | ATG | ACC | GTG | TCT | CAG | GGG | CAG | CCA | GTG | AAG | CTC | AAC | TGC | 380 |
| Pro | Val | Lys | Met | Thr | Val | Ser | Gln | Gly | Gln | Pro | Val | Lys | Leu | Asn | Cys | |
| | | 35 | | | | | 40 | | | | | 45 | | | | |
| AGC | GTG | GAG | GGG | ATG | GAG | GAC | CCT | GAC | ATC | CAC | TGG | ATG | AAG | GAT | GGC | 428 |
| Ser | Val | Glu | Gly | Met | Glu | Asp | Pro | Asp | Ile | His | Trp | Met | Lys | Asp | Gly | |
| | 50 | | | | 55 | | | | | 60 | | | | | | |
| ACC | GTG | GTC | CAG | AAT | GCA | AGC | CAG | GTG | TCC | ATC | TCC | ATC | AGC | GAG | CAC | 476 |
| Thr | Val | Val | Gln | Asn | Ala | Ser | Gln | Val | Ser | Ile | Ser | Ile | Ser | Glu | His | |
| 65 | | | | | 70 | | | | | 75 | | | | | 80 | |
| AGC | TGG | ATT | GGC | TTA | CTC | AGC | CTA | AAG | TCA | GTG | GAA | CGG | TCT | GAT | GCT | 524 |
| Ser | Trp | Ile | Gly | Leu | Leu | Ser | Leu | Lys | Ser | Val | Glu | Arg | Ser | Asp | Ala | |
| | | | | 85 | | | | | 90 | | | | | 95 | | |
| GGC | CTG | TAC | TGG | TGC | CAG | GTG | AAG | GAT | GGG | GAG | GAA | ACC | AAG | ATT | TCT | 572 |
| Gly | Leu | Tyr | Trp | Cys | Gln | Val | Lys | Asp | Gly | Glu | Glu | Thr | Lys | Ile | Ser | |
| | | | 100 | | | | | 105 | | | | | 110 | | | |
| CAG | TCA | GTA | TGG | CTC | ACT | GTC | GAA | GGT | GTG | CCA | TTC | TTC | ACA | GTG | GAA | 620 |
| Gln | Ser | Val | Trp | Leu | Thr | Val | Glu | Gly | Val | Pro | Phe | Phe | Thr | Val | Glu | |
| | | 115 | | | | | 120 | | | | | 125 | | | | |
| CCA | AAA | GAT | CTG | GCG | GTG | CCA | CCC | AAT | GCC | CCT | TTT | CAG | CTG | TCT | TGT | 668 |
| Pro | Lys | Asp | Leu | Ala | Val | Pro | Pro | Asn | Ala | Pro | Phe | Gln | Leu | Ser | Cys | |
| | | 130 | | | | | 135 | | | | | 140 | | | | |
| GAG | GCT | GTG | GGT | CCT | CCA | GAA | CCC | GTA | ACC | ATT | TAC | TGG | TGG | AGA | GGA | 716 |
| Glu | Ala | Val | Gly | Pro | Pro | Glu | Pro | Val | Thr | Ile | Tyr | Trp | Trp | Arg | Gly | |
| 145 | | | | | 150 | | | | | 155 | | | | | 160 | |
| CTC | ACT | AAG | GTT | GGG | GGA | CCT | GCT | CCC | TCT | CCC | TCT | GTT | TTA | AAT | GTG | 764 |
| Leu | Thr | Lys | Val | Gly | Gly | Pro | Ala | Pro | Ser | Pro | Ser | Val | Leu | Asn | Val | |
| | | | | 165 | | | | | 170 | | | | | 175 | | |
| ACA | GGA | GTG | ACC | CAG | CGC | ACA | GAG | TTT | TCT | TGT | GAA | GCC | CGC | AAC | ATA | 812 |
| Thr | Gly | Val | Thr | Gln | Arg | Thr | Glu | Phe | Ser | Cys | Glu | Ala | Arg | Asn | Ile | |
| | | | 180 | | | | | 185 | | | | | 190 | | | |
| AAA | GGC | CTG | GCC | ACT | TCC | CGA | CCA | GCC | ATT | GTT | CGC | CTT | CAA | GCA | CCG | 860 |
| Lys | Gly | Leu | Ala | Thr | Ser | Arg | Pro | Ala | Ile | Val | Arg | Leu | Gln | Ala | Pro | |
| | | 195 | | | | | 200 | | | | | 205 | | | | |
| CCT | GCA | GCT | CCT | TTC | AAC | ACC | ACA | GTA | ACA | ACG | ATC | TCC | AGC | TAC | AAC | 908 |
| Pro | Ala | Ala | Pro | Phe | Asn | Thr | Thr | Val | Thr | Thr | Ile | Ser | Ser | Tyr | Asn | |
| | 210 | | | | | 215 | | | | | 220 | | | | | |
| GCT | AGC | GTG | GCC | TGG | GTG | CCA | GGT | GCT | GAC | GGC | CTA | GCT | CTG | CTG | CAT | 956 |
| Ala | Ser | Val | Ala | Trp | Val | Pro | Gly | Ala | Asp | Gly | Leu | Ala | Leu | Leu | His | |
| 225 | | | | | 230 | | | | | 235 | | | | | 240 | |
| TCC | TGT | ACT | GTA | CAG | GTG | GCA | CAC | GCC | CCA | GGA | GAA | TGG | GAG | GCC | CTT | 1004 |
| Ser | Cys | Thr | Val | Gln | Val | Ala | His | Ala | Pro | Gly | Glu | Trp | Glu | Ala | Leu | |
| | | | | 245 | | | | | 250 | | | | | 255 | | |
| GCT | GTT | GTG | GTT | CCT | GTG | CCA | CCT | TTT | ACC | TGC | CTG | CTT | CGG | AAC | TTG | 1052 |
| Ala | Val | Val | Val | Pro | Val | Pro | Pro | Phe | Thr | Cys | Leu | Leu | Arg | Asn | Leu | |
| | | | 260 | | | | | 265 | | | | | 270 | | | |
| GCC | CCT | GCC | ACC | AAC | TAC | AGC | CTT | AGG | GTG | CGC | TGT | GCC | AAT | GCC | TTG | 1100 |
| Ala | Pro | Ala | Thr | Asn | Tyr | Ser | Leu | Arg | Val | Arg | Cys | Ala | Asn | Ala | Leu | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 275 |     |     |     |     | 280 |     |     |     |     |     | 285 |     |     |      |
| GGC | CCT | TCT | CCC | TAC | GGC | GAC | TGG | GTG | CCC | TTT | CAG | ACA | AAG | GGC | CTA | 1148 |
| Gly | Pro | Ser | Pro | Tyr | Gly | Asp | Trp | Val | Pro | Phe | Gln | Thr | Lys | Gly | Leu |      |
|     | 290 |     |     |     | 295 |     |     |     |     | 300 |     |     |     |     |     |      |
| GCG | CCA | CGC | AGA | GCT | CCT | CAG | AAT | TTC | CAT | GCC | ATT | CGT | ACC | GAC | TCA | 1196 |
| Ala | Pro | Arg | Arg | Ala | Pro | Gln | Asn | Phe | His | Ala | Ile | Arg | Thr | Asp | Ser |      |
| 305 |     |     |     |     | 310 |     |     |     |     | 315 |     |     |     |     | 320 |      |
| GGC | CTT | ATC | CTG | GAA | TGG | GAA | GAA | GTG | ATT | CCT | GAG | GAC | CCT | GGG | GAA | 1244 |
| Gly | Leu | Ile | Leu | Glu | Trp | Glu | Glu | Val | Ile | Pro | Glu | Asp | Pro | Gly | Glu |      |
|     |     |     |     |     | 325 |     |     |     | 330 |     |     |     |     |     | 335 |      |
| GGC | CCC | CTA | GGA | CCT | TAT | AAG | CTG | TCC | TGG | GTC | CAA | GAA | AAT | GGA | ACC | 1292 |
| Gly | Pro | Leu | Gly | Pro | Tyr | Lys | Leu | Ser | Trp | Val | Gln | Glu | Asn | Gly | Thr |      |
|     |     |     | 340 |     |     |     |     | 345 |     |     |     |     |     | 350 |     |      |
| CAG | GAT | GAG | CTG | ATG | GTG | GAA | GGG | ACC | AGG | GCC | AAT | CTG | ACC | GAC | TGG | 1340 |
| Gln | Asp | Glu | Leu | Met | Val | Glu | Gly | Thr | Arg | Ala | Asn | Leu | Thr | Asp | Trp |      |
|     |     | 355 |     |     |     |     | 360 |     |     |     |     | 365 |     |     |     |      |
| GTA | CCC | CAG | AAG | GAC | CTG | ATT | TTG | CGT | GTG | TGT | GCC | TCC | AAT | GCA | ATT | 1388 |
| Val | Pro | Gln | Lys | Asp | Leu | Ile | Leu | Arg | Val | Cys | Ala | Ser | Asn | Ala | Ile |      |
|     | 370 |     |     |     |     | 375 |     |     |     |     | 380 |     |     |     |     |      |
| GGT | GAT | GGG | CCC | TGG | AGT | CAG | CCA | CTG | GTG | GTG | TCT | TCT | CAT | GAC | CAT | 1436 |
| Gly | Asp | Gly | Pro | Trp | Ser | Gln | Pro | Leu | Val | Val | Ser | Ser | His | Asp | His |      |
| 385 |     |     |     |     | 390 |     |     |     |     | 395 |     |     |     |     | 400 |      |
| GCA | GGG | AGG | CAG | GGC | CCT | CCC | CAC | AGC | CGC | ACA | TCC | TGG | GTG | CCT | GTG | 1484 |
| Ala | Gly | Arg | Gln | Gly | Pro | Pro | His | Ser | Arg | Thr | Ser | Trp | Val | Pro | Val |      |
|     |     |     |     | 405 |     |     |     |     | 410 |     |     |     |     | 415 |     |      |
| GTC | CTG | GGC | GTG | CTC | ACC | GCC | CTG | ATC | ACA | GCT | GCT | GCC | TTG | GCC | CTC | 1532 |
| Val | Leu | Gly | Val | Leu | Thr | Ala | Leu | Ile | Thr | Ala | Ala | Ala | Leu | Ala | Leu |      |
|     |     |     | 420 |     |     |     |     | 425 |     |     |     |     | 430 |     |     |      |
| ATC | CTG | CTT | CGG | AAG | AGA | CGC | AAG | GAG | ACG | CGT | TTC | GGG | CAA | GCC | TTT | 1580 |
| Ile | Leu | Leu | Arg | Lys | Arg | Arg | Lys | Glu | Thr | Arg | Phe | Gly | Gln | Ala | Phe |      |
|     |     | 435 |     |     |     |     | 440 |     |     |     |     | 445 |     |     |     |      |
| GAC | AGT | GTC | ATG | GCC | CGA | GGG | GAG | CCA | GCT | GTA | CAC | TTC | CGG | GCA | GCC | 1628 |
| Asp | Ser | Val | Met | Ala | Arg | Gly | Glu | Pro | Ala | Val | His | Phe | Arg | Ala | Ala |      |
|     | 450 |     |     |     |     | 455 |     |     |     |     | 460 |     |     |     |     |      |
| CGA | TCT | TTC | AAT | CGA | GAA | AGG | CCT | GAA | CGC | ATT | GAG | GCC | ACA | TTG | GAT | 1676 |
| Arg | Ser | Phe | Asn | Arg | Glu | Arg | Pro | Glu | Arg | Ile | Glu | Ala | Thr | Leu | Asp |      |
| 465 |     |     |     |     | 470 |     |     |     |     | 475 |     |     |     |     | 480 |      |
| AGC | CTG | GGC | ATC | AGC | GAT | GAA | TTG | AAG | GAA | AAG | CTG | GAG | GAT | GTC | CTC | 1724 |
| Ser | Leu | Gly | Ile | Ser | Asp | Glu | Leu | Lys | Glu | Lys | Leu | Glu | Asp | Val | Leu |      |
|     |     |     |     | 485 |     |     |     |     | 490 |     |     |     |     | 495 |     |      |
| ATT | CCA | GAG | CAG | CAG | TTC | ACC | CTC | GGT | CGG | ATG | TTG | GGC | AAA | GGA | GAG | 1772 |
| Ile | Pro | Glu | Gln | Gln | Phe | Thr | Leu | Gly | Arg | Met | Leu | Gly | Lys | Gly | Glu |      |
|     |     |     | 500 |     |     |     |     | 505 |     |     |     |     | 510 |     |     |      |
| TTT | GGA | TCA | GTG | CGG | GAA | GCC | CAG | CTA | AAG | CAG | GAA | GAT | GGC | TCC | TTC | 1820 |
| Phe | Gly | Ser | Val | Arg | Glu | Ala | Gln | Leu | Lys | Gln | Glu | Asp | Gly | Ser | Phe |      |
|     |     | 515 |     |     |     |     | 520 |     |     |     |     | 525 |     |     |     |      |
| GTG | AAA | GTG | GCA | GTG | AAG | ATG | CTG | AAA | GCT | GAC | ATC | ATT | GCC | TCA | AGC | 1868 |
| Val | Lys | Val | Ala | Val | Lys | Met | Leu | Lys | Ala | Asp | Ile | Ile | Ala | Ser | Ser |      |
|     | 530 |     |     |     |     | 535 |     |     |     |     | 540 |     |     |     |     |      |
| GAC | ATA | GAA | GAG | TTC | CTC | CGG | GAA | GCA | GCT | TGC | ATG | AAG | GAG | TTT | GAC | 1916 |
| Asp | Ile | Glu | Glu | Phe | Leu | Arg | Glu | Ala | Ala | Cys | Met | Lys | Glu | Phe | Asp |      |
| 545 |     |     |     |     | 550 |     |     |     |     | 555 |     |     |     |     | 560 |      |
| CAT | CCA | CAC | GTG | GCC | AAG | CTT | GTT | GGG | GTG | AGC | CTC | CGG | AGC | AGG | GCT | 1964 |
| His | Pro | His | Val | Ala | Lys | Leu | Val | Gly | Val | Ser | Leu | Arg | Ser | Arg | Ala |      |
|     |     |     |     | 565 |     |     |     |     | 570 |     |     |     |     | 575 |     |      |
| AAA | GGT | CGT | CTC | CCC | ATT | CCC | ATG | GTC | ATC | CTG | CCC | TTC | ATG | AAA | CAT | 2012 |
| Lys | Gly | Arg | Leu | Pro | Ile | Pro | Met | Val | Ile | Leu | Pro | Phe | Met | Lys | His |      |
|     |     |     | 580 |     |     |     |     | 585 |     |     |     |     | 590 |     |     |      |
| GGA | GAC | TTG | CAC | GCC | TTT | CTG | CTC | GCC | TCC | CGA | ATC | GGG | GAG | AAC | CCT | 2060 |
| Gly | Asp | Leu | His | Ala | Phe | Leu | Leu | Ala | Ser | Arg | Ile | Gly | Glu | Asn | Pro |      |

-continued

```
              595                    600                       605
TTT AAC CTG CCC CTC CAG ACC CTG GTC CGG TTC ATG GTG GAC ATT CGC    2108
Phe Asn Leu Pro Leu Gln Thr Leu Val Arg Phe Met Val Asp Ile Arg
    610             615                 620

TGT GGC ATG GAG TAC CTG AGC TCC CGG AAC TTC ATC CAC CGA GAC CTA    2156
Cys Gly Met Glu Tyr Leu Ser Ser Arg Asn Phe Ile His Arg Asp Leu
625             630                 635                     640

GCA GCT CGG AAT TGC ATG CTG GCC GAG GAC ATG ACA GTG TGT GTG GCT    2204
Ala Ala Arg Asn Cys Met Leu Ala Glu Asp Met Thr Val Cys Val Ala
            645                 650                 655

GAT TTT GGA CTC TCT CGG AAA ATC TAT AGC GGG GAC TAT TAT CGT CAG    2252
Asp Phe Gly Leu Ser Arg Lys Ile Tyr Ser Gly Asp Tyr Tyr Arg Gln
        660                 665                 670

GGC TGT GCC TCC AAA TTG CCC GTC AAG TGG CTG GCC CTG GAG AGC TTG    2300
Gly Cys Ala Ser Lys Leu Pro Val Lys Trp Leu Ala Leu Glu Ser Leu
            675             680                 685

GCT GAC AAC TTG TAT ACT GTA CAC AGT GAT GTG TGG GCC TTC GGG GTG    2348
Ala Asp Asn Leu Tyr Thr Val His Ser Asp Val Trp Ala Phe Gly Val
    690                 695                 700

ACC ATG TGG GAG ATC ATG ACT CGT GGG CAG ACG CCA TAT GCT GGC ATT    2396
Thr Met Trp Glu Ile Met Thr Arg Gly Gln Thr Pro Tyr Ala Gly Ile
705             710                 715                     720

GAA AAT GCC GAG ATT TAC AAC TAC CTC ATC GGC GGG AAC CGC CTG AAG    2444
Glu Asn Ala Glu Ile Tyr Asn Tyr Leu Ile Gly Gly Asn Arg Leu Lys
            725                 730                 735

CAG CCT CCG GAG TGC ATG GAG GAA GTG TAT GAT CTC ATG TAC CAG TGC    2492
Gln Pro Pro Glu Cys Met Glu Glu Val Tyr Asp Leu Met Tyr Gln Cys
        740                 745                 750

TGG AGC GCC GAC CCC AAG CAG CGC CCA AGC TTC ACG TGT CTG CGA ATG    2540
Trp Ser Ala Asp Pro Lys Gln Arg Pro Ser Phe Thr Cys Leu Arg Met
            755             760                 765

GAA CTG GAG AAC ATT CTG GGC CAC CTG TCT GTG CTG TCC ACC AGC CAG    2588
Glu Leu Glu Asn Ile Leu Gly His Leu Ser Val Leu Ser Thr Ser Gln
    770                 775                 780

GAC CCC TTG TAC ATC AAC ATT GAG AGA GCT GAG CAG CCT ACT GAG AGT    2636
Asp Pro Leu Tyr Ile Asn Ile Glu Arg Ala Glu Gln Pro Thr Glu Ser
785             790                 795                     800

GGC AGC CCT GAG GTC CAC TGT GGA GAG CGA TCC AGC AGC GAG GCA GGG    2684
Gly Ser Pro Glu Val His Cys Gly Glu Arg Ser Ser Ser Glu Ala Gly
            805             810                 815

GAC GGC AGT GGC GTG GGG GCA GTA GGT GGC ATC CCC AGT GAC TCT CGG    2732
Asp Gly Ser Gly Val Gly Ala Val Gly Gly Ile Pro Ser Asp Ser Arg
        820                 825                 830

TAC ATC TTC AGC CCC GGA GGG CTA TCC GAG TCA CCA GGG CAG CTG GAG    2780
Tyr Ile Phe Ser Pro Gly Gly Leu Ser Glu Ser Pro Gly Gln Leu Glu
        835             840                 845

CAG CAG CCA GAA AGC CCC CTC AAT GAG AAC CAG AGG CTG TTG TTG CTG    2828
Gln Gln Pro Glu Ser Pro Leu Asn Glu Asn Gln Arg Leu Leu Leu Leu
850             855                 860

CAG CAA GGG CTA CTG CCT CAC AGT AGC TGT T AACCCTCAGG CAGAGGAAAG    2879
Gln Gln Gly Leu Leu Pro His Ser Ser Cys
865             870

TTGGGGCCCC TGGCTCTGCT GACCGCTGTG CTGCCTGACT AGGCCCAGTC TGATCACAGC    2939

CCAGGCAGCA AGGTATGGAG CTCCTGTGG TAGCCCTCCC AAGCTGTGCT GGCGCCTGGA    2999

CGGACCAAAT TGCCCAATCC CAGTTCTTCC TGCAGCCGCT CTGGCCAGCC TGGCATCAGT    3059

TCAGGCCTTG GCTTACAGGA GGTGAGCCAG AGCTGGTTGC CTGAATGCAG GCAGCTGGCA    3119

GGAGGGGAGG GTGGCTATGT TTCCATGGGT ACCATGGTTG TGGATGGCAG TAAGGGAGGG    3179
```

```
TAGCAACAGC  CCTGTGCGCC  CTACCCTCCT  GGCTGAGCTG  CTCCTACTTT  AGTGCATGCT   3239

TGGAGCCGCC  TGCAGCCTGG  AACTCAGCAC  TGCCCACCAC  ACTTGGGCCG  AAATGCCAGG   3299

TTTGCCCC                                                                3307
```

( 2 ) INFORMATION FOR SEQ ID NO:6:

( i ) SEQUENCE CHARACTERISTICS:
        ( A ) LENGTH: 874 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Gly  Trp  Pro  Gly  Leu  Arg  Pro  Leu  Leu  Leu  Ala  Gly  Leu  Ala  Ser
 1              5                        10                       15

Leu  Leu  Leu  Pro  Gly  Ser  Ala  Ala  Gly  Leu  Lys  Leu  Met  Gly  Ala
           20                  25                       30

Pro  Val  Lys  Met  Thr  Val  Ser  Gln  Gly  Gln  Pro  Val  Lys  Leu  Asn  Cys
           35                       40                       45

Ser  Val  Glu  Gly  Met  Glu  Asp  Pro  Asp  Ile  His  Trp  Met  Lys  Asp  Gly
      50                       55                       60

Thr  Val  Val  Gln  Asn  Ala  Ser  Gln  Val  Ser  Ile  Ser  Ile  Ser  Glu  His
 65                       70                       75                       80

Ser  Trp  Ile  Gly  Leu  Leu  Ser  Leu  Lys  Ser  Val  Glu  Arg  Ser  Asp  Ala
                     85                       90                       95

Gly  Leu  Tyr  Trp  Cys  Gln  Val  Lys  Asp  Gly  Glu  Glu  Thr  Lys  Ile  Ser
                    100                      105                      110

Gln  Ser  Val  Trp  Leu  Thr  Val  Glu  Gly  Val  Pro  Phe  Phe  Thr  Val  Glu
           115                      120                      125

Pro  Lys  Asp  Leu  Ala  Val  Pro  Pro  Asn  Ala  Pro  Phe  Gln  Leu  Ser  Cys
     130                      135                      140

Glu  Ala  Val  Gly  Pro  Pro  Glu  Pro  Val  Thr  Ile  Tyr  Trp  Trp  Arg  Gly
145                      150                      155                      160

Leu  Thr  Lys  Val  Gly  Gly  Pro  Ala  Pro  Ser  Pro  Ser  Val  Leu  Asn  Val
                    165                      170                      175

Thr  Gly  Val  Thr  Gln  Arg  Thr  Glu  Phe  Ser  Cys  Glu  Ala  Arg  Asn  Ile
                    180                      185                      190

Lys  Gly  Leu  Ala  Thr  Ser  Arg  Pro  Ala  Ile  Val  Arg  Leu  Gln  Ala  Pro
           195                      200                      205

Pro  Ala  Ala  Pro  Phe  Asn  Thr  Thr  Val  Thr  Thr  Ile  Ser  Ser  Tyr  Asn
     210                      215                      220

Ala  Ser  Val  Ala  Trp  Val  Pro  Gly  Ala  Asp  Gly  Leu  Ala  Leu  Leu  His
225                      230                      235                      240

Ser  Cys  Thr  Val  Gln  Val  Ala  His  Ala  Pro  Gly  Glu  Trp  Glu  Ala  Leu
                    245                      250                      255

Ala  Val  Val  Val  Pro  Val  Pro  Pro  Phe  Thr  Cys  Leu  Leu  Arg  Asn  Leu
                    260                      265                      270

Ala  Pro  Ala  Thr  Asn  Tyr  Ser  Leu  Arg  Val  Arg  Cys  Ala  Asn  Ala  Leu
           275                      280                      285

Gly  Pro  Ser  Pro  Tyr  Gly  Asp  Trp  Val  Pro  Phe  Gln  Thr  Lys  Gly  Leu
     290                      295                      300

Ala  Pro  Arg  Arg  Ala  Pro  Gln  Asn  Phe  His  Ala  Ile  Arg  Thr  Asp  Ser
305                      310                      315                      320

Gly  Leu  Ile  Leu  Glu  Trp  Glu  Glu  Val  Ile  Pro  Glu  Asp  Pro  Gly  Glu
                    325                      330                      335
```

-continued

```
Gly  Pro  Leu  Gly  Pro  Tyr  Lys  Leu  Ser  Trp  Val  Gln  Glu  Asn  Gly  Thr
               340                 345                          350

Gln  Asp  Glu  Leu  Met  Val  Glu  Gly  Thr  Arg  Ala  Asn  Leu  Thr  Asp  Trp
          355                      360                     365

Val  Pro  Gln  Lys  Asp  Leu  Ile  Leu  Arg  Val  Cys  Ala  Ser  Asn  Ala  Ile
     370                 375                      380

Gly  Asp  Gly  Pro  Trp  Ser  Gln  Pro  Leu  Val  Val  Ser  Ser  His  Asp  His
385                      390                     395                           400

Ala  Gly  Arg  Gln  Gly  Pro  Pro  His  Ser  Arg  Thr  Ser  Trp  Val  Pro  Val
                405                      410                          415

Val  Leu  Gly  Val  Leu  Thr  Ala  Leu  Ile  Thr  Ala  Ala  Ala  Leu  Ala  Leu
               420                 425                          430

Ile  Leu  Leu  Arg  Lys  Arg  Arg  Lys  Glu  Thr  Arg  Phe  Gly  Gln  Ala  Phe
               435                 440                          445

Asp  Ser  Val  Met  Ala  Arg  Gly  Glu  Pro  Ala  Val  His  Phe  Arg  Ala  Ala
     450                      455                     460

Arg  Ser  Phe  Asn  Arg  Glu  Arg  Pro  Glu  Arg  Ile  Glu  Ala  Thr  Leu  Asp
465                      470                     475                           480

Ser  Leu  Gly  Ile  Ser  Asp  Glu  Leu  Lys  Glu  Lys  Leu  Glu  Asp  Val  Leu
               485                 490                          495

Ile  Pro  Glu  Gln  Phe  Thr  Leu  Gly  Arg  Met  Leu  Gly  Lys  Gly  Glu
                500                     505                          510

Phe  Gly  Ser  Val  Arg  Glu  Ala  Gln  Leu  Lys  Gln  Glu  Asp  Gly  Ser  Phe
          515                      520                     525

Val  Lys  Val  Ala  Val  Lys  Met  Leu  Lys  Ala  Asp  Ile  Ile  Ala  Ser  Ser
     530                      535                     540

Asp  Ile  Glu  Glu  Phe  Leu  Arg  Glu  Ala  Ala  Cys  Met  Lys  Glu  Phe  Asp
545                      550                     555                           560

His  Pro  His  Val  Ala  Lys  Leu  Val  Gly  Val  Ser  Leu  Arg  Ser  Arg  Ala
                565                     570                          575

Lys  Gly  Arg  Leu  Pro  Ile  Pro  Met  Val  Ile  Leu  Pro  Phe  Met  Lys  His
               580                 585                          590

Gly  Asp  Leu  His  Ala  Phe  Leu  Leu  Ala  Ser  Arg  Ile  Gly  Glu  Asn  Pro
               595                 600                          605

Phe  Asn  Leu  Pro  Leu  Gln  Thr  Leu  Val  Arg  Phe  Met  Val  Asp  Ile  Arg
     610                      615                     620

Cys  Gly  Met  Glu  Tyr  Leu  Ser  Ser  Arg  Asn  Phe  Ile  His  Arg  Asp  Leu
625                      630                     635                           640

Ala  Ala  Arg  Asn  Cys  Met  Leu  Ala  Glu  Asp  Met  Thr  Val  Cys  Val  Ala
                645                     650                          655

Asp  Phe  Gly  Leu  Ser  Arg  Lys  Ile  Tyr  Ser  Gly  Asp  Tyr  Tyr  Arg  Gln
               660                 665                          670

Gly  Cys  Ala  Ser  Lys  Leu  Pro  Val  Lys  Trp  Leu  Ala  Leu  Glu  Ser  Leu
          675                      680                     685

Ala  Asp  Asn  Leu  Tyr  Thr  Val  His  Ser  Asp  Val  Trp  Ala  Phe  Gly  Val
     690                      695                     700

Thr  Met  Trp  Glu  Ile  Met  Thr  Arg  Gly  Gln  Thr  Pro  Tyr  Ala  Gly  Ile
705                      710                     715                           720

Glu  Asn  Ala  Glu  Ile  Tyr  Asn  Tyr  Leu  Ile  Gly  Gly  Asn  Arg  Leu  Lys
                725                     730                          735

Gln  Pro  Pro  Glu  Cys  Met  Glu  Glu  Val  Tyr  Asp  Leu  Met  Tyr  Gln  Cys
               740                 745                          750

Trp  Ser  Ala  Asp  Pro  Lys  Gln  Arg  Pro  Ser  Phe  Thr  Cys  Leu  Arg  Met
```

|     | 755 |     |     |     |     | 760 |     |     |     |     | 765 |     |     |     |
| --- | --- | --- | --- | --- | --- | --- | --- | --- | --- | --- | --- | --- | --- | --- |
| Glu | Leu | Glu | Asn | Ile | Leu | Gly | His | Leu | Ser | Val | Leu | Ser | Thr | Ser | Gln |
|     |     | 770 |     |     |     |     | 775 |     |     |     |     | 780 |     |     |     |
| Asp | Pro | Leu | Tyr | Ile | Asn | Ile | Glu | Arg | Ala | Glu | Gln | Pro | Thr | Glu | Ser |
| 785 |     |     |     |     | 790 |     |     |     |     | 795 |     |     |     |     | 800 |
| Gly | Ser | Pro | Glu | Val | His | Cys | Gly | Glu | Arg | Ser | Ser | Ser | Glu | Ala | Gly |
|     |     |     |     | 805 |     |     |     |     | 810 |     |     |     |     | 815 |     |
| Asp | Gly | Ser | Gly | Val | Gly | Ala | Val | Gly | Gly | Ile | Pro | Ser | Asp | Ser | Arg |
|     |     |     | 820 |     |     |     |     | 825 |     |     |     |     | 830 |     |     |
| Tyr | Ile | Phe | Ser | Pro | Gly | Gly | Leu | Ser | Glu | Ser | Pro | Gly | Gln | Leu | Glu |
|     |     | 835 |     |     |     |     | 840 |     |     |     |     | 845 |     |     |     |
| Gln | Gln | Pro | Glu | Ser | Pro | Leu | Asn | Glu | Asn | Gln | Arg | Leu | Leu | Leu | Leu |
|     | 850 |     |     |     |     | 855 |     |     |     |     | 860 |     |     |     |     |
| Gln | Gln | Gly | Leu | Leu | Pro | His | Ser | Ser | Cys |
| 865 |     |     |     |     | 870 |

(2) INFORMATION FOR SEQ ID NO:7:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: DNA (vii) IMMEDIATE SOURCE:
        (B) CLONE: Tyro-4

(ix) FEATURE:
        (A) NAME/KEY: CDS
        (B) LOCATION: 1..165

(xi) SEQUENCE DESCRIPTION: SEQ ID NO:7:

| AAC | ATC | TTG | ATC | AAC | AGT | AAC | TTG | GTG | TGC | AAA | GTC | TCT | GAC | TTC | GGA | 48 |
| --- | --- | --- | --- | --- | --- | --- | --- | --- | --- | --- | --- | --- | --- | --- | --- | --- |
| Asn | Ile | Leu | Ile | Asn | Ser | Asn | Leu | Val | Cys | Lys | Val | Ser | Asp | Phe | Gly |    |
| 1   |     |     |     | 5   |     |     |     |     | 10  |     |     |     |     | 15  |     |    |
| CTT | TCT | CGA | GTG | TTG | GAA | GAT | GAC | CCT | GAA | GCT | GCT | TAC | ACC | ACC | AGA | 96 |
| Leu | Ser | Arg | Val | Leu | Glu | Asp | Asp | Pro | Glu | Ala | Ala | Tyr | Thr | Thr | Arg |    |
|     |     |     | 20  |     |     |     |     | 25  |     |     |     |     | 30  |     |     |    |
| GGA | GGA | AAG | ATA | CCA | ATA | AGG | TGG | ACA | TCA | CCA | GAA | GCA | ATT | GCC | TAC | 144 |
| Gly | Gly | Lys | Ile | Pro | Ile | Arg | Trp | Thr | Ser | Pro | Glu | Ala | Ile | Ala | Tyr |    |
|     |     | 35  |     |     |     |     | 40  |     |     |     |     | 45  |     |     |     |    |
| CGC | AAG | TTC | ACA | TCA | GCC | AGC |     |     |     |     |     |     |     |     |     | 165 |
| Arg | Lys | Phe | Thr | Ser | Ala | Ser |     |     |     |     |     |     |     |     |     |    |
|     | 50  |     |     |     |     | 55  |

(2) INFORMATION FOR SEQ ID NO:8:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:8:

| Asn | Ile | Leu | Ile | Asn | Ser | Asn | Leu | Val | Cys | Lys | Val | Ser | Asp | Phe | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Leu | Ser | Arg | Val | Leu | Glu | Asp | Asp | Pro | Glu | Ala | Ala | Tyr | Thr | Thr | Arg |
|     |     |     | 20  |     |     |     |     | 25  |     |     |     |     | 30  |     |     |
| Gly | Gly | Lys | Ile | Pro | Ile | Arg | Trp | Thr | Ser | Pro | Glu | Ala | Ile | Ala | Tyr |
|     |     | 35  |     |     |     |     | 40  |     |     |     |     | 45  |     |     |     |

```
Arg  Lys  Phe  Thr  Ser  Ala  Ser
     50                  55
```

( 2 ) INFORMATION FOR SEQ ID NO:9:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-5

( i x ) FEATURE:
        ( A ) NAME/KEY: CDS
        ( B ) LOCATION: 1..171

( x i ) SEQUENCE DESCRIPTION: SEQ ID NO:9:

```
AAC  ATC  CTT  GTC  AAT  AGC  AAC  CTG  GTG  TGC  AAG  GTG  TCT  GAC  TTC  GGG         48
Asn  Ile  Leu  Val  Asn  Ser  Asn  Leu  Val  Cys  Lys  Val  Ser  Asp  Phe  Gly
 1                   5                  10                  15

CTC  TCA  CGC  TTC  CTG  GAG  GAC  GAC  ACA  TCT  GAC  CCC  ACC  TAC  ACC  AGC         96
Leu  Ser  Arg  Phe  Leu  Glu  Asp  Asp  Thr  Ser  Asp  Pro  Thr  Tyr  Thr  Ser
              20                       25                       30

GCT  CTG  GGT  GGG  AAG  ATC  CCC  ATC  CGT  TGG  ACA  GCA  CCG  GAA  GCC  ATC        144
Ala  Leu  Gly  Gly  Lys  Ile  Pro  Ile  Arg  Trp  Thr  Ala  Pro  Glu  Ala  Ile
                   35                  40                       45

CAG  TAC  CGG  AAA  TTC  ACC  TCA  GCC  AGT                                            171
Gln  Tyr  Arg  Lys  Phe  Thr  Ser  Ala  Ser
     50                  55
```

( 2 ) INFORMATION FOR SEQ ID NO:10:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Asn  Ile  Leu  Val  Asn  Ser  Asn  Leu  Val  Cys  Lys  Val  Ser  Asp  Phe  Gly
 1                   5                  10                  15

Leu  Ser  Arg  Phe  Leu  Glu  Asp  Asp  Thr  Ser  Asp  Pro  Thr  Tyr  Thr  Ser
              20                       25                       30

Ala  Leu  Gly  Gly  Lys  Ile  Pro  Ile  Arg  Trp  Thr  Ala  Pro  Glu  Ala  Ile
                   35                  40                       45

Gln  Tyr  Arg  Lys  Phe  Thr  Ser  Ala  Ser
     50                  55
```

( 2 ) INFORMATION FOR SEQ ID NO:11:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-6

( i x ) FEATURE:
        ( A ) NAME/KEY: CDS
        ( B ) LOCATION: 1..171

( x i ) SEQUENCE DESCRIPTION: SEQ ID NO:11:

| AAC | ATC | CTT | GTC | AAC | AGT | AAC | TTG | GTC | TGC | AAA | GTA | TCT | GAC | TTT | GGG | 48 |
|-----|-----|-----|-----|-----|-----|-----|-----|-----|-----|-----|-----|-----|-----|-----|-----|----|
| Asn | Ile | Leu | Val | Asn | Ser | Asn | Leu | Val | Cys | Lys | Val | Ser | Asp | Phe | Gly |    |
| 1   |     |     |     | 5   |     |     |     |     | 10  |     |     |     |     | 15  |     |    |

| CTC | TCC | CGC | TTC | CTG | GAG | GAC | GAC | CCC | TCA | GAC | CCC | ACC | TAC | ACC | AGC | 96 |
|-----|-----|-----|-----|-----|-----|-----|-----|-----|-----|-----|-----|-----|-----|-----|-----|----|
| Leu | Ser | Arg | Phe | Leu | Glu | Asp | Asp | Pro | Ser | Asp | Pro | Thr | Tyr | Thr | Ser |    |
|     |     |     | 20  |     |     |     |     | 25  |     |     |     |     | 30  |     |     |    |

| TCC | CTG | GGT | GGG | AAG | ATC | CCT | ATC | CGT | TGG | ACC | GCC | CCA | GAG | GCC | ATA | 144 |
|-----|-----|-----|-----|-----|-----|-----|-----|-----|-----|-----|-----|-----|-----|-----|-----|-----|
| Ser | Leu | Gly | Gly | Lys | Ile | Pro | Ile | Arg | Trp | Thr | Ala | Pro | Glu | Ala | Ile |     |
|     |     |     | 35  |     |     |     | 40  |     |     |     |     | 45  |     |     |     |     |

| GCC | TAT | CGG | AAG | TTC | ACG | TCT | GCC | AGC | 171 |
|-----|-----|-----|-----|-----|-----|-----|-----|-----|-----|
| Ala | Tyr | Arg | Lys | Phe | Thr | Ser | Ala | Ser |     |
|     | 50  |     |     |     |     | 55  |     |     |     |

( 2 ) INFORMATION FOR SEQ ID NO:12:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Asn | Ile | Leu | Val | Asn | Ser | Asn | Leu | Val | Cys | Lys | Val | Ser | Asp | Phe | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ser | Arg | Phe | Leu | Glu | Asp | Asp | Pro | Ser | Asp | Pro | Thr | Tyr | Thr | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Leu | Gly | Gly | Lys | Ile | Pro | Ile | Arg | Trp | Thr | Ala | Pro | Glu | Ala | Ile |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Ala | Tyr | Arg | Lys | Phe | Thr | Ser | Ala | Ser |
|-----|-----|-----|-----|-----|-----|-----|-----|-----|
|     | 50  |     |     |     |     | 55  |     |     |

( 2 ) INFORMATION FOR SEQ ID NO:13:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-7

( i x ) FEATURE:
        ( A ) NAME/KEY: CDS
        ( B ) LOCATION: 1..162

( x i ) SEQUENCE DESCRIPTION: SEQ ID NO:13:

| AAC | TGC | ATG | CTG | AAT | GAG | AAC | ATG | TCC | GTG | TGC | GTG | GCA | GAC | TTC | GGG | 48 |
|-----|-----|-----|-----|-----|-----|-----|-----|-----|-----|-----|-----|-----|-----|-----|-----|----|
| Asn | Cys | Met | Leu | Asn | Glu | Asn | Met | Ser | Val | Cys | Val | Ala | Asp | Phe | Gly |    |
| 1   |     |     |     | 5   |     |     |     |     | 10  |     |     |     |     | 15  |     |    |

| CTC | TCC | AAG | AAG | ATC | TAC | AAT | GGG | GAT | TAC | TAC | CGC | CAA | GGG | CGC | ATT | 96 |
|-----|-----|-----|-----|-----|-----|-----|-----|-----|-----|-----|-----|-----|-----|-----|-----|----|
| Leu | Ser | Lys | Lys | Ile | Tyr | Asn | Gly | Asp | Tyr | Tyr | Arg | Gln | Gly | Arg | Ile |    |
|     |     |     | 20  |     |     |     |     | 25  |     |     |     |     | 30  |     |     |    |

| GCC | AAG | ATG | CCA | GTC | AAG | TGG | ATT | GCT | ATC | GAG | AGT | CTG | GCA | GAT | CGA | 144 |
|-----|-----|-----|-----|-----|-----|-----|-----|-----|-----|-----|-----|-----|-----|-----|-----|-----|
| Ala | Lys | Met | Pro | Val | Lys | Trp | Ile | Ala | Ile | Glu | Ser | Leu | Ala | Asp | Arg |     |
|     |     |     | 35  |     |     |     | 40  |     |     |     |     | 45  |     |     |     |     |

| GTC | TAC | ACC | AGC | AAG | AGT | 162 |
|-----|-----|-----|-----|-----|-----|-----|
| Val | Tyr | Thr | Ser | Lys | Ser |     |
|     | 50  |     |     |     |     |     |

( 2 ) INFORMATION FOR SEQ ID NO:14:

( i ) SEQUENCE CHARACTERISTICS:
    ( A ) LENGTH: 54 amino acids
    ( B ) TYPE: amino acid
    ( D ) TOPOLOGY: linear ( i i ) MOLECULE TYPE: protein ( x i ) SEQUENCE DESCRIPTION: SEQ ID NO:14:

```
Asn  Cys  Met  Leu  Asn  Glu  Asn  Met  Ser  Val  Cys  Val  Ala  Asp  Phe  Gly
 1              5                        10                       15

Leu  Ser  Lys  Lys  Ile  Tyr  Asn  Gly  Asp  Tyr  Tyr  Arg  Gln  Gly  Arg  Ile
              20                        25                       30

Ala  Lys  Met  Pro  Val  Lys  Trp  Ile  Ala  Ile  Glu  Ser  Leu  Ala  Asp  Arg
              35                        40                       45

Val  Tyr  Thr  Ser  Lys  Ser
              50
```

( 2 ) INFORMATION FOR SEQ ID NO:15:

( i ) SEQUENCE CHARACTERISTICS:
    ( A ) LENGTH: 159 base pairs
    ( B ) TYPE: nucleic acid
    ( C ) STRANDEDNESS: single
    ( D ) TOPOLOGY: linear ( i i ) MOLECULE TYPE: DNA ( v i i ) IMMEDIATE SOURCE:
    ( B ) CLONE: Tyro-8

( i x ) FEATURE:
    ( A ) NAME/KEY: CDS
    ( B ) LOCATION: 1..159

( x i ) SEQUENCE DESCRIPTION: SEQ ID NO:15:

```
AAC  TGT  TTG  GTG  GAC  AGT  GAT  CTC  TCC  GTG  AAA  GTC  TCA  GAC  TTT  GGA      48
Asn  Cys  Leu  Val  Asp  Ser  Asp  Leu  Ser  Val  Lys  Val  Ser  Asp  Phe  Gly
 1              5                        10                       15

ATG  ACG  AGA  TAT  GTC  CTT  GAT  GAC  CAG  TAT  GTC  AGT  TCA  GTA  GGA  ACC      96
Met  Thr  Arg  Tyr  Val  Leu  Asp  Asp  Gln  Tyr  Val  Ser  Ser  Val  Gly  Thr
              20                        25                       30

AAG  TTT  CCA  GTC  AAG  TGG  TCG  GCC  CCA  GAG  GTG  TTT  CAC  TAT  TTC  AAA     144
Lys  Phe  Pro  Val  Lys  Trp  Ser  Ala  Pro  Glu  Val  Phe  His  Tyr  Phe  Lys
              35                        40                       45

TAC  AGC  AGC  AAG  TCG                                                            159
Tyr  Ser  Ser  Lys  Ser
              50
```

( 2 ) INFORMATION FOR SEQ ID NO:16:

( i ) SEQUENCE CHARACTERISTICS:
    ( A ) LENGTH: 53 amino acids
    ( B ) TYPE: amino acid
    ( D ) TOPOLOGY: linear ( i i ) MOLECULE TYPE: protein ( x i ) SEQUENCE DESCRIPTION: SEQ ID NO:16:

```
Asn  Cys  Leu  Val  Asp  Ser  Asp  Leu  Ser  Val  Lys  Val  Ser  Asp  Phe  Gly
 1              5                        10                       15

Met  Thr  Arg  Tyr  Val  Leu  Asp  Asp  Gln  Tyr  Val  Ser  Ser  Val  Gly  Thr
              20                        25                       30

Lys  Phe  Pro  Val  Lys  Trp  Ser  Ala  Pro  Glu  Val  Phe  His  Tyr  Phe  Lys
              35                        40                       45
```

Tyr Ser Ser Lys Ser
    50

( 2 ) INFORMATION FOR SEQ ID NO:17:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-9

( i x ) FEATURE:
        ( A ) NAME/KEY: CDS
        ( B ) LOCATION: 1..162

( x i ) SEQUENCE DESCRIPTION: SEQ ID NO:17:

```
AAC  GTG  CTG  GTG  ACC  GAG  GAT  GAC  GTG  ATG  AAG  ATC  GCT  GAC  TTT  GGT        48
Asn  Val  Leu  Val  Thr  Glu  Asp  Asp  Val  Met  Lys  Ile  Ala  Asp  Phe  Gly
 1                    5                        10                       15

CTG  GCC  CGT  GGT  GTC  CAC  CAC  ATC  GAC  TAC  TAT  AAG  AAA  ACC  AGC  AAT        96
Leu  Ala  Arg  Gly  Val  His  His  Ile  Asp  Tyr  Tyr  Lys  Lys  Thr  Ser  Asn
               20                       25                       30

GGC  CGC  CTG  CCA  GTC  AAG  TGG  ATG  GCT  CCT  GAG  GCG  TTG  TTT  GAC  CGT       144
Gly  Arg  Leu  Pro  Val  Lys  Trp  Met  Ala  Pro  Glu  Ala  Leu  Phe  Asp  Arg
          35                       40                       45

GTA  TAC  ACA  CAC  CAG  AGT                                                          162
Val  Tyr  Thr  His  Gln  Ser
 50
```

( 2 ) INFORMATION FOR SEQ ID NO:18:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Asn  Val  Leu  Val  Thr  Glu  Asp  Asp  Val  Met  Lys  Ile  Ala  Asp  Phe  Gly
 1                    5                        10                       15

Leu  Ala  Arg  Gly  Val  His  His  Ile  Asp  Tyr  Tyr  Lys  Lys  Thr  Ser  Asn
               20                       25                       30

Gly  Arg  Leu  Pro  Val  Lys  Trp  Met  Ala  Pro  Glu  Ala  Leu  Phe  Asp  Arg
          35                       40                       45

Val  Tyr  Thr  His  Gln  Ser
 50
```

( 2 ) INFORMATION FOR SEQ ID NO:19:

( i ) SEQUENCE CHARACTERISTICS:
        ( A ) LENGTH: 3120 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-10

( i x ) FEATURE:
        ( A ) NAME/KEY: CDS
        ( B ) LOCATION: 485..3047

( x i ) SEQUENCE DESCRIPTION: SEQ ID NO:19:

| | | | | | | |
|---|---|---|---|---|---|---|
| GGGCCCGGGT | CTAAGTGGAC | TTCTCTTGGT | GTGTCAGGAA | AAGTTCGGAA | AAGCGGCAGA | 60 |
| GGGCAGAGTT | TGAATCAGGG | CGGAAGGGCA | GGGAGCTGGG | CTCTTCAAGA | CTCAGGACCG | 120 |
| AGGCAGATCT | CATGTTTTGG | GGTCTGGATT | TGTGTCAGCG | AGGGAAGAAC | AGGCGCCAAT | 180 |
| AACCAAAGAA | GGCTGAAGCA | AGGTACAGGA | CTCCATAGCA | GCTGCAAGTA | CAATAAACAG | 240 |
| TTTTAGCAGA | GCTGGAAATG | TTGGCAGGCA | AGACAGGCCG | ATCGCAGAGT | CGGGCTGCTG | 300 |
| GAGAGAGGGA | AATCTACAAG | CGACCTGACA | TTTGGTGCTC | TAGAGCATTC | TAAGGCTTGC | 360 |
| TGCTTGACTT | CTAAAGAAGC | TGAAATAATT | GAGGAGGAGC | GGGGACCCTC | TGTTTCCAAG | 420 |
| GACTCTGTTC | TGCAGAGAAT | GTTCTGCACC | CTCTGATACT | CCAGATCCAA | CTCCGTCTTC | 480 |

| | | | | | | | | | | | | | | | | |
|---|---|---|---|---|---|---|---|---|---|---|---|---|---|---|---|---|
| TGAA | ATG | ATC | CCG | ATT | CCC | AGA | ATG | CCC | CTG | GTG | CTG | CTC | CTG | CTC | TTG | 529 |
| | Met | Ile | Pro | Ile | Pro | Arg | Met | Pro | Leu | Val | Leu | Leu | Leu | Leu | Leu | |
| | 1 | | | | 5 | | | | | 10 | | | | | 15 | |
| CTC | ATC | CTG | GGT | TCT | GCA | AAA | GCT | CAG | GTT | AAT | CCA | GCC | ATA | TGC | CGC | 577 |
| Leu | Ile | Leu | Gly | Ser | Ala | Lys | Ala | Gln | Val | Asn | Pro | Ala | Ile | Cys | Arg | |
| | | | | 20 | | | | | 25 | | | | | 30 | | |
| TAT | CCT | CTG | GGC | ATG | TCA | GGA | GGC | CAC | ATT | CCA | GAT | GAG | GAC | ATC | ACA | 625 |
| Tyr | Pro | Leu | Gly | Met | Ser | Gly | Gly | His | Ile | Pro | Asp | Glu | Asp | Ile | Thr | |
| | | | 35 | | | | | 40 | | | | | 45 | | | |
| GCC | TCA | AGT | CAG | TGG | TCA | GAA | TCC | ACG | GCT | GCC | AAA | TAT | GGG | AGG | CTG | 673 |
| Ala | Ser | Ser | Gln | Trp | Ser | Glu | Ser | Thr | Ala | Ala | Lys | Tyr | Gly | Arg | Leu | |
| | | 50 | | | | | 55 | | | | | 60 | | | | |
| GAC | TCT | GAA | GAA | GGA | GAT | GGA | GCC | TGG | TGT | CCT | GAG | ATT | CCA | GTG | CAA | 721 |
| Asp | Ser | Glu | Glu | Gly | Asp | Gly | Ala | Trp | Cys | Pro | Glu | Ile | Pro | Val | Gln | |
| | 65 | | | | | 70 | | | | | 75 | | | | | |
| CCC | GAT | GAC | CTG | AAG | GAA | TTT | CTG | CAG | ATT | GAC | TTG | CGA | ACC | CTA | CAC | 769 |
| Pro | Asp | Asp | Leu | Lys | Glu | Phe | Leu | Gln | Ile | Asp | Leu | Arg | Thr | Leu | His | |
| 80 | | | | | 85 | | | | | 90 | | | | | 95 | |
| TTT | ATC | ACT | CTT | GTG | GGG | ACC | CAG | GGG | CGC | CAT | GCA | GGG | GGT | CAT | GGC | 817 |
| Phe | Ile | Thr | Leu | Val | Gly | Thr | Gln | Gly | Arg | His | Ala | Gly | Gly | His | Gly | |
| | | | | 100 | | | | | 105 | | | | | 110 | | |
| ATT | GAA | TTT | GCA | CCC | ATG | TAC | AAG | ATC | AAC | TAC | AGT | CGG | GAT | GGC | AGT | 865 |
| Ile | Glu | Phe | Ala | Pro | Met | Tyr | Lys | Ile | Asn | Tyr | Ser | Arg | Asp | Gly | Ser | |
| | | | 115 | | | | | 120 | | | | | 125 | | | |
| CGC | TGG | ATC | TCC | TGG | CGT | AAC | CGG | CAT | GGG | AAG | CAG | GTG | CTT | GAT | GGA | 913 |
| Arg | Trp | Ile | Ser | Trp | Arg | Asn | Arg | His | Gly | Lys | Gln | Val | Leu | Asp | Gly | |
| | | 130 | | | | | 135 | | | | | 140 | | | | |
| AAC | AGT | AAC | CCT | TAT | GAT | GTA | TTC | CTG | AAG | GAC | TTG | GAG | CCA | CCC | ATC | 961 |
| Asn | Ser | Asn | Pro | Tyr | Asp | Val | Phe | Leu | Lys | Asp | Leu | Glu | Pro | Pro | Ile | |
| | 145 | | | | | 150 | | | | | 155 | | | | | |
| GTC | GCC | AGA | TTT | GTT | CGC | CTT | ATC | CCA | GTC | ACT | GAC | CAC | TCC | ATG | AAC | 1009 |
| Val | Ala | Arg | Phe | Val | Arg | Leu | Ile | Pro | Val | Thr | Asp | His | Ser | Met | Asn | |
| 160 | | | | | 165 | | | | | 170 | | | | | 175 | |
| GTG | TGC | ATG | AGG | GTT | GAG | CTT | TAT | GGT | TGT | GTC | TGG | CTA | GAT | GGC | TTG | 1057 |
| Val | Cys | Met | Arg | Val | Glu | Leu | Tyr | Gly | Cys | Val | Trp | Leu | Asp | Gly | Leu | |
| | | | | 180 | | | | | 185 | | | | | 190 | | |
| GTA | TCC | TAC | AAT | GCT | CCA | GCT | GGA | CAG | CAG | TTT | GTA | CTC | CCT | GGA | GGC | 1105 |
| Val | Ser | Tyr | Asn | Ala | Pro | Ala | Gly | Gln | Gln | Phe | Val | Leu | Pro | Gly | Gly | |
| | | | 195 | | | | | 200 | | | | | 205 | | | |
| TCC | ATC | ATT | TAT | CTG | AAT | GAT | TCT | GTC | TAT | GAT | GGA | GCT | GTT | GGG | TAC | 1153 |
| Ser | Ile | Ile | Tyr | Leu | Asn | Asp | Ser | Val | Tyr | Asp | Gly | Ala | Val | Gly | Tyr | |
| | | 210 | | | | | 215 | | | | | 220 | | | | |
| AGC | ATG | ACT | GAA | GGG | CTA | GGC | CAG | TTG | ACT | GAT | GGA | GTA | TCC | GGC | CTG | 1201 |
| Ser | Met | Thr | Glu | Gly | Leu | Gly | Gln | Leu | Thr | Asp | Gly | Val | Ser | Gly | Leu | |
| | 225 | | | | | 230 | | | | | 235 | | | | | |
| GAT | GAT | TTT | ACC | CAG | ACC | CAT | GAA | TAC | CAC | GTG | TGG | CCT | GGC | TAT | GAC | 1249 |

-continued

| | | | | | | | | | | | | | | | |
|---|---|---|---|---|---|---|---|---|---|---|---|---|---|---|---|
| Asp | Asp | Phe | Thr | Gln | Thr | His | Glu | Tyr | His | Val | Trp | Pro | Gly | Tyr | Asp |
| 240 | | | | 245 | | | | | 250 | | | | | 255 | |

| TAC | GTG | GGA | TGG | CGG | AAC | GAA | AGT | GCT | ACC | AAC | GGT | TTC | ATT | GAG | ATC | 1297 |
|---|---|---|---|---|---|---|---|---|---|---|---|---|---|---|---|---|
| Tyr | Val | Gly | Trp | Arg | Asn | Glu | Ser | Ala | Thr | Asn | Gly | Phe | Ile | Glu | Ile | |
| | | | | 260 | | | | | 265 | | | | | 270 | | |

| ATG | TTT | GAA | TTT | GAC | CGA | ATC | AGG | AAT | TTT | ACT | ACC | ATG | AAG | GTC | CAC | 1345 |
|---|---|---|---|---|---|---|---|---|---|---|---|---|---|---|---|---|
| Met | Phe | Glu | Phe | Asp | Arg | Ile | Arg | Asn | Phe | Thr | Thr | Met | Lys | Val | His | |
| | | | 275 | | | | | 280 | | | | | 285 | | | |

| TGC | AAC | AAC | ATG | TTT | GCT | AAA | GGT | GTG | AAG | ATT | TTT | AAG | GAG | GTC | CAG | 1393 |
|---|---|---|---|---|---|---|---|---|---|---|---|---|---|---|---|---|
| Cys | Asn | Asn | Met | Phe | Ala | Lys | Gly | Val | Lys | Ile | Phe | Lys | Glu | Val | Gln | |
| | | 290 | | | | | 295 | | | | | 300 | | | | |

| TGC | TAC | TTT | CGC | TCG | GAA | GCC | AGC | GAG | TGG | GAA | CCC | ACT | GCT | GTC | TAC | 1441 |
|---|---|---|---|---|---|---|---|---|---|---|---|---|---|---|---|---|
| Cys | Tyr | Phe | Arg | Ser | Glu | Ala | Ser | Glu | Trp | Glu | Pro | Thr | Ala | Val | Tyr | |
| | 305 | | | | | 310 | | | | | 315 | | | | | |

| TTT | CCC | CTG | GTC | CTG | GAC | GAT | GTG | AAC | CCC | AGT | GCC | CGG | TTT | GTC | ACG | 1489 |
|---|---|---|---|---|---|---|---|---|---|---|---|---|---|---|---|---|
| Phe | Pro | Leu | Val | Leu | Asp | Asp | Val | Asn | Pro | Ser | Ala | Arg | Phe | Val | Thr | |
| 320 | | | | | 325 | | | | | 330 | | | | | 335 | |

| GTG | CCC | CTC | CAC | CAC | CGA | ATG | GCC | AGT | GCC | ATC | AAG | TGC | CAA | TAC | CAT | 1537 |
|---|---|---|---|---|---|---|---|---|---|---|---|---|---|---|---|---|
| Val | Pro | Leu | His | His | Arg | Met | Ala | Ser | Ala | Ile | Lys | Cys | Gln | Tyr | His | |
| | | | | 340 | | | | | 345 | | | | | 350 | | |

| TTT | GCC | GAC | ACG | TGG | ATG | ATG | TTC | AGC | GAG | ATC | ACT | TTC | CAA | TCA | GAT | 1585 |
|---|---|---|---|---|---|---|---|---|---|---|---|---|---|---|---|---|
| Phe | Ala | Asp | Thr | Trp | Met | Met | Phe | Ser | Glu | Ile | Thr | Phe | Gln | Ser | Asp | |
| | | | 355 | | | | | 360 | | | | | 365 | | | |

| GCT | GCA | ATG | TAT | AAC | AAC | TCT | GGA | GCC | CTT | CCC | ACC | TCT | CCT | ATG | GCA | 1633 |
|---|---|---|---|---|---|---|---|---|---|---|---|---|---|---|---|---|
| Ala | Ala | Met | Tyr | Asn | Asn | Ser | Gly | Ala | Leu | Pro | Thr | Ser | Pro | Met | Ala | |
| | | 370 | | | | | 375 | | | | | 380 | | | | |

| CCC | ACC | ACC | TAT | GAT | CCC | ATG | CTT | AAA | GTT | GAT | GAT | AGC | AAC | ACT | CGG | 1681 |
|---|---|---|---|---|---|---|---|---|---|---|---|---|---|---|---|---|
| Pro | Thr | Thr | Tyr | Asp | Pro | Met | Leu | Lys | Val | Asp | Asp | Ser | Asn | Thr | Arg | |
| | 385 | | | | | 390 | | | | | 395 | | | | | |

| ATC | CTG | ATT | GGT | TGC | TTG | GTG | GCC | ATC | ATC | TTC | ATC | CTG | CTG | GCT | ATC | 1729 |
|---|---|---|---|---|---|---|---|---|---|---|---|---|---|---|---|---|
| Ile | Leu | Ile | Gly | Cys | Leu | Val | Ala | Ile | Ile | Phe | Ile | Leu | Leu | Ala | Ile | |
| 400 | | | | | 405 | | | | | 410 | | | | | 415 | |

| ATC | GTC | ATC | ATC | CTG | TGG | AGG | CAG | TTC | TGG | CAG | AAG | ATG | CTA | GAA | AAG | 1777 |
|---|---|---|---|---|---|---|---|---|---|---|---|---|---|---|---|---|
| Ile | Val | Ile | Ile | Leu | Trp | Arg | Gln | Phe | Trp | Gln | Lys | Met | Leu | Glu | Lys | |
| | | | | 420 | | | | | 425 | | | | | 430 | | |

| GCT | TCA | CGG | AGG | ATG | CTG | GAT | GAT | GAA | ATG | ACA | GTC | AGC | CTT | TCC | CTG | 1825 |
|---|---|---|---|---|---|---|---|---|---|---|---|---|---|---|---|---|
| Ala | Ser | Arg | Arg | Met | Leu | Asp | Asp | Glu | Met | Thr | Val | Ser | Leu | Ser | Leu | |
| | | 435 | | | | | 440 | | | | | 445 | | | | |

| CCC | AGC | GAG | TCC | AGC | ATG | TTC | AAT | AAC | AAC | CGC | TCC | TCA | TCA | CCA | AGT | 1873 |
|---|---|---|---|---|---|---|---|---|---|---|---|---|---|---|---|---|
| Pro | Ser | Glu | Ser | Ser | Met | Phe | Asn | Asn | Asn | Arg | Ser | Ser | Ser | Pro | Ser | |
| | | 450 | | | | | 455 | | | | | 460 | | | | |

| GAA | CAG | GAG | TCC | AAC | TCT | ACT | TAT | GAT | CGA | ATC | TTC | CCC | CTT | CGC | CCT | 1921 |
|---|---|---|---|---|---|---|---|---|---|---|---|---|---|---|---|---|
| Glu | Gln | Glu | Ser | Asn | Ser | Thr | Tyr | Asp | Arg | Ile | Phe | Pro | Leu | Arg | Pro | |
| | 465 | | | | | 470 | | | | | 475 | | | | | |

| GAC | TAC | CAG | GAG | CCA | TCC | AGA | CTG | ATC | CGA | AAG | CTT | CCA | GAG | TTT | GCT | 1969 |
|---|---|---|---|---|---|---|---|---|---|---|---|---|---|---|---|---|
| Asp | Tyr | Gln | Glu | Pro | Ser | Arg | Leu | Ile | Arg | Lys | Leu | Pro | Glu | Phe | Ala | |
| 480 | | | | | 485 | | | | | 490 | | | | | 495 | |

| CCA | GGA | GAG | GAG | GAG | TCA | GGG | TGC | AGT | GGT | GTT | GTG | AAG | CCG | GCC | CAG | 2017 |
|---|---|---|---|---|---|---|---|---|---|---|---|---|---|---|---|---|
| Pro | Gly | Glu | Glu | Glu | Ser | Gly | Cys | Ser | Gly | Val | Val | Lys | Pro | Ala | Gln | |
| | | | | 500 | | | | | 505 | | | | | 510 | | |

| CCC | AAT | GGA | CCT | GAG | GGC | GTG | CCC | CAC | TAT | GCA | GAA | GCC | GAC | ATA | GTG | 2065 |
|---|---|---|---|---|---|---|---|---|---|---|---|---|---|---|---|---|
| Pro | Asn | Gly | Pro | Glu | Gly | Val | Pro | His | Tyr | Ala | Glu | Ala | Asp | Ile | Val | |
| | | | 515 | | | | | 520 | | | | | 525 | | | |

| AAT | CTC | CAG | GGA | GTG | ACA | GGT | GGC | AAC | ACC | TAC | TGT | GTG | CCT | GCT | GTA | 2113 |
|---|---|---|---|---|---|---|---|---|---|---|---|---|---|---|---|---|
| Asn | Leu | Gln | Gly | Val | Thr | Gly | Gly | Asn | Thr | Tyr | Cys | Val | Pro | Ala | Val | |
| | | 530 | | | | | 535 | | | | | 540 | | | | |

| ACC | ATG | GAT | CTG | CTA | TCG | GGG | AAA | GAT | GTG | GCT | GTG | GAA | GAG | TTC | CCC | 2161 |
|---|---|---|---|---|---|---|---|---|---|---|---|---|---|---|---|---|
| Thr | Met | Asp | Leu | Leu | Ser | Gly | Lys | Asp | Val | Ala | Val | Glu | Glu | Phe | Pro | |
| | 545 | | | | | 550 | | | | | 555 | | | | | |

| AGG | AAA | CTG | TTG | GCC | TTC | AAG | GAG | AAG | CTG | GGA | GAA | GGC | CAG | TTT | GGG | 2209 |

| | | | | | | | | | | | | | | | |
|---|---|---|---|---|---|---|---|---|---|---|---|---|---|---|---|
| Arg | Lys | Leu | Leu | Ala | Phe | Lys | Glu | Lys | Leu | Gly | Glu | Gly | Gln | Phe | Gly |
| 560 | | | | | 565 | | | | 570 | | | | | 575 | |

```
GAG  GTT  CAT  CTC  TGT  GAA  GTG  GAG  GGA  ATG  GAA  AAA  TTC  AAA  GAC  AAA      2257
Glu  Val  His  Leu  Cys  Glu  Val  Glu  Gly  Met  Glu  Lys  Phe  Lys  Asp  Lys
                         580                585                          590

GAT  TTT  GCA  CTA  GAT  GTC  AGT  GCC  AAC  CAG  CCT  GTC  CTG  GTG  GCC  GTG      2305
Asp  Phe  Ala  Leu  Asp  Val  Ser  Ala  Asn  Gln  Pro  Val  Leu  Val  Ala  Val
                    595                      600                605

AAA  ATG  CTC  CGA  GCA  GAT  GCC  AAC  AAG  AAT  GCC  AGG  AAT  GAT  TTT  CTT      2353
Lys  Met  Leu  Arg  Ala  Asp  Ala  Asn  Lys  Asn  Ala  Arg  Asn  Asp  Phe  Leu
               610                      615                     620

AAG  GAG  ATC  AAG  ATC  ATG  TCT  CGG  CTC  AAG  GAC  CCA  AAC  ATC  ATC  CGT      2401
Lys  Glu  Ile  Lys  Ile  Met  Ser  Arg  Leu  Lys  Asp  Pro  Asn  Ile  Ile  Arg
          625                      630                     635

CTC  TTA  GCT  GTG  TGC  ATC  ACT  GAG  GAC  CCG  CTC  TGC  ATG  ATC  ACG  GAA      2449
Leu  Leu  Ala  Val  Cys  Ile  Thr  Glu  Asp  Pro  Leu  Cys  Met  Ile  Thr  Glu
640                      645                     650                          655

TAC  ATG  GAG  AAT  GGA  GAT  CTT  AAT  CAG  TTT  CTT  TCT  CGC  CAC  GAG  CCT      2497
Tyr  Met  Glu  Asn  Gly  Asp  Leu  Asn  Gln  Phe  Leu  Ser  Arg  His  Glu  Pro
                    660                     665                          670

CTG  AGT  TCC  TGT  TCT  AGT  GAT  GCC  ACA  GTC  AGT  TAC  GCC  AAC  CTG  AAG      2545
Leu  Ser  Ser  Cys  Ser  Ser  Asp  Ala  Thr  Val  Ser  Tyr  Ala  Asn  Leu  Lys
               675                      680                     685

TTT  ATG  GCA  ACC  CAG  ATT  GCC  TCT  GGT  ATG  AAG  TAC  CTT  TCG  TCT  CTC      2593
Phe  Met  Ala  Thr  Gln  Ile  Ala  Ser  Gly  Met  Lys  Tyr  Leu  Ser  Ser  Leu
               690                      695                     700

AAC  TTT  GTC  CAC  CGA  GAT  CTG  GCC  ACA  CGA  AAC  TGT  TTA  GTG  GGC  AAG      2641
Asn  Phe  Val  His  Arg  Asp  Leu  Ala  Thr  Arg  Asn  Cys  Leu  Val  Gly  Lys
     705                      710                     715

AAT  TAC  ACC  ATC  AAG  ATA  GCT  GAT  TTT  GGC  ATG  AGC  AGA  AAC  CTG  TAC      2689
Asn  Tyr  Thr  Ile  Lys  Ile  Ala  Asp  Phe  Gly  Met  Ser  Arg  Asn  Leu  Tyr
720                      725                     730                          735

AGT  GGT  GAT  TAC  TAC  CGG  ATC  CAG  GGC  CGG  GCG  GTG  CTC  CCC  ATT  CGC      2737
Ser  Gly  Asp  Tyr  Tyr  Arg  Ile  Gln  Gly  Arg  Ala  Val  Leu  Pro  Ile  Arg
                    740                     745                          750

TGG  ATG  TCC  TGG  GAA  AGC  ATC  TTG  CTG  GGC  AAA  TTC  ACC  ACG  GCA  AGT      2785
Trp  Met  Ser  Trp  Glu  Ser  Ile  Leu  Leu  Gly  Lys  Phe  Thr  Thr  Ala  Ser
               755                      760                     765

GAT  GTG  TGG  GCC  TTT  GGG  GTG  ACT  CTG  TGG  GAG  ACC  TTC  ACC  TTT  TGC      2833
Asp  Val  Trp  Ala  Phe  Gly  Val  Thr  Leu  Trp  Glu  Thr  Phe  Thr  Phe  Cys
          770                      775                     780

CAG  GAG  CAG  CCC  TAT  TCC  CAG  CTG  TCG  GAT  GAG  CAG  GTT  ATC  GAG  AAC      2881
Gln  Glu  Gln  Pro  Tyr  Ser  Gln  Leu  Ser  Asp  Glu  Gln  Val  Ile  Glu  Asn
     785                      790                     795

ACT  GGA  GAG  TTC  TTC  CGA  GAC  CAA  GGG  AGG  CAG  ATC  TAT  CTC  CCT  CAA      2929
Thr  Gly  Glu  Phe  Phe  Arg  Asp  Gln  Gly  Arg  Gln  Ile  Tyr  Leu  Pro  Gln
800                      805                     810                          815

CCA  GCC  CTT  TGC  CCC  GAC  TCT  GTG  TAT  AAG  CTG  ATG  CTC  AGC  TGC  TGG      2977
Pro  Ala  Leu  Cys  Pro  Asp  Ser  Val  Tyr  Lys  Leu  Met  Leu  Ser  Cys  Trp
               820                      825                     830

AGA  AGA  GAA  ACC  AAG  CAC  CGG  CCA  TCC  TTC  CAG  GAA  ATA  CAC  CTC  CTG      3025
Arg  Arg  Glu  Thr  Lys  His  Arg  Pro  Ser  Phe  Gln  Glu  Ile  His  Leu  Leu
               835                      840                     845

CTT  CTT  CAG  CAA  GGA  GCC  GAG  T  GATGATGCAT  CAGCACCTGG  CAGTGTTCCT           3077
Leu  Leu  Gln  Gln  Gly  Ala  Glu
                         850

GTGGCCCAGA  TCCTTCCCAC  AAGACCTACT  GCTCACCCAC  ATC                                3120
```

( 2 ) INFORMATION FOR SEQ ID NO:20:

( i ) SEQUENCE CHARACTERISTICS:
   ( A ) LENGTH: 854 amino acids
   ( B ) TYPE: amino acid
   ( D ) TOPOLOGY: linear ( i i ) MOLECULE TYPE: protein ( x i ) SEQUENCE DESCRIPTION: SEQ ID NO:20:

```
Met  Ile  Pro  Ile  Pro  Arg  Met  Pro  Leu  Val  Leu  Leu  Leu  Leu  Leu
 1                  5                        10                       15

Ile  Leu  Gly  Ser  Ala  Lys  Ala  Gln  Val  Asn  Pro  Ala  Ile  Cys  Arg  Tyr
              20                        25                        30

Pro  Leu  Gly  Met  Ser  Gly  Gly  His  Ile  Pro  Asp  Glu  Asp  Ile  Thr  Ala
              35                        40                        45

Ser  Ser  Gln  Trp  Ser  Glu  Ser  Thr  Ala  Ala  Lys  Tyr  Gly  Arg  Leu  Asp
 50                       55                        60

Ser  Glu  Glu  Gly  Asp  Gly  Ala  Trp  Cys  Pro  Glu  Ile  Pro  Val  Gln  Pro
 65                       70                        75                       80

Asp  Asp  Leu  Lys  Glu  Phe  Leu  Gln  Ile  Asp  Leu  Arg  Thr  Leu  His  Phe
                    85                        90                        95

Ile  Thr  Leu  Val  Gly  Thr  Gln  Gly  Arg  His  Ala  Gly  Gly  His  Gly  Ile
              100                       105                       110

Glu  Phe  Ala  Pro  Met  Tyr  Lys  Ile  Asn  Tyr  Ser  Arg  Asp  Gly  Ser  Arg
          115                       120                       125

Trp  Ile  Ser  Trp  Arg  Asn  Arg  His  Gly  Lys  Gln  Val  Leu  Asp  Gly  Asn
     130                      135                       140

Ser  Asn  Pro  Tyr  Asp  Val  Phe  Leu  Lys  Asp  Leu  Glu  Pro  Pro  Ile  Val
145                       150                       155                      160

Ala  Arg  Phe  Val  Arg  Leu  Ile  Pro  Val  Thr  Asp  His  Ser  Met  Asn  Val
                    165                       170                       175

Cys  Met  Arg  Val  Glu  Leu  Tyr  Gly  Cys  Val  Trp  Leu  Asp  Gly  Leu  Val
               180                      185                       190

Ser  Tyr  Asn  Ala  Pro  Ala  Gly  Gln  Gln  Phe  Val  Leu  Pro  Gly  Gly  Ser
          195                       200                       205

Ile  Ile  Tyr  Leu  Asn  Asp  Ser  Val  Tyr  Asp  Gly  Ala  Val  Gly  Tyr  Ser
     210                      215                       220

Met  Thr  Glu  Gly  Leu  Gly  Gln  Leu  Thr  Asp  Gly  Val  Ser  Gly  Leu  Asp
225                       230                       235                      240

Asp  Phe  Thr  Gln  Thr  His  Glu  Tyr  His  Val  Trp  Pro  Gly  Tyr  Asp  Tyr
               245                       250                       255

Val  Gly  Trp  Arg  Asn  Glu  Ser  Ala  Thr  Asn  Gly  Phe  Ile  Glu  Ile  Met
               260                       265                       270

Phe  Glu  Phe  Asp  Arg  Ile  Arg  Asn  Phe  Thr  Thr  Met  Lys  Val  His  Cys
          275                       280                       285

Asn  Asn  Met  Phe  Ala  Lys  Gly  Val  Lys  Ile  Phe  Lys  Glu  Val  Gln  Cys
     290                       295                       300

Tyr  Phe  Arg  Ser  Glu  Ala  Ser  Glu  Trp  Glu  Pro  Thr  Ala  Val  Tyr  Phe
305                       310                       315                      320

Pro  Leu  Val  Leu  Asp  Asp  Val  Asn  Pro  Ser  Ala  Arg  Phe  Val  Thr  Val
                    325                       330                       335

Pro  Leu  His  His  Arg  Met  Ala  Ser  Ala  Ile  Lys  Cys  Gln  Tyr  His  Phe
               340                       345                       350

Ala  Asp  Thr  Trp  Met  Met  Phe  Ser  Glu  Ile  Thr  Phe  Gln  Ser  Asp  Ala
          355                       360                       365

Ala  Met  Tyr  Asn  Asn  Ser  Gly  Ala  Leu  Pro  Thr  Ser  Pro  Met  Ala  Pro
     370                       375                       380
```

```
Thr Thr Tyr Asp Pro Met Leu Lys Val Asp Asp Ser Asn Thr Arg Ile
385                 390                 395                 400

Leu Ile Gly Cys Leu Val Ala Ile Ile Phe Ile Leu Leu Ala Ile Ile
            405                 410                 415

Val Ile Ile Leu Trp Arg Gln Phe Trp Gln Lys Met Leu Glu Lys Ala
            420                 425                 430

Ser Arg Arg Met Leu Asp Asp Glu Met Thr Val Ser Leu Ser Leu Pro
        435                 440                 445

Ser Glu Ser Ser Met Phe Asn Asn Asn Arg Ser Ser Ser Pro Ser Glu
    450                 455                 460

Gln Glu Ser Asn Ser Thr Tyr Asp Arg Ile Phe Pro Leu Arg Pro Asp
465                 470                 475                 480

Tyr Gln Glu Pro Ser Arg Leu Ile Arg Lys Leu Pro Glu Phe Ala Pro
                485                 490                 495

Gly Glu Glu Glu Ser Gly Cys Ser Gly Val Val Lys Pro Ala Gln Pro
                500                 505                 510

Asn Gly Pro Glu Gly Val Pro His Tyr Ala Glu Ala Asp Ile Val Asn
            515                 520                 525

Leu Gln Gly Val Thr Gly Gly Asn Thr Tyr Cys Val Pro Ala Val Thr
    530                 535                 540

Met Asp Leu Leu Ser Gly Lys Asp Val Ala Val Glu Glu Phe Pro Arg
545                 550                 555                 560

Lys Leu Leu Ala Phe Lys Glu Lys Leu Gly Glu Gly Gln Phe Gly Glu
                565                 570                 575

Val His Leu Cys Glu Val Glu Gly Met Glu Lys Phe Lys Asp Lys Asp
            580                 585                 590

Phe Ala Leu Asp Val Ser Ala Asn Gln Pro Val Leu Val Ala Val Lys
        595                 600                 605

Met Leu Arg Ala Asp Ala Asn Lys Asn Ala Arg Asn Asp Phe Leu Lys
    610                 615                 620

Glu Ile Lys Ile Met Ser Arg Leu Lys Asp Pro Asn Ile Ile Arg Leu
625                 630                 635                 640

Leu Ala Val Cys Ile Thr Glu Asp Pro Leu Cys Met Ile Thr Glu Tyr
            645                 650                 655

Met Glu Asn Gly Asp Leu Asn Gln Phe Leu Ser Arg His Glu Pro Leu
            660                 665                 670

Ser Ser Cys Ser Ser Asp Ala Thr Val Ser Tyr Ala Asn Leu Lys Phe
        675                 680                 685

Met Ala Thr Gln Ile Ala Ser Gly Met Lys Tyr Leu Ser Ser Leu Asn
    690                 695                 700

Phe Val His Arg Asp Leu Ala Thr Arg Asn Cys Leu Val Gly Lys Asn
705                 710                 715                 720

Tyr Thr Ile Lys Ile Ala Asp Phe Gly Met Ser Arg Asn Leu Tyr Ser
                725                 730                 735

Gly Asp Tyr Tyr Arg Ile Gln Gly Arg Ala Val Leu Pro Ile Arg Trp
                740                 745                 750

Met Ser Trp Glu Ser Ile Leu Leu Gly Lys Phe Thr Thr Ala Ser Asp
            755                 760                 765

Val Trp Ala Phe Gly Val Thr Leu Trp Glu Thr Phe Thr Phe Cys Gln
    770                 775                 780

Glu Gln Pro Tyr Ser Gln Leu Ser Asp Glu Gln Val Ile Glu Asn Thr
785                 790                 795                 800

Gly Glu Phe Phe Arg Asp Gln Gly Arg Gln Ile Tyr Leu Pro Gln Pro
```

```
                                  805                          810                          815
Ala  Leu  Cys  Pro  Asp  Ser  Val  Tyr  Lys  Leu  Met  Leu  Ser  Cys  Trp  Arg
               820                      825                          830

Arg  Glu  Thr  Lys  His  Arg  Pro  Ser  Phe  Gln  Glu  Ile  His  Leu  Leu  Leu
               835                      840                          845

Leu  Gln  Gln  Gly  Ala  Glu
          850
```

( 2 ) INFORMATION FOR SEQ ID NO:21:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE:
        ( B ) CLONE: Tyro-11

( i x ) FEATURE:
        ( A ) NAME/KEY: CDS
        ( B ) LOCATION: 1..171

( x i ) SEQUENCE DESCRIPTION: SEQ ID NO:21:

```
AAC  ATC  CTG  GTC  AAC  AGT  AAC  CTG  GTC  TGC  AAG  GTG  TCC  GAC  TTT  GGC        48
Asn  Ile  Leu  Val  Asn  Ser  Asn  Leu  Val  Cys  Lys  Val  Ser  Asp  Phe  Gly
 1                        5                        10                       15

CTC  TCC  AGA  TTC  CTG  GAG  GAG  AAC  TCC  TCT  GAT  CCC  ACC  TAC  ACA  AGT        96
Leu  Ser  Arg  Phe  Leu  Glu  Glu  Asn  Ser  Ser  Asp  Pro  Thr  Tyr  Thr  Ser
               20                       25                       30

TCC  CTG  GGA  GGA  AAG  ATT  CCC  ATC  CGA  TGG  ACC  GCC  CCT  GAG  GCC  ATT       144
Ser  Leu  Gly  Gly  Lys  Ile  Pro  Ile  Arg  Trp  Thr  Ala  Pro  Glu  Ala  Ile
               35                       40                       45

GCC  TTC  AGG  AAA  TTC  ACG  TCT  GCC  AGT                                          171
Ala  Phe  Arg  Lys  Phe  Thr  Ser  Ala  Ser
          50                       55
```

( 2 ) INFORMATION FOR SEQ ID NO:22:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Asn  Ile  Leu  Val  Asn  Ser  Asn  Leu  Val  Cys  Lys  Val  Ser  Asp  Phe  Gly
 1                        5                        10                       15

Leu  Ser  Arg  Phe  Leu  Glu  Glu  Asn  Ser  Ser  Asp  Pro  Thr  Tyr  Thr  Ser
               20                       25                       30

Ser  Leu  Gly  Gly  Lys  Ile  Pro  Ile  Arg  Trp  Thr  Ala  Pro  Glu  Ala  Ile
               35                       40                       45

Ala  Phe  Arg  Lys  Phe  Thr  Ser  Ala  Ser
          50                       55
```

( 2 ) INFORMATION FOR SEQ ID NO:23:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear (i i) MOLECULE TYPE: DNA (v i i) IMMEDIATE SOURCE:
 (B) CLONE: Tyro-12

(i x) FEATURE:
 (A) NAME/KEY: CDS
 (B) LOCATION: 1..162

(x i) SEQUENCE DESCRIPTION: SEQ ID NO:23:

```
AAT  TGC  ATG  TTG  CGG  GAT  GAC  ATG  ACT  GTC  TGC  GTG  GCA  GAC  TTT  GGC      48
Asn  Cys  Met  Leu  Arg  Asp  Asp  Met  Thr  Val  Cys  Val  Ala  Asp  Phe  Gly
 1              5                        10                       15

CTC  TCT  AAG  AAG  ATT  TAC  AGT  GGT  GAT  TAT  TAC  CGC  CAA  GGC  CGC  ATT      96
Leu  Ser  Lys  Lys  Ile  Tyr  Ser  Gly  Asp  Tyr  Tyr  Arg  Gln  Gly  Arg  Ile
               20                       25                       30

GCC  AAA  ATG  CCT  GTG  AAG  TGG  ATC  GCC  ATA  GAG  AGC  CTG  GCG  GAC  CGA     144
Ala  Lys  Met  Pro  Val  Lys  Trp  Ile  Ala  Ile  Glu  Ser  Leu  Ala  Asp  Arg
          35                       40                       45

GTC  TAC  ACA  AGC  AAG  AGT                                                        162
Val  Tyr  Thr  Ser  Lys  Ser
 50
```

(2) INFORMATION FOR SEQ ID NO:24:

(i) SEQUENCE CHARACTERISTICS:
  (A) LENGTH: 54 amino acids
  (B) TYPE: amino acid
  (D) TOPOLOGY: linear (i i) MOLECULE TYPE: protein (x i) SEQUENCE DESCRIPTION: SEQ ID NO:24:

```
Asn  Cys  Met  Leu  Arg  Asp  Asp  Met  Thr  Val  Cys  Val  Ala  Asp  Phe  Gly
 1              5                        10                       15

Leu  Ser  Lys  Lys  Ile  Tyr  Ser  Gly  Asp  Tyr  Tyr  Arg  Gln  Gly  Arg  Ile
               20                       25                       30

Ala  Lys  Met  Pro  Val  Lys  Trp  Ile  Ala  Ile  Glu  Ser  Leu  Ala  Asp  Arg
          35                       40                       45

Val  Tyr  Thr  Ser  Lys  Ser
 50
```

(2) INFORMATION FOR SEQ ID NO:25:

(i) SEQUENCE CHARACTERISTICS:
  (A) LENGTH: 147 base pairs
  (B) TYPE: nucleic acid
  (C) STRANDEDNESS: single
  (D) TOPOLOGY: linear (i i) MOLECULE TYPE: DNA (v i i) IMMEDIATE SOURCE:
  (B) CLONE: Tyro-13

(i x) FEATURE:
  (A) NAME/KEY: CDS
  (B) LOCATION: 1..147

(x i) SEQUENCE DESCRIPTION: SEQ ID NO:25:

```
AAT  GTG  CTG  GTG  TCT  GAG  GAC  AAC  GTG  GCC  AAA  GTC  AGT  GAC  TTT  GGC      48
Asn  Val  Leu  Val  Ser  Glu  Asp  Asn  Val  Ala  Lys  Val  Ser  Asp  Phe  Gly
 1              5                        10                       15

CTC  ACT  AAG  GAA  GCT  TCC  AGC  ACT  CAG  GAC  ACA  GGC  AAA  CTG  CCA  GTC      96
Leu  Thr  Lys  Glu  Ala  Ser  Ser  Thr  Gln  Asp  Thr  Gly  Lys  Leu  Pro  Val
               20                       25                       30

AAG  TGG  ACA  GCT  CCT  GAA  GCC  TTG  AGA  GAG  AAG  AAA  TTT  TCC  ACC  AAG     144
```

```
Lys Trp Thr Ala Pro Glu Ala Leu Arg Glu Lys Lys Phe Ser Thr Lys
          35                      40                      45

TCT                                                                                        147
Ser
```

( 2 ) INFORMATION FOR SEQ ID NO:26:

( i ) SEQUENCE CHARACTERISTICS:
        ( A ) LENGTH: 49 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Asn Val Leu Val Ser Glu Asp Asn Val Ala Lys Val Ser Asp Phe Gly
 1               5                  10                      15

Leu Thr Lys Glu Ala Ser Ser Thr Gln Asp Thr Gly Lys Leu Pro Val
              20                  25                      30

Lys Trp Thr Ala Pro Glu Ala Leu Arg Glu Lys Lys Phe Ser Thr Lys
          35                      40                      45

Ser
```

( 2 ) INFORMATION FOR SEQ ID NO:27:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:27:

```
His Arg Asp Leu Ala Ala Arg
 1               5
```

( 2 ) INFORMATION FOR SEQ ID NO:28:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:28:

```
Asp Val Trp Ser Xaa Gly Xaa
 1               5
```

( 2 ) INFORMATION FOR SEQ ID NO:29:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:29:

```
Pro Xaa Xaa Trp Xaa Ala Pro Glu
 1               5
```

( 2 ) INFORMATION FOR SEQ ID NO:30:

( i ) SEQUENCE CHARACTERISTICS:
  ( A ) LENGTH: 68 amino acids
  ( B ) TYPE: amino acid
  ( C ) STRANDEDNESS: Not Relevant
  ( D ) TOPOLOGY: linear ( i i ) MOLECULE TYPE: protein ( x i ) SEQUENCE DESCRIPTION: SEQ ID NO:30:

| His | Arg | Asp | Leu | Ala | Ala | Arg | Asn | Val | Leu | Val | Lys | Thr | Pro | Gln | His |
|---|---|---|---|---|---|---|---|---|---|---|---|---|---|---|---|
| 1 | | | | 5 | | | | | 10 | | | | | 15 | |

| Val | Lys | Ile | Thr | Asp | Phe | Gly | Leu | Ala | Asp | Leu | Leu | Gly | Ala | Glu | Glu |
|---|---|---|---|---|---|---|---|---|---|---|---|---|---|---|---|
| | | | 20 | | | | | 25 | | | | | 30 | | |

| Lys | Glu | Tyr | His | Ala | Glu | Gly | Gly | Lys | Val | Pro | Ile | Lys | Trp | Met | Ala |
|---|---|---|---|---|---|---|---|---|---|---|---|---|---|---|---|
| | | 35 | | | | | 40 | | | | | 45 | | | |

| Leu | Glu | Ser | Ile | Leu | His | Arg | Ile | Tyr | Thr | His | Gln | Ser | Asp | Val | Trp |
|---|---|---|---|---|---|---|---|---|---|---|---|---|---|---|---|
| | 50 | | | | | 55 | | | | | 60 | | | | |

| Ser | Tyr | Gly | Val |
|---|---|---|---|
| 65 | | | |

( 2 ) INFORMATION FOR SEQ ID NO:31:

( i ) SEQUENCE CHARACTERISTICS:
    ( A ) LENGTH: 68 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:31:

| His | Arg | Asp | Leu | Ala | Ala | Arg | Asn | Cys | Met | Val | Ala | His | Asp | Phe | Thr |
|---|---|---|---|---|---|---|---|---|---|---|---|---|---|---|---|
| 1 | | | | 5 | | | | | 10 | | | | | 15 | |

| Val | Lys | Ile | Gly | Asp | Phe | Gly | Met | Thr | Arg | Asp | Ile | Tyr | Glu | Thr | Asp |
|---|---|---|---|---|---|---|---|---|---|---|---|---|---|---|---|
| | | | 20 | | | | | 25 | | | | | 30 | | |

| Tyr | Tyr | Arg | Lys | Gly | Gly | Lys | Gly | Leu | Leu | Pro | Val | Arg | Trp | Met | Ala |
|---|---|---|---|---|---|---|---|---|---|---|---|---|---|---|---|
| | | 35 | | | | | 40 | | | | | 45 | | | |

| Pro | Glu | Ser | Leu | Lys | Asp | Gly | Val | Phe | Thr | Thr | Ser | Ser | Asp | Met | Trp |
|---|---|---|---|---|---|---|---|---|---|---|---|---|---|---|---|
| | 50 | | | | | 55 | | | | | 60 | | | | |

| Ser | Phe | Gly | Val |
|---|---|---|---|
| 65 | | | |

( 2 ) INFORMATION FOR SEQ ID NO:32:

( i ) SEQUENCE CHARACTERISTICS:
    ( A ) LENGTH: 68 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:32:

| His | Arg | Asp | Leu | Ala | Ala | Arg | Asn | Val | Leu | Ile | Cys | Glu | Gly | Lys | Leu |
|---|---|---|---|---|---|---|---|---|---|---|---|---|---|---|---|
| 1 | | | | 5 | | | | | 10 | | | | | 15 | |

| Val | Lys | Ile | Cys | Asp | Phe | His | Leu | Ala | Arg | Asp | Ile | Met | Arg | Asp | Ser |
|---|---|---|---|---|---|---|---|---|---|---|---|---|---|---|---|
| | | | 20 | | | | | 25 | | | | | 30 | | |

| Asn | Tyr | Ile | Ser | Lys | Gly | Ser | Thr | Tyr | Leu | Pro | Leu | Lys | Trp | Met | Ala |
|---|---|---|---|---|---|---|---|---|---|---|---|---|---|---|---|
| | | 35 | | | | | 40 | | | | | 45 | | | |

| Pro | Glu | Ser | Ile | Phe | Asn | Ser | Leu | Tyr | Thr | Thr | Leu | Ser | Asp | Val | Trp |
|---|---|---|---|---|---|---|---|---|---|---|---|---|---|---|---|
| | 50 | | | | | 55 | | | | | 60 | | | | |

| Ser | Phe | Gly | Ile |
|---|---|---|---|
| 65 | | | |

( 2 ) INFORMATION FOR SEQ ID NO:33:

( i ) SEQUENCE CHARACTERISTICS:
        ( A ) LENGTH: 68 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:33:

```
His Arg Asp Leu Ala Ala Arg Asn Val Leu Ile Cys Glu Gly Lys Leu
 1               5                  10                  15
Val Lys Ile Cys Asp Phe Gly Leu Ala Arg Asp Ile Met Arg Asp Ser
             20                  25                  30
Asn Tyr Ile Ile Asp Gly Ser Thr Tyr Leu Pro Leu Lys Trp Met Ala
         35                  40                  45
Pro Glu Ser Ile Phe Asn Ser Leu Tyr Thr Thr Leu Ser Asp Val Trp
     50                  55                  60
Ser Phe Gly Ile
 65
```

( 2 ) INFORMATION FOR SEQ ID NO:34:

( i ) SEQUENCE CHARACTERISTICS:
        ( A ) LENGTH: 43 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:34:

```
His Arg Asp Leu Ala Ala Arg Asn Val Leu Val Val Lys Ile Asp Phe
 1               5                  10                  15
Gly Leu Ala Arg Asp Ile Tyr Gly Leu Pro Lys Trp Met Ala Pro Glu
             20                  25                  30
Ser Tyr Thr Ser Asp Val Trp Ser Phe Gly Val
         35                  40
```

( 2 ) INFORMATION FOR SEQ ID NO:35:

( i ) SEQUENCE CHARACTERISTICS:
        ( A ) LENGTH: 27 base pairs
        ( B ) TYPE: nucleic acid
        ( C ) STRANDEDNESS: Not Relevant
        ( D ) TOPOLOGY: linear ( i i ) MOLECULE TYPE:

( x i ) SEQUENCE DESCRIPTION: SEQ ID NO:35:

```
GGAATTCCAT CGNGATTTNG CNGCNCG                                27
```

( 2 ) INFORMATION FOR SEQ ID NO:36:

( i ) SEQUENCE CHARACTERISTICS:
        ( A ) LENGTH: 55 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:36:

```
Asn Cys Leu Val Gly Glu Asn Ile Ile Leu Val Lys Val Ala Asp Phe
```

```
  1               5                         10                        15
Gly Leu Ser Arg Leu Met Thr Gly Asp Thr Tyr Thr Ala Ile Ile Ala
            20                      25                      30
Gly Ala Lys Phe Pro Ile Lys Trp Thr Ala Pro Glu Ser Leu Ala Tyr
            35                      40                      45
Asn Lys Phe Ser Ile Lys Ser
            50              55
```

( 2 ) INFORMATION FOR SEQ ID NO:37:

( i ) SEQUENCE CHARACTERISTICS:
    ( A ) LENGTH: 55 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:37:

```
Asn Cys Leu Val Gly Glu Asn Ile Ile Val Lys Val Ala Asp Phe
1               5                       10                      15
Gly Leu Ser Arg Leu Met Thr Gly Asp Thr Tyr Thr Ala Ile Ile Ala
            20                      25                      30
Gly Ala Lys Phe Pro Ile Lys Trp Thr Ala Pro Glu Ser Leu Ala Tyr
            35                      40                      45
Asn Thr Pro Ser Ile Lys Ser
            50              55
```

( 2 ) INFORMATION FOR SEQ ID NO:38:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:38:

```
Asn Cys Leu Val Thr Glu Lys Asn Val Leu Lys Ile Ser Asp Phe Gly
1               5                       10                      15
His Ser Arg Glu Glu Ala Asp Gly Val Tyr Ala Ala Ser Gly Gly Leu
            20                      25                      30
Arg Gln Val Pro Val Lys Trp Thr Ala Pro Glu Ala Leu Asn Tyr Gly
            35                      40                      45
Arg Tyr Ser Ser Glu Ser
            50
```

( 2 ) INFORMATION FOR SEQ ID NO:39:

( i ) SEQUENCE CHARACTERISTICS:
    ( A ) LENGTH: 53 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:39:

```
Asn Cys Leu Val Gly Glu Asn Asn Thr Leu Lys Ile Ser Asp Phe Gly
1               5                       10                      15
Met Ser Arg Gln Glu Asp Gly Gly Val Tyr Ser Ser Ser Gly Leu Lys
            20                      25                      30
```

```
            Gln  Ile  Pro  Ile  Lys  Trp  Thr  Ala  Pro  Glu  Ala  Leu  His  Tyr  Gly  Arg
                      35                      40                      45

Tyr  Ser  Ser  Glu  Ser
                      50
```

( 2 ) INFORMATION FOR SEQ ID NO:40:

( i ) SEQUENCE CHARACTERISTICS:
        ( A ) LENGTH: 53 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:40:

```
            Asn  Cys  Leu  Val  Gly  Ser  Glu  Asn  Val  Val  Lys  Val  Ala  Asp  Phe  Gly
            1                  5                      10                      15

Leu  Ala  Arg  Tyr  Val  Leu  Asp  Asp  Gln  Tyr  Thr  Ser  Ser  Gly  Gly  Thr
                           20                      25                      30

Lys  Phe  Pro  Ile  Lys  Trp  Ala  Pro  Pro  Glu  Val  Leu  Asn  Tyr  Thr  Arg
                           35                      40                      45

Phe  Ser  Ser  Lys  Ser
                           50
```

( 2 ) INFORMATION FOR SEQ ID NO:41:

( i ) SEQUENCE CHARACTERISTICS:
        ( A ) LENGTH: 54 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:41:

```
            Asn  Ile  Leu  Val  Asn  Gln  Asn  Leu  Cys  Cys  Lys  Val  Ser  Asp  Phe  Gly
            1                  5                      10                      15

Leu  Thr  Arg  Leu  Leu  Asp  Asp  Phe  Asp  Gly  Thr  Tyr  Glu  Thr  Gln  Gly
                           20                      25                      30

Gly  Lys  Ile  Pro  Ile  Arg  Trp  Thr  Ala  Pro  Glu  Ala  Leu  Ala  His  Arg
                           35                      40                      45

Ile  Phe  Thr  Thr  Ala  Ser
                           50
```

( 2 ) INFORMATION FOR SEQ ID NO:42:

( i ) SEQUENCE CHARACTERISTICS:
        ( A ) LENGTH: 55 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:42:

```
            Asn  Ile  Leu  Val  Asn  Ser  Asn  Leu  Val  Cys  Lys  Val  Ser  Asp  Phe  Gly
            1                  5                      10                      15

Leu  Ser  Arg  Val  Leu  Glu  Asp  Asp  Pro  Glu  Ala  Thr  Tyr  Thr  Thr  Ser
                           20                      25                      30

Gly  Gly  Lys  Ile  Pro  Ile  Arg  Trp  Thr  Ala  Pro  Glu  Ala  Ile  Ser  Tyr
                           35                      40                      45

Arg  Lys  Phe  Thr  Ser  Ala  Ser
                      50                   55
```

( 2 ) INFORMATION FOR SEQ ID NO:43:

( i ) SEQUENCE CHARACTERISTICS:
        ( A ) LENGTH: 57 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:43:

```
Asn Ile Leu Val Asn Ser Asn Leu Val Cys Lys Val Ser Asp Phe Gly
 1               5                  10                  15
Leu Ser Arg Tyr Leu Gln Asp Asp Thr Ser Asp Pro Thr Tyr Thr Ser
            20                  25                  30
Ser Leu Gly Gly Lys Ile Pro Val Arg Trp Thr Ala Pro Glu Ala Ile
        35                  40                  45
Ala Tyr Arg Lys Phe Thr Ser Ala Ser
    50                  55
```

( 2 ) INFORMATION FOR SEQ ID NO:44:

( i ) SEQUENCE CHARACTERISTICS:
        ( A ) LENGTH: 54 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:44:

```
Asn Val Leu Val Lys Thr Pro Gln His Val Lys Ile Thr Asp Phe Gly
 1               5                  10                  15
Leu Ala Lys Leu Leu Gly Ala Glu Glu Lys Glu Tyr His Ala Glu Gly
            20                  25                  30
Gly Lys Val Pro Ile Lys Trp Met Ala Leu Glu Ser Ile Leu His Arg
        35                  40                  45
Ile Tyr Thr His Gln Ser
    50
```

( 2 ) INFORMATION FOR SEQ ID NO:45:

( i ) SEQUENCE CHARACTERISTICS:
        ( A ) LENGTH: 54 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:45:

```
Asn Val Leu Val Lys Ser Pro Asn His Val Lys Ile Thr Asp Phe Gly
 1               5                  10                  15
Leu Ala Arg Leu Leu Asp Ile Asp Glu Thr Glu Tyr His Ala Asp Gly
            20                  25                  30
Gly Lys Val Pro Ile Lys Trp Met Ala Leu Glu Ser Ile Leu Arg Arg
        35                  40                  45
Arg Phe Thr His Gln Ser
    50
```

( 2 ) INFORMATION FOR SEQ ID NO:46:

( i ) SEQUENCE CHARACTERISTICS:

(A) LENGTH: 54 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:46:

| Asn | Val | Leu | Val | Thr | Glu | Asp | Asn | Val | Met | Lys | Ile | Ala | Asp | Phe | Gly |
|---|---|---|---|---|---|---|---|---|---|---|---|---|---|---|---|
| 1 | | | | 5 | | | | | 10 | | | | | 15 | |

| Leu | Ala | Arg | Asp | Ile | His | His | Ile | Asp | Tyr | Tyr | Lys | Lys | Thr | Thr | Asn |
|---|---|---|---|---|---|---|---|---|---|---|---|---|---|---|---|
| | | | 20 | | | | | 25 | | | | | 30 | | |

| Gly | Arg | Leu | Pro | Val | Lys | Trp | Met | Ala | Pro | Glu | Ala | Leu | Phe | Asp | Arg |
|---|---|---|---|---|---|---|---|---|---|---|---|---|---|---|---|
| | | 35 | | | | | 40 | | | | | 45 | | | |

| Ile | Tyr | Thr | His | Gln | Ser |
|---|---|---|---|---|---|
| | | 50 | | | |

(2) INFORMATION FOR SEQ ID NO:47:

(i) SEQUENCE CHARACTERISTICS:
(A) LENGTH: 54 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:47:

| Asn | Val | Leu | Val | Thr | Glu | Asn | Asn | Val | Met | Lys | Ile | Ala | Asp | Phe | Gly |
|---|---|---|---|---|---|---|---|---|---|---|---|---|---|---|---|
| 1 | | | | 5 | | | | | 10 | | | | | 15 | |

| Leu | Ala | Arg | Asp | Ile | Asn | Asn | Ile | Asp | Tyr | Tyr | Lys | Lys | Thr | Thr | Asn |
|---|---|---|---|---|---|---|---|---|---|---|---|---|---|---|---|
| | | | 20 | | | | | 25 | | | | | 30 | | |

| Gly | Arg | Leu | Pro | Val | Lys | Trp | Met | Ala | Pro | Glu | Ala | Leu | Phe | Asp | Arg |
|---|---|---|---|---|---|---|---|---|---|---|---|---|---|---|---|
| | | 35 | | | | | 40 | | | | | 45 | | | |

| Val | Tyr | Thr | His | Gln | Ser |
|---|---|---|---|---|---|
| | | 50 | | | |

(2) INFORMATION FOR SEQ ID NO:48:

(i) SEQUENCE CHARACTERISTICS:
(A) LENGTH: 54 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:48:

| Asn | Val | Leu | Leu | Ala | Gln | Gly | Lys | Ile | Val | Lys | Ile | Cys | Asp | Phe | Gly |
|---|---|---|---|---|---|---|---|---|---|---|---|---|---|---|---|
| 1 | | | | 5 | | | | | 10 | | | | | 15 | |

| Leu | Ala | Arg | Asp | Ile | Met | His | Asp | Ser | Asn | Thr | Val | Ser | Lys | Gly | Ser |
|---|---|---|---|---|---|---|---|---|---|---|---|---|---|---|---|
| | | | 20 | | | | | 25 | | | | | 30 | | |

| Thr | Phe | Leu | Pro | Val | Lys | Trp | Met | Ala | Pro | Glu | Ser | Ile | Phe | Asp | Asn |
|---|---|---|---|---|---|---|---|---|---|---|---|---|---|---|---|
| | | 35 | | | | | 40 | | | | | 45 | | | |

| Leu | Thr | Tyr | Tyr | Leu | Ser |
|---|---|---|---|---|---|
| | | 50 | | | |

(2) INFORMATION FOR SEQ ID NO:49:

(i) SEQUENCE CHARACTERISTICS:
(A) LENGTH: 54 amino acids
(B) TYPE: amino acid
(C) STRANDEDNESS: Not Relevant
(D) TOPOLOGY: linear (  i  i  ) MOLECULE TYPE: protein ( x i ) SEQUENCE DESCRIPTION: SEQ ID NO:49:

Asn Met Leu Ile Cys Glu Gly Lys Leu Val Lys Ile Cys Asp Phe Gly
1               5                   10                  15

Leu Ala Arg Asp Ile Met Arg Asp Ser Asn Tyr Ile Ser Lys Gly Ser
            20                  25                  30

Thr Phe Leu Pro Leu Lys Trp Met Ala Pro Glu Ser Ile Phe Asn Ser
        35                  40                  45

Leu Tyr Thr Thr Leu Ser
    50

( 2 ) INFORMATION FOR SEQ ID NO:50:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear (  i  i  ) MOLECULE TYPE: protein ( x i ) SEQUENCE DESCRIPTION: SEQ ID NO:50:

Asn Val Leu Leu Thr Ser Gly His Val Ala Lys Ile Gly Asp Phe Gly
1               5                   10                  15

Leu Ala Arg Asp Ile Met Asn Asp Ser Asn Tyr Val Val Lys Gly Asn
            20                  25                  30

Ala Arg Leu Pro Val Lys Trp Met Ala Pro Glu Ser Ile Phe Asp Cys
        35                  40                  45

Val Tyr Thr Tyr Gln Ser
    50

( 2 ) INFORMATION FOR SEQ ID NO:51:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear (  i  i  ) MOLECULE TYPE: protein ( x i ) SEQUENCE DESCRIPTION: SEQ ID NO:51:

Asn Ile Leu Leu Ser Glu Asn Asn Val Val Lys Ile Cys Asp Phe Gly
1               5                   10                  15

Leu Ala Arg Asp Ile Tyr Lys Asn Pro Asp Tyr Val Arg Arg Gly Asp
            20                  25                  30

Thr Arg Leu Pro Leu Lys Trp Met Ala Pro Glu Ser Ile Phe Asp Lys
        35                  40                  45

Val Tyr Ser Thr Lys Ser
    50

( 2 ) INFORMATION FOR SEQ ID NO:52:

( i ) SEQUENCE CHARACTERISTICS:
    ( A ) LENGTH: 54 amino acids
    ( B ) TYPE: amino acid
    ( C ) STRANDEDNESS: Not Relevant
    ( D ) TOPOLOGY: linear (  i  i  ) MOLECULE TYPE: protein ( x i ) SEQUENCE DESCRIPTION: SEQ ID NO:52:

Asn Cys Leu Val Gly Gln Gly Leu Val Val Lys Ile Gly Asp Phe Gly

-continued

```
        1               5                       10                      15
    Met Ser Arg Asp Ile Tyr Ser Thr Asp Tyr Tyr Arg Val Gly Gly Arg
                20                  25                      30
    Thr Met Leu Pro Ile Arg Trp Met Pro Pro Glu Ser Ile Leu Tyr Arg
                35              40                  45
    Lys Phe Thr Thr Glu Ser
        50
```

(2) INFORMATION FOR SEQ ID NO:53:

(i) SEQUENCE CHARACTERISTICS:
        (A) LENGTH: 54 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:53:

```
    Asn Cys Leu Val Gly Glu Asn Leu Leu Val Lys Ile Gly Asp Phe Gly
    1               5                       10                      15
    Met Ser Arg Asp Val Tyr Ser Thr Asp Tyr Tyr Arg Val Gly Gly Arg
                20                  25                      30
    Thr Met Leu Pro Ile Arg Trp Met Pro Pro Glu Ser Ile Met Tyr Arg
                35              40                  45
    Lys Phe Thr Thr Glu Ser
        50
```

(2) INFORMATION FOR SEQ ID NO:54:

(i) SEQUENCE CHARACTERISTICS:
        (A) LENGTH: 54 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:54:

```
    Asn Cys Met Val Ala Glu Asp Phe Thr Val Lys Ile Gly Asp Phe Gly
    1               5                       10                      15
    Met Thr Arg Asp Ile Tyr Glu Thr Asp Tyr Tyr Arg Lys Gly Gly Lys
                20                  25                      30
    Gly Leu Leu Pro Val Arg Trp Met Ser Pro Glu Ser Leu Lys Asp Gly
                35              40                  45
    Val Phe Thr Thr His Ser
        50
```

PROTEIN-TYROSINE KINASE GENES

This is a continuation of application Ser. No. 07/884,486 failed on May 15, 1992, now abandoned.

This work was supported by Grant Number NS-23896 from the National Institutes of Health. The United States Government may retain certain rights of this invention.

BACKGROUND OF THE INVENTION

1. Field of the Invention

This invention relates generally to the molecular cloning of genes which encode unique protein-tyrosine kinase receptor subtypes which can be used in an assay to screen various compositions which modulate these receptors.

2. Related Art

Among the signal transduction molecules implicated in neural development, the receptor protein-tyrosine kinases (PTKs) are of particular interest: These proteins function as transmembrane receptors for polypeptide growth factors, and contain a tyrosine kinase as an integral part of their cytoplasmic domains (Yarden and Ullrich, *Annu. Rev. Biochem.*, 57:443–478, 1988; Ullrich and Schlessinger, *Cell*, 61:203–212, 1990). Binding of a polypeptide ligand to its corresponding cell surface receptor results in rapid activation of that receptor's intracellular tyrosine kinase, which in turn results in the tyrosine phosphorylation of the receptor itself and of multiple downstream target proteins (Hunter and Cooper, *Annu. Rev. Biochem.*, 54:897–930, 1985; Hunter, et al, eds. J. B. Hook and G. Poste, Plenum Press, New York and London, pp. 119–139, 1990). For many receptor PTKs, growth factor binding ultimately triggers multiple rounds of cell division.

Molecular studies of mutations that affect cell differentiation have demonstrated that several of these receptor PTKs act as early determinants of cell fate. Loss-of-function mutations in the sevenless gene of Drosophila (Harris, et al., *J. Physiol.*, 256:415–439, 1976), for example, abolish the tyrosine kinase activity of a transmembrane receptor expressed in the developing ommatidia of the eye and result in the aberrant differentiation of the precursors to the number 7 photoreceptors (Basler and Haten, *Cell*, 54:299–311, 1988; Rubin, *Cell*, 57:519–520, 1989). Rather than becoming number 7 photoreceptor cells, these precursors instead differentiate into non-neuronal cone cells, which form the lens. In marked contrast, the remaining complement of photoreceptors (numbers 1–6 and 8) differentiate normally.

Mutations in genes encoding other receptor PTKs have also been shown to affect cell differentiation. For example, mutations in the torso gene of Drosophila specifically disrupt the terminal differentiation of extreme anterior and posterior structures in the embryo (Sprenger, et al., *Nature* 338:478–483, 1989), and mutations in the Drosophila Ellipse gene, which encodes a homolog of the mammalian epidermal growth factor (EGF) receptor, result in the developmental failure of multiple cell types in the eye (Baker and Rubin, *Nature*, 340:150–153, 1989). In vertebrates, mutations in the mouse dominant white spotting locus (W), which encodes the c-kit receptor PTK, produce pleiotropic developmental effects that include disruption of the normal proliferation and differentiation of neural crest-derived melanocytes (Chabot, et al., *Nature*, 335:88–89, 1988; Geissler, et al., *Cell*, 55:185–192, 1988).

Parallel to these studies of the developmental role of receptor PTKs has been the demonstration that many of the ligands for these receptors influence the differentiation of neural cells in culture. Platelet-derived growth factor (PDGF), for example, has been shown to stimulate the proliferation and prevent the premature differentiation of oligodendrocyte/type-2 astrocyte glial progenitor cells in rat optic nerve cultures (Noble, et al., *Nature*, 333:560–562, 1988; Raff, et al., *Nature*, 333:562–565, 1988).

Similarly, both acidic and basic fibroblast growth factor (bFGF) have been shown to stimulate the neuronal differentiation of cultured rat pheochromocytoma (PC-12) cells (Togari, et al., *J. Neurosci.*, 5:307–316, 1985; Wagner and D'Amore, *J. Cell Biol.*, 103:1363–1367, 1986). bFGF has also been reported to prolong survival and stimulate neurite outgrowth in cultures of primary cortical and hippocampal neurons (Morrison, et al., *Proc. Natl. Acad. Sci. USA*, 83:7537–7541, 1986; Walicke, et al., *Proc. Natl. Acad. Sci. USA*, 83:3012–3016, 1986), to induce cell division, neuronal differentiation, and nerve growth factor (NGF) dependence in adrenal chromatifin cells (Stemple, et al., *Neuron*, 1:517–525, 1988), and to function as a survival factor, both in vivo and in vitro, for neural crest-derived non-neuronal cells during the early development of sensory ganglia (Kalcheim, *Dev. Biol.*, 134:1–10, 1989). Recently, the product of the mouse mutant steel gene (Sl), which interacts genetically with W, has been identified as a growth factor ligand for the c-kit receptor (Witte, *Cell*, 63:5–6, 1990). Genetic and biochemical studies of the expression patterns of the sevenless, torso and c-kit receptors suggest that specification of cell fates can be achieved through the spatially and temporally restricted expression of either the receptors or their ligands (Rubin, *Cell*, 57:519–520, 1989; Tomlinson and Ready, *Biol.*, 120:366–376, 1987; Reinke and Zipursky, *Cell*, 55:321–330, 1988; Banerjee and Zipursky, *Neuron*, 4:177–187, 1990; Stevens, et al., *Nature*, 346:660–663, 1990; Matsui, et al., *Nature*, 347:667–669, 1990).

SUMMARY OF THE INVENTION

In accordance with the present invention, novel receptor protein tyrosine kinase (PTK) subtype polypeptides have been isolated. These PTKs possess a tyrosine kinase domain and a unique tissue expression pattern different from all previously known receptor PTKs. These novel receptor PTK subtypes have been designated tyro-1 through tyro-8 and tyro-10 through tyro-12. Of particular interest among the new PTK subtypes are tyro-1 through tyro-6 which are found predominantly or exclusively in neural tissue.

By providing the polynucleotide sequences and corresponding polypeptide sequences for the new PTK subtypes, it is now possible to obtain polynucleotide sequences encoding the entire receptor PTK for each of the subtypes.

Further, the invention provides a method for identifying compositions which potentially affect the activity of the receptor. PTK subtype. This method comprises (a) contacting cells containing DNA which expresses the PTK polypeptide with the composition under conditions suitable for cell culture; and (b) monitoring the cells for a physiological change resulting from this interaction.

In addition, the present invention provides unique oligonucleotide which align with the unique flanking regions of the receptor PTK subtypes, thereby allowing amplification of the polynucleotides encoding the receptor PTK subtype by such techniques as polymerase chain reaction (PCR).

The present invention also provides a method of gene therapy comprising introducing into a host subject an expression vector comprising a nucleotide sequence encoding a receptor PTK subtype capable of affecting a biological activity of the host subject cell.

DETAILED DESCRIPTION OF THE PREFERRED EMBODIMENT

Figure 1A:
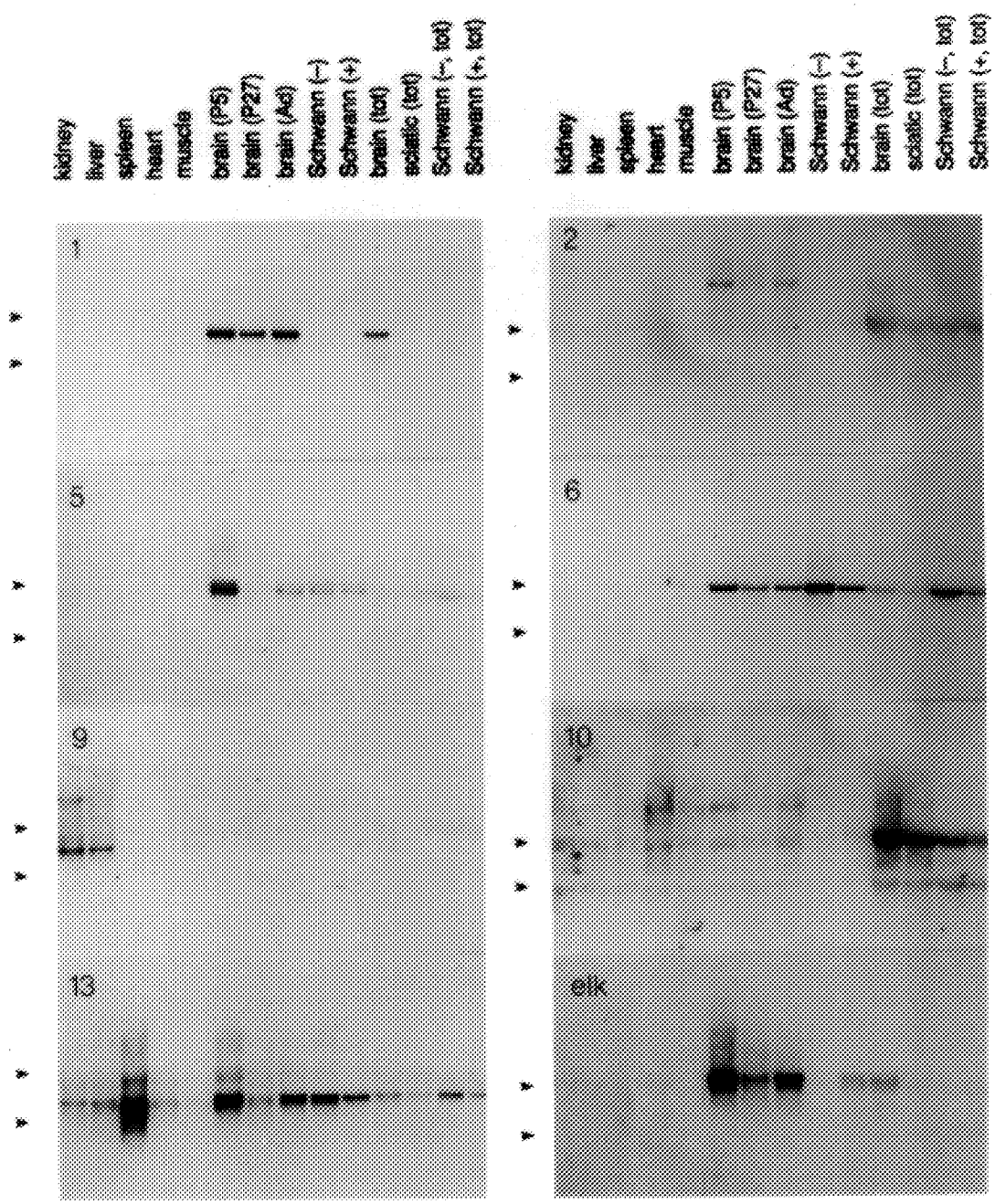
FIG. 1 shows the tissue expression profiles of the novel PTK mRNAs.

The present invention relates to novel protein tyrosine kinase (PTK) gene and Polypeptides encoded by these genes. Various of these PTK subtypes are implicated in neural development where they function primarily as signal transduction molecules. The receptor PTKs of the invention are characterized as having a tyrosine kinase domain and a unique tissue expression pattern which differs from that of all known receptor PTKs.

The invention provides polynucleotides, such as DNA, cDNA, and RNA, encoding novel receptor PTK polypeptides. It is understood that all polynucleotides encoding all or a portion of the receptor PTKs of the invention are also included herein, so long as they exhibit at least one protein tyrosine kinase domain and the tissue expression pattern characteristic of a given subtype. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

A receptor PTK cDNA library can be screened by injecting the various cDNAs into oocytes, allowing sufficient time for expression of the cDNA gene products to occur, and testing for the presence of the desired cDNA expression product, for example, by using antibody specific for the receptor PTK subtype polypeptide or by using functional assays for receptor PTK subtype activity and a tissue expression pattern characteristic of the desired subtype.

Alternatively, a cDNA library can be screened indirectly for receptor PTK polypeptides having at least one epitope using antibodies specific for receptor PTK subtypes of the invention. Such antibodies can be either polyclonally or monoclonally derived and used to detect expression product indicative of the presence of protein tyrosine kinase receptor PTK subtype cDNA.

The development of specific DNA sequences encoding receptor PTK subtypes of the invention can also be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Specifically embraced in (1) are genomic DNA sequences which encode allelic variant forms. Also included are DNA sequences which are degenerate as a result of the genetic code.

Of the three above-noted methods for developing specific DNA sequences for use in recombinant procedures, the use of genomic DNA isolates (1), is the least common. This is especially true when it is desirable to obtain the microbial expression of mammalian polypeptides because of the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucleic Acid Research*, 11:2325, 1983).

Since the novel DNA sequences of the invention encode essentially all or part of a receptor PTK, it is now a routine matter to prepare, subclone, and express smaller polypeptide fragments of DNA from this or corresponding DNA sequences. Alternatively, by utilizing the DNA fragments disclosed herein which define the unique tyrosine kinase receptor subtype of the invention it is possible, in conjunction with known techniques, to determine the DNA sequences encoding the entire receptor subtypes. Such techniques are described in U.S. Pat. No. 4,394,443 and U.S. Pat. No. 4,446,235 which are incorporated herein by reference.

The polypeptide resulting from expression of a DNA sequence of the invention can be further characterized as being free from association with other eukaryotic polypeptides or other contaminants which might otherwise be associated with the protein kinase in its natural cellular environment.

For purposes of the present invention, receptor PTK subtypes which are homologous to those of the invention can be identified by structural as well as functional similarity. Structural similarity can be determined, for example, by assessing polynucleotide strand hybridization or by screening with antibody, especially a monoclonal antibody, which recognizes a unique epitope present on the subtypes of the invention. When hybridization is used as criteria to establish structural similarity, those polynucleotide sequences which hybridize under stringent conditions to the polynucleotides of the invention are considered to be essentially the same as the polynucleotide sequences of the invention.

In the present invention, polynucleotide sequences encoding receptor PTK subtype may be introduced into a host cell by means of a recombinant expression vector. The term "recombinant expression vector" refers to a plasmid, virus or other vehicle known in the art that has been manipulated by insertion or incorporation of the polynucleotide sequences of the invention. Such expression vectors typically contain a promotor sequence which facilitates efficient transcription of the inserted sequence in the host. The expression vector also typically contains specific genes which allow phenotypic selection of the transformed cells. Alternatively, nucleotide sequences encoding a receptor PTK subtype can be introduced directly in the form of free nucleotide, for example, by microinjection, or transfection.

DNA sequences encoding receptor PTK subtypes of the invention can be expressed in vivo by DNA transfer into a suitable host cell. "Recombinant host cells" or "host cells" are cells in which a vector can be propagated and its DNA expressed. The term includes not only prokaryotes, but also such eukaryotes as yeast, filamentous fungi, as well as animal cells which can replicate and express an intron-free DNA sequence of the invention and any progeny of the subject host cell. It is understood that not all progeny are identical to the parental cell since there may be mutations that occur at replication. However, such progeny are included when the terms above are used.

Methods of expressing DNA sequences having eukaryotic coding sequences in prokaryotes are well known in the art. Biologically functional viral and plasmid DNA vectors capable of expression and replication in a host are known in the art. Such vectors are used to incorporate DNA sequences of the invention. Hosts include microbial, yeast and mammalian organisms. Transformation of a host cell with recombinant DNA may be carried out by conventional techniques which are well known to those skilled in the art. Where the host is prokaryotic, such as $E.$ $coli$, competent cells which are capable of DNA uptake can be prepared from cells harvested after exponential growth phase and subsequently treated by the $CaCl_2$ method well known in the art. Alternatively, $MgCl_2$ or RbCl can be used. Transformation can also be performed after forming a protoplast of the host cell.

When the host is a eukaryote, such methods of transfection of DNA as calcium phosphate co-precipitates, conventional mechanical procedures such as microinjection, insertion of a plasmid encased in liposomes, or virus vectors may be used. Eukaryotic cells can also be cotransformed with foreign cDNA encoding the desired receptor PTK subtype protein, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982).

Where the eukaryotic host cells are yeast, the cDNA can be expressed by inserting the cDNA into appropriate expression vectors and introducing the product into the host cells. Various shuttle vectors for the expression of foreign genes in yeast have been reported (Heinemann, et al, *Nature*, 340:205, 1989; Rose, et al., *Gene*, 60:237, 1987).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with the receptor PTK subtypes of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

Minor modifications of the receptor PTK primary amino acid sequence may result in proteins which have substantially equivalent activity compared to the receptor PTKs described herein. Such modifications may be deliberate, as by site-directed mutagenesis, or may be spontaneous. All proteins produced by these modifications are included herein as long as tyrosine kinase activity and the characteristic tissue expression pattern for the subtype is present.

The invention also discloses a method for identifying a composition which affects the activity of a receptor PTK subtype of the invention. The receptor is, for example, capable of affecting cell division and/or differentiation. The composition is incubated in combination with cells under conditions suitable for cell culture, then subsequently monitoring the cells for a physiologic change.

The production of a receptor PTK can be accomplished by oligonucleotide(s) which are primers for amplification of the genomic polynucleotide encoding PTK receptor. These unique oligonucleotide primers were produced based upon identification of the flanking regions contiguous with the polynucleotide encoding the receptor PTK. These oligonucleotide primers comprise sequences which are capable of hybridizing with the flanking nucleotide sequence encoding a polypeptide having amino acid residues HRDLAAR and/or DVWS(F/Y)G(V/I) and sequences complementary thereto.

The primers of the invention embrace oligonucleotides of sufficient length and appropriate sequence so as to provide specific initiation of polymerization on a significant number of nucleic acids in the polynucleotide encoding the receptor PTK subtype. Specifically, the term "primer" as used herein refers to a sequence comprising two or more deoxyribonucleotides or ribonucleotides, preferably more than three, which sequence is capable of initiating synthesis of a primer extension product, which is substantially complementary to a receptor PTK strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 15–22 or more nucleotides, although it may contain fewer nucleotides.

Primers of the invention are designed to be "substantially" complementary to each strand of polynucleotide encoding the receptor PTK to be amplified. This means that the primers must be sufficiently complementary to hybridize with their respective strands under conditions which allow the agent for polymerization to perform. In other words, the primers should have sufficient complementarity with the flanking sequences to hybridize therewith and permit amplification of the polynucleotide encoding the receptor PTK. Preferably, the primers have exact complementarity with the flanking sequence strand.

Oligonucleotide primers of the invention are employed in the amplification process which is an enzymatic chain reaction that produces exponential quantities of polynucleotide encoding the receptor PTK relative to the number of reaction steps involved. Typically, one primer is complementary to the negative (−) strand of the polynucleotide encoding the receptor PTK and the other is complementary to the positive (+) strand. Annealing the primers to denatured nucleic acid followed by extension with an enzyme, such as the large fragment of DNA Polymerase I (Klenow) and nucleotides, results in newly synthesized + and −strands containing the receptor PTK sequence. Because these newly synthesized sequences are also templates, repeated cycles of denaturing, primer annealing, and extension results in exponential production of the region (i.e., the tyrosine kinase receptor polynucleotide sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing a protein receptor PTK of the invention. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the receptor PTK, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA or RNA utilized herein may be extracted from a body sample, such as brain, or various other tissue, by a variety of techniques such as that described by Maniatis, et al. (*Molecular Cloning*, 280:281, 1982). If the extracted sample is impure (such as plasma, serum, or blood), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative *Biology*, 43:63, 1978) and techniques for using RecA are reviewed in C. Radding (*Ann. Rev. Genetics*, 16:405–437, 1982).

If the nucleic acid containing the sequence to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be partially complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each receptor PTK nucleic acid strand. Generally, the synthesis will be initiated at the 3' end of each primer and proceed in the 5' direction along until synthesis terminates, producing molecules of different lengths. There may be agents for polymerization, however, which initiate synthesis at the 5' end and proceed in the other direction, using the same process as described above.

The newly synthesized receptor PTK strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the receptor PTK nucleic acid sequence to the extent necessary for detection. The amount of the specific nucleic acid sequence produced will accumulate in an exponential fashion.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229–237, 1988).

The present invention also provides methods for the treatment of disease employing gene therapy that modulates cellular differentiation or maturation. Such therapy can be affected by introduction of polynucleotide sequences of the invention into cells of a subject having a disease. Delivery of polynucleotide can be achieved using techniques well known in the art. For example, a recombinant expression vector, such as a chimeric virus, or a colloidal dispersion system can be employed.

Various viral vectors which can be utilized for introduction of polynucleotide according to the present invention, include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can incorporate a gene for a selectable marker so that transduced cells can be identified and generated.

By inserting a polynucleotide encoding the receptor PTK of interest into a viral vector, along with another gene which encodes ligand for a receptor on a specific target cell, the vector now becomes target specific. Retroviral vectors can be made target specific by including in the retroviral vector a polynucleotide encoding a target related binding substance. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the receptor PTK polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to, ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for introduction of polynucleotides encoding the receptor PTKs of the invention is a colloidal dispersion system. Colloidal dispersion systems include macromolecular complexes, nanocapsules, microspheres, beads, and lipid-based systems including oil-in-water emulsions, micelles, mixed micelles, and liposomes. The preferred colloidal system of this invention is a liposome.

Since the receptor PTK polypeptide may be indiscriminate in its action with respect to cell type, a targeted delivery system offers a significant improvement over randomly injected non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an epitope on the target cells. Liposomes may also be targeted to cells expressing receptors for hormones or other serum factors.

Liposomes are artificial membrane vesicles which are useful as in vitro and in vivo delivery vehicles. It has been shown that large unilamellar vesicles (LUV), which range in size from 0.2–4.0 μm can encapsulate a substantial percentage of an aqueous buffer containing large macromolecules. RNA, DNA, intact virions and peptides can be encapsulated within the aqueous interior and be delivered to cells in a biologically active form (Fraley, et al., *Trends Biochem. Sci.*, 6:77, 1981). In order for a liposome to be an efficient transfer vehicle, the following characteristics should be present: (1) encapsulation of polynucleotides of interest at high efficiency without compromising biological activity; (2) preferential and substantial binding to target cells relative to non-target cells; (3) delivery of aqueous contents of vesicle to the target cell cytoplasm at high efficiency; and (4) accurate and effective expression of genetic information (Mannino, et al., *Biotechniques*, 6:682, 1988).

The surface of the targeted delivery system may be modified in a variety of ways. In the case of a liposomal targeted delivery system, lipid groups can be incorporated into the lipid bilayer of the liposome in order to maintain the targeting receptor in stable association with the liposomal bilayer. Various linking groups can be used for joining the lipid chains to the targeting receptor.

In general, the targeted delivery system will be directed to cell surface receptors thereby allowing the delivery system to find and "home in" on the desired cells. Alternatively, the delivery system can be directed to any cell surface molecule preferentially found in the cell population for which treatment is desired and capable of association with the delivery system. Antibodies can be used to target liposomes to specific cell-surface molecules. For example, where a tumor is associated with a receptor PTK of the invention, certain antigens expressed specifically or predominantly on the cells of the tumor may be exploited for the purpose of targeting antibody tyrosine kinase receptor DNA-containing liposomes directly to a malignant tumor, if desired.

An alternative use for recombinant retroviral vectors comprises the introduction of polynucleotide sequences into the host by means of skin transplants of cells containing the virus. Long term expression of foreign genes in implants, using cells of fibroblast origin, may be achieved if a strong housekeeping gene promoter is used to drive transcription. For example, the dihydrofolate reductase (DHFR) gene promoter may be used. Cells such as fibroblasts, can be infected with virions containing a retroviral construct containing the receptor PTK gene of interest together with a gene which allows for specific targeting, such as a tumor-associated antigen and a strong promoter. The infected cells can be embedded in a collagen matrix which can be grafted into the connective tissue of the dermis in the recipient subject. As the retrovirus proliferates and escapes the matrix it will specifically infect the target cell population. In this way the transplantation results in increased amounts of receptor PTK being produced in cells manifesting the disease.

Because the present invention identifies nucleotide sequences encoding novel receptor PTKs, it is possible to design therapeutic or diagnostic protocols utilizing these sequences. Thus, where a disease is associated with a receptor PTK of the invention, the polynucleotide sequence encoding the PTK can be utilized to design sequences which interfere with the function of the receptor. This approach utilizes, for example, antisense nucleic acid and ribozymes to block translation of specific receptor mRNA, either by masking the mRNA with antisense nucleic acid or by cleaving it with ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a doublestranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target receptor-producing cell. The use of antisense methods to inhibit the in vitro translation of genes is well known in the art (Marcus-Sakura, *Anal.Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Antisense sequences can be therapeutically administered by techniques as described above for the administration of receptor PTK polynucleotides. Targeted liposomes are especially preferred for therapeutic delivery of antisense sequences.

The following Examples are intended to illustrate, but not to limit the invention. While such Examples are typical of those that might be used, other procedures known to those skilled in the art may alternatively be utilized.

EXAMPLE 1

ISOLATION OF NOVEL PTK CLONES

PCR was used to amplify PTK-related sequences located between the degenerate oligonucleotide primer sequences shown in TABLE 1. These primers correspond to the amino acid sequences HRDLAAR (SEQ ID NO:27) (upstream) and DVWS(F/Y)G(I/V)(SEQ ID NO:28) (downstream), which flank a highly conserved region of the kinase domain shared by receptor PTKs (Hanks, et al., *Science*, 241:42–52, 1988). The upstream primer was chosen to exclude members of the src family of cytoplasmic tyrosine kinases. The downstream primer was chosen such that a second highly conserved amino acid sequence diagnostic or PTKs—P(I/V)(K/R)W(T/M)APE(SEQ ID NO:29)—would be contained within amplified PCR products.

The DNA substrates used for amplification were sciatic nerve cDNA populations prepared for use in the construction of subtracted cDNA libraries. Three different subtracted cDNAs were produced. The first two, UN and TWI, were enriched for transcripts expressed predominantly in Schwann cells. The third, BD, was enriched for transcripts shared between Schwann cells and myelinating stage (P17–23) brain. Two initial hybridizations were performed. Both samples contained 500 ng of single-stranded sciatic nerve cDNA mixed with the following poly(A)-selected RNAs: 10 μg of muscle, 7.5 μg of liver, and 5 μg of kidney. Both samples also contained a series of RNAs synthesized in vitro; these encoded portions of the sense strand of the following Schwann cell transcripts: NGF receptor, glial fibrillary acidic protein, proteolipid protein, protein zero, myelin basic protein, and CNPase. The first sample contained, in addition, 10 μg of poly(A)-selected RNA from rat brain cerebellum (P19) and cortex (P3). Each hybridization was allowed to proceed to approximately $R_0t$ 2000. Following hybridization, these samples were bound to hydroxylapatite (0.12M phosphate buffer, 65° C.). For the first sample, material not binding to hydroxylapatite (HAP) was collected and converted to a double-stranded form. This material was designated UN (unbound). For the second sample, cDNA not binding to the column was further hybridized with 40 μg of poly(A)-selected RNA from rat cerebellum (equal mix of P17 and P23) until $R_0t$ 800. This mixture was re-applied to hydroxylapatite. The unbound material was collected and converted to a double-stranded form and designated TWI (twice unbound). The material that bound to the HAP column was then eluted and also converted to a double-stranded DNA form. This fraction was called BD (bound).

Approximately 2–4 ng of the UN and TWI subtracted cDNAs and 1 ng of the BD cDNA were used in each of the amplifications, which were conducted using reagents and instructions provided by U.S. Biochemicals. The final concentration of magnesium ion was increased to 2.1 mM. Thirty-nine cycles of amplification were performed on a water-cooled vtwb Model 1 cycler (San Diego, Calif.). Amplification parameters included an initial 1 minute denaturation step at 94° C., a 5 minute annealing at 37° C., a 5 minute extension at 65° C., and a 0.3 minute denaturation at 94° C. Approximately 4 μg of each of the degenerate primers (TABLE 1) was included in each amplification. The unusually low annealing temperatures employed in these amplifications may favor polymerase extension from stably-hybridized oligonucleotide primers, resulting in a broader and less-biased amplified population than those obtained with previous protocols (Wilks, *Proc. Natl. Acad. Sci. USA,* 86:1603–1607, 1989).

TABLE 1

(SEQ ID NOS: 30–35)

| EXTRACELLULAR | TM | KINASE:DOMAIN |
|---|---|---|
| HRDLAAR | | DV WSFGV |

| | | | | | |
|---|---|---|---|---|---|
| EFG-R | HRDLAARNVL VKTPQ | EV KITDFGL AKLLG AEEKEYHA | EGGKVPI KWMALES I | LHRI YTHQSDV WSYGV |
| INS-R | HRDLAARNCMVAHDF | TV KIGDFGMTRDI YETDYYRKG | GKGLLPVRWMAPES L | KDGVETTS SDMWSFGV |
| PDGF-R | HRDLAARNVL I CEGK | LV KICDFGL ARDI MRDS NYI S K | GS TYLPLKWMAPES I | FNS LYTTLSDV WSFGI |
| FGF-R | HRDLAARNVL VTEDN | VMKIADFGL ARDI HHI DYYKKT | TNGRLPVKWMAPEAL | FDRI YTHQSDV WSFGV |
| CONSENSUS | HRDLAARNVL V | VKI DFGL ARDI  Y | G LP KWMAPES | YT SDV WSFGV |

```
                                                              Y        I
                H  R  D  L  A  A  R                   D  V  W  S  F  G  V

OLIGONUCLEOTIDE             C    CC    A                   A      ACA AA    C
PRIMERS         5' GGAATTCCATCGNGATTTNGATTTNGCNGCNCG 3'   3' CTGCANACCTGGATGCCNTAGAGCTCC 5'
```

Amplified DNAs were size fractionated on 5% non-denaturing acrylamide gels. The gels were stained with ethidium bromide (1 μg/ml) and amplified bands of ~220 bp were excised. These bands were eluted overnight into 0.5M ammonium acetate. 1 mM EDTA, 0.2% SDS, and eluted DNA was then precipitated with 10 μg of tRNA carrier. Recovered PCR products were blunt-ended using T4 DNA polymerase, and phosphorylated using T4 polynucleotide kinase. Approximately 40 ng of insert was then ligated with 200 ng of dephosphorylated SmaI/EcoRV-digested pBluescript plasmid. One-tenth of each ligation was used to transform MC1061 bacteria.

The DNA sequence of both strands of each PCR product subclone was determined from alkaline lysis miniprep DNA, using the dideoxy chain termination method. In those cases in which clones having apparently identical inserts were isolated multiple times, the sequence of complementary strands was derived from independent clones.

EXAMPLE 2

SEQUENCE ANALYSIS OF PCR SUBCLONES

Sequence analysis of 168 PCR product subclones yielded 155 with significant similarity to the tyrosine kinase family. TABLE 2 lists the 27 distinct kinase domain sequences contained in this set, which includes those of the abl (human; Shtivelman, et al., *Cell,* 47:277–284, 1986) arg (human: Kruh, et al., *Science,* 234:1545–1548, 1986), and fer cytoplasmic (nonreceptor) kinases (human, Hao, et al, *Mol. Cell.*

Biol., 9:1587–1593, 1989), as well as those of the receptors for EGF-R (human; Ullrich, et al., Nature 309, 418–425, 1984), PDGF-A (human; Matsui, et al., Science, 243:800–804, 1989; rat; Lee, et al., Science, 245:57–60, 1989; Reid, et al., Proc. Natl. Acad. Sci. USA, 87:1596–1600, 1990; Safran, et al., Oncogene, 5:635–643, 1990), colony-stimulating factor 1 (CSF-1; human; Coussens, et al., Nature, 320:277–280, 1986; mouse; Rothwell and Rohrschneider, Oncogene Res., 1:311–324, 1987, and insulin-like growth factor 1 (IGF-1; human; Ullrich et al., EMBO, J., 5:2503–2512, 1986).

Other domain sequences listed include fes (human; Roebroek, et al., EMBO J., 4:2897–2903, 1985); Dsrc (Drosophila; Gregory, et al, Mol. Cell. Biol., 7:2119–2127, 1987); eph (human; Hirai, et al., Science, 238:1717–1720, 1987; eck (human; Lindberg and Hunter, Mol Cell. Biol., in press, 1990); elk (rat; Letwin, et al., Oncogene, 3:621–627, 1988); neu (Bargmann, et al., Nature, 319:226–230, 1986); bek (mouse; Kornbluth, et al., Mol. Cell. Biol., 8:5541–5544, 1988); fit (human; Shibuya, et al., Oncogene, 5:519–524, 1990); trk, (human; Martin-Zanca, et al., Nature, 319:743–748, 1986), and trk B (mouse; Klein, et al., EMBO J., 8:3701–3709, 1989).

Amino acid sequences were deduced from the nucleotide sequence of the 27 different PTK domain cDNAs. Deduced amino acid sequences corresponding to the oligonucleotide primers used for PCR amplification were not included. Kinase domain sequences are segmented according to the subdomains defined by Hanks, et al. (Science, 241:42–52, 1988). After each sequence is a number indicating the number of times it was identified. Numbers listed parenthetically correspond to clones uniquely obtained from amplification of the BD substrate. The segregation of kinase domain subfamilies is based solely on amino acid sequence conservation; sequences denoted by an asterisk were not encountered in this survey but have been included to facilitate comparisons.

The high percentage of isolates encoding tyrosine kinases (92%) and the large number of different kinase clones obtained probably reflect the highly degenerate primers and low temperature annealing and extension parameters used for PCR amplification, as well as the stringent size criteria used in the subcloning and sequencing of PCR products.

Of the 27 different kinases identified in this nervous system survey, 11 (tyro-1 through tyro-8 and tyro-10 through tyro-12) are novel. For the previously identified kinases, several rat isolates differ by 1 or 2 amino acids from the kinase domain sequences reported for other species. Nucleotide sequence comparisons suggest that these differences are accounted for by species variation and do not represent the amplification of novel kinase cDNAs. The novel isolates tyro-1 and tyro-11 were each obtained only a single time.

The kinase domain sequences of tyro-1 through tyro-13 have been grouped by similarity to the equivalent sequences of other PTKs (TABLE 2). The indicated subfamilies were defined with reference to a computer-generated phylogenetic tree, constructed from an analysis of 13 novel partial PTK sequences along with a set of 55 additional PTKs, according to the methods of Fitch and Margoliash (Science, 15:279–284, 1967) as implemented by the programs of Feng and Doolittle (J. Mol. Evol., 25:351–360, 1987). The resulting closely related sequence clusters were used to organize the kinase subfamilies presented in TABLE 2. Tyro-1 and tyro-4, for example, are related to the epithelial cell kinase (eck) (Lindberg and Hunter, Mol. Cell. Biol., in press, 1990), tyro-2 to the EGF receptor and the neu protooncogene (Bargmann, et al., Nature, 319:226–230, 1986), tyro-5, tyro-6, and tyro-11 to the elk kinase (Letwin, et al., Oncogene, 3:621–627, 1988), tyro-9 to the bFGF receptor, and tyro-10 to trk and trkB (Martin-Zanca, et al., Nature, 319:743–748, 1986; Klein, et al., EMBO J., 8:3701–3709, 1989). Although they exhibit similarity to the insulin receptor, tyro-3, tyro-7, and tyro-12 are listed as a novel subfamily since they are more closely related to each other than to any previously described kinase. The eck- and elk-related sequences are listed in separate subsets, but it is important to note the high degree of similarity between these subfamilies. The sequences of fes, trk, trkB, and Dsrc28 (each marked with an asterisk) are included in TABLE 2 only for comparison, since they were not encountered in these cloning studios.

EXAMPLE 3

TISSUE EXPRESSION PROFILE OF NOVEL PTK mRNAs

The expression pattern of the 13 novel kinase clones were characterized by first examining the relative levels of mRNA present in a variety of neonatal and adult rat tissues. Radiolabeled cDNA probes for each of these clones, as well as probes prepared from isolates of the bFGF receptor, bek, and elk kinases, were hybridized to a set of eight parallel Northern blots containing RNA isolated from kidney, liver, spleen, heart, skeletal muscle, brain, sciatic nerve, and cultured Schwann cells. RNA was isolated from Schwann cells cultured in both the presence and absence of the adenylate cyclase activator forskolin, since at least one receptor PTK gene (that encoding the PDGF-B receptor) exhibits cell-specific cAMP induction in these cells (Weinmaster and Lemke, EMBO J., 9:915–920, 1990) individual blots were in some cases reutilized for as many as four rounds of hybridization.

Total RNA from various tissues was prepared by the method of Chomczynski and Sacchi (Anal. Biochem., 162:156–159, 1987). One additional phenol-chloroform extraction was performed prior to nucleic acid precipitation. Poly(A)-selected RNA samples were purified by either column chromatography or in batch using oligo(dT)-cellulose type III (Collaborative Research). RNA samples were denatured in 50% formamide, 2.2M formaldehyde, and MOPS at 65° C. for 10 min, electrophoresed in 1.0% agarose, 2.2M formaldehyde, and MOPS, transferred to Nytran filters (Schleicher & Schuell) and baked at 80° C. for 2 hr as previously described (Monuki, et al., Neuron, 3:783–793, 1989). Probes for blot hybridizations were prepared using [$\alpha$-$^{32}$P] dCTP and a random hexamer priming kit, according to instructions provided by the manufacturer (Bethesda Research Laboratories). In all cases, final wash stringency for Northern blots was set at 0.2×SSC, 0.2% SDS, 65° C.

In situ hybridization was performed according to Simmons, et al. (J. Histotechnology, 12:169–181, 1989), with minor modifications. Paraformaldehyde-fixed brain sections (30 $\mu$m), from either adult or 33-day-old rats were used. Antisense probes from PCR product subclones were prepared using 125 $\mu$Ci or [$^{35}$S] UTP (1250 Ci/mmol: New England Nuclear) in a 10 $\mu$l transcription reaction, with reagents obtained from Stratagene (La Jolla, Calif.). Hybridizations were performed at 55° C. for 22 hr using approximately 75 $\mu$l or 5×10$^6$ cpm/ml probe per slide. RNAase A digestions were performed in buffer prewarmed to 37° C. The final wash stringency was 0.1×SSC at 60° C. for 35 min. Emulsion-dipped slides were exposed for 2 weeks prior to developing. Slides were counterstained with thionin.

Figure 1B:
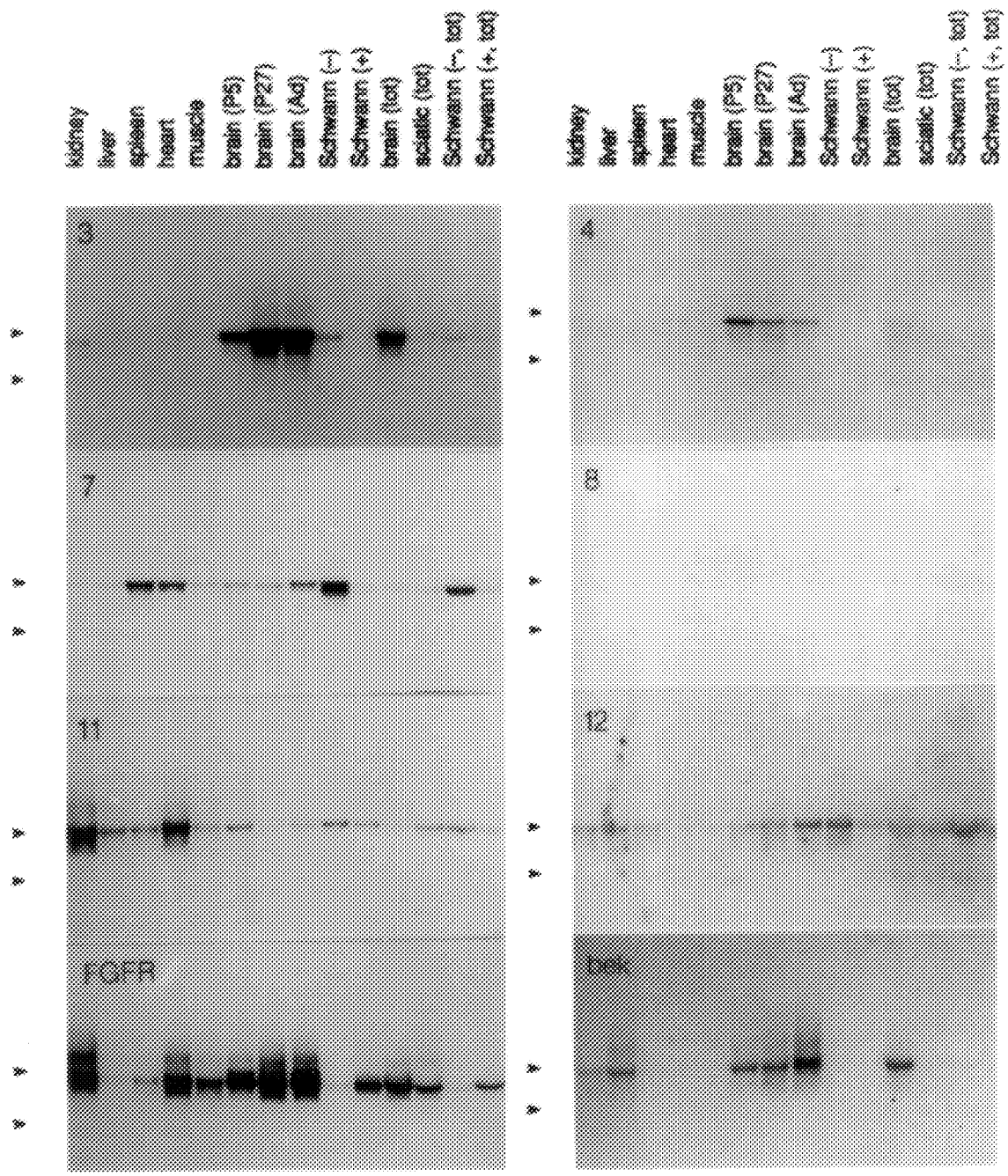

The various tissue expression profiles are shown in FIG. 1. Poly(A) (left 10 lanes) or total RNA (tot, right 4 lanes) from the indicated rat tissues was analyzed for expression of PTK mRNAs. All tissues were taken from animals 27 days postnatal, except where otherwise indicated. Sciatic nerves (sciatic) were obtained from 7-to-8-day-old rats. Rat Schwann cells were cultured in either the presence (+) or absence (−) of 20 μM forskolin for 48 hr prior to harvesting. All lanes contain either 2.5 μg of poly(A)$^+$ RNA or 10 μg of total RNA, except for the cultured Schwann cell poly(A)$^+$ lanes, which contain 1.0 μg each. The relative migration of 18S and 28S ribosomal RNAs, as determined by methylene blue staining, is indicated by the arrowheads. Filters 1–13 show hybridization with $^{32}$P radiolabeled cDNA probes to tyro-1 through tyro-13. Also shown for comparison is the hybridization observed using isolates of elk, the bFGF receptor (FGFR), and the bek FGF receptor. Exposure times were as follows: 34 hr (1, 5, 6, 7, 11), 41 hr (3, 4, FGFR), 120 hr (2, 9, 10, bek), 158 hr (8, 13, elk), 8 days (12).

The results of this analysis (FIG. 1) demonstrate that 6 of the 11 novel kinase genes (tyro-1 through tyro-6), together with the elk gene, are preferentially expressed by cells of the nervous system. For example, tyro-1, a novel member of the eck kinase subfamily, exhibited strong hybridization to brain mRNA, a faint signal in Schwann cells, and very faint signals in kidney and heart. Tyro-4 also a novel member of the eck subfamily, exhibited more modest hybridization to two mRNAs in postnatal day 5(P5) brain, with lower signals evident in older brains as well as kidney and heart. The novel EGF receptor homolog tyro-2 identified a high molecular weight mRNA in brain that could also be detected in kidney and heart. It is possible that the very low tyro-1, tyro-2, and tyro-4 hybridization signals observed in kidney and heart are due to neural contamination from the adrenal gland and cardiac ganglia, respectively. Tyro-3, a member of the novel kinase subfamily with similarity to the insulin receptor, showed intense hybridization to brain mRNA, with very faint signals in perhaps all other tissues.

Members of the same receptor-configured kinase subfamily occasionally exhibited very different patterns of expression. Within the elk subfamily, for example, elk itself and the related kinases tyro-5 and tyro-6 were exclusively or predominantly expressed in neural tissues, elk strongly hybridized to two mRNA species in brain and Schwann cells, tyro-5 exhibited strong hybridization to P5 brain mRNA with reduced signals present in later stage brains and in Schwann cells, and tyro-6 gave a strong hybridization signal in cultured Schwann cells, weaker signals in brain, and very faint but detectable signals in other tissues. In contrast, expression of the elk-related kinase tyro-11 was predominant in heart and kidney, but expressed at lower levels in neural tissue. The distinct hybridization patterns observed between members of this closely related subfamily indicate that despite significant similarity at the nucleotide level, cross-hybridization is not readily detected when hybridizations are carried out at high stringency. Tyro-5 and tyro-6, the most closely related of the PTK domains we analyzed, exhibit 84.2% nucleotide identity over the kinase domain, but their hybridization profiles can be readily distinguished (FIG. 1, compare profiles 5 and 6).

Among those kinases not restricted to neural cells, tyro-9, a member of the FGF receptor subfamily, exhibited a pattern of expression that was distinct from that of either the bFGF receptor or bek. Most strongly expressed in kidney and liver, it exhibited only weak hybridization signals with brain mRNA. At two extremes of expression, tyro-12 yielded weak hybridization signals in all tissues, with expression being somewhat lower in heart and muscle, but tyro-8 (distantly related to Dsrc28) yielded only an extremely faint signal in spleen and heart.

Schwann cell expression of certain kinase genes was strongly regulated by cAMP (FIG. 1). As for the PDGF receptor gene (Weinmaster and Lemke, *EMBO J.*, 9:915–920, 1990), expression of the elk and FGF receptor genes was significantly up-regulated by 48 hr treatment with forskolin. Since cAMP induction of the PDGF receptor appears to account for the synergistic effect on Schwann cell proliferation achieved with combined application of PDGF and forskolin (Weinmaster and Lemke, *EMBO J.*, 9:915–920, 1990), cAMP induction of the FGF receptor may also explain the similar synergistic effect observed for the combination of FGF and forskolin (Davis and Stroobant, *J. Cell Biol.*, 110:1353–1360, 1990). Importantly, cAMP induction was not observed for most of the receptor PTKs expressed by Schwann cells; the tyro-1, tyro-3, tyro-6, tyro-7, tyro-12, and tyro-13 mRNAs were down-regulated in the presence of forskolin, and expression of the tyro-5 and tyro-11 genes was not affected by the drug.

Several receptor PTKs exhibited relatively modest signals in sciatic nerve compared with cultured Schwann cells or other tissues. This is probably a function of both the cellular heterogeneity of the nerve, which contains a substantial number of fibroblasts and endothelial cells, and the great sensitivity of PCR amplification.

EXAMPLE 4

DEVELOPMENTAL EXPRESSION PROFILE OF NEURAL PTK mRNAs

Figure 2:
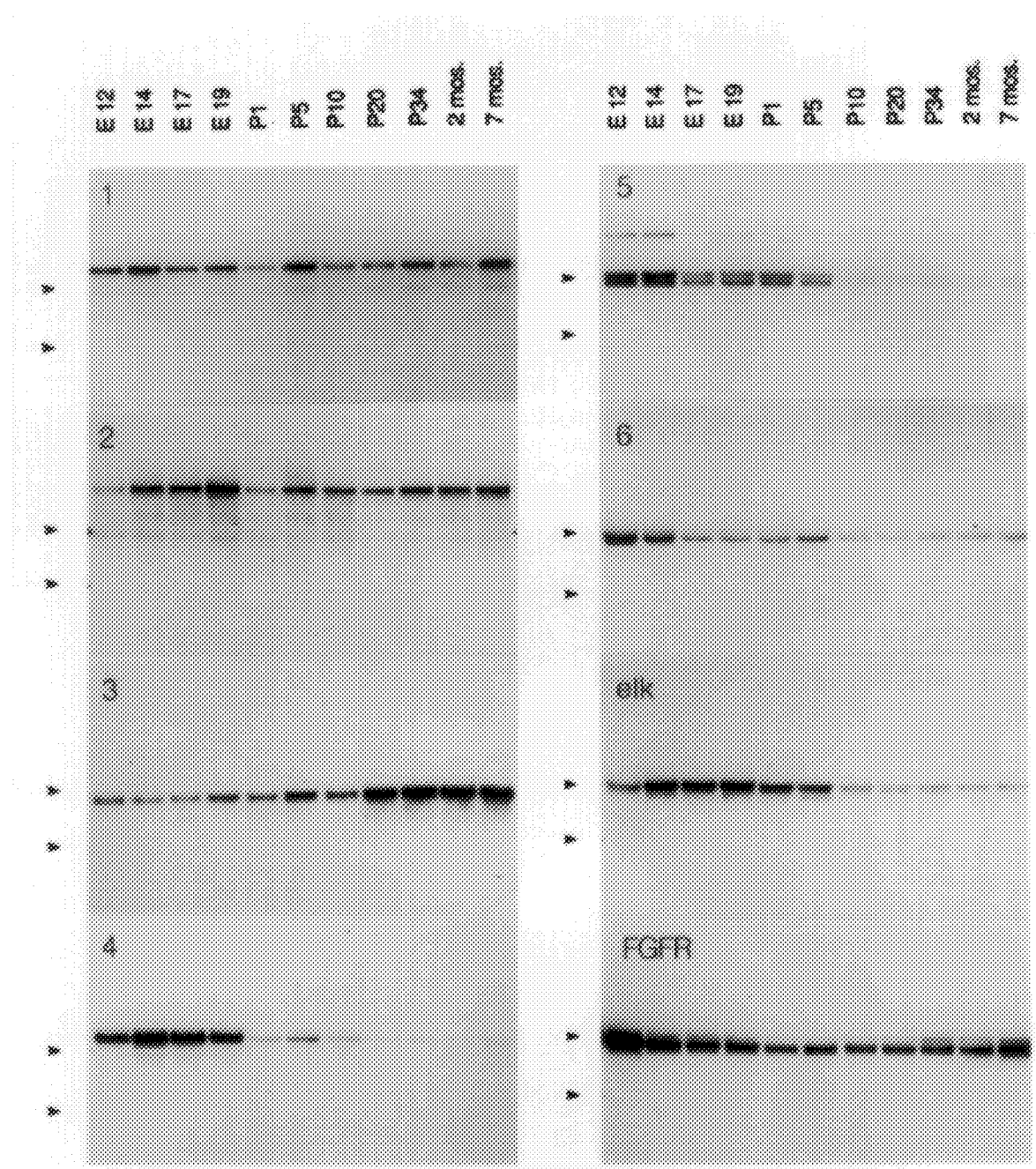
FIG. 2 shows the developmental tissue profiles of the novel PTK mRNAs which were predominantly or exclusively neural in their distribution.

Since many of the determinative events in mammalian neural development occur near the midpoint of embryogenesis, a study was performed to determine whether any of the novel neural kinase genes were expressed embryonically. To assess their developmental expression, a set of Northern blots containing mRNA isolated from the brains of rats ranging in age from embryonic day 12 (E12) to adult were probed. For comparison, included were the bFGF receptor and elk in this survey, the results of which are presented in FIG. 2. For each of the novel kinase genes, expression was observed in the developing central nervous system at E12, a time at which multiple influences on both neural cell proliferation and differentiation are known to be exercised.

Poly(A)$^+$ RNA (2 μg) from rat brains obtained from animals of the indicated ages (E12 to 7 months postnatal) was analyzed for the expression of PTK mRNAs. Filters 1–6 show hybridization obtained with $^{32}$P-radiolabled cDNA probes to tyro-1 through tyro-6. Also shown are the hybridization profiles obtained using isolates of elk and the bFGF receptor (FGFR). The relative migration of 18S and 28S ribosomal RNAs, as determined by methylene blue staining, is indicated by the arrowheads. Exposure times are as follows: 15 hr (1, 3, 5, elk, FGFR), 22 hr (4, 6), 50 hr (2).

Although detected in adult brain, three of the novel kinase genes were maximally expressed embryonically. mRNA encoding the e/k-related kinase tyro-6, for example, was most abundantly expressed at E12; expression gradually fell until P10 and was relatively constant thereafter. Similarly, mRNA encoding the closely related kinase tyro-5 was maximally expressed at E14; expression fell sharply after P5 to a much lower steady-state level in the adult brain. The gene encoding the eck- related kinase tyro-4 exhibited a similar, though even more dramatic regulation, with a peak in expression at E14/17, a sharp drop at birth, and a low steady-state level after P10.

In contrast to the pronounced drop in expression for tyro-4 and tyro-5, expression of mRNA encoding the eck-like kinase tyro-1, while exhibiting some temporal fluctuation, was relatively constant throughout neural development. A similar, though less variable-developmental profile, was observed for mRNA encoding the bFGF receptor. Although maximal expression was observed at E12, bFGF receptor mRNA levels fell only modestly during the course of brain development and remained high in adult animals. Of the novel kinase genes analyzed in FIG. 2, only tyro-3 exhibited a significant increase in expression during late neural development, with appreciably higher mRNA levels (relative to E12) evident after P20.

EXAMPLE 5

IN SITU LOCALIZATION OF NOVEL PTK TRANSCRIPTS IN BRAIN

To determine whether any of the novel neural kinases exhibited cell type-restricted expression in the vertebrate central nervous system, radiolabeled antisense RNA probes for each of the clones were prepared and these probes hybridized in situ to 30 μm brain sections prepared from 33-day-old and adult male rats. For comparison, antisense probes prepared from our isolates of the bFGF receptor and the related FGF receptor bek were included.

Although the profiles of these brain sections represented a selective sampling of the brain, they nonetheless demonstrated that expression of each of the novel neural kinases is highly regionalized. Tyro-1 mRNA was the most widely expressed in adult brain. Tyro-1 probes exhibited exceptionally strong and continuous hybridization in all fields of the hippocampus and the dentate gyrus and throughout the neocortex, with a diffuse band present in layer 3. Strong hybridization was also seen in the Purkinje cell layer, the inferior olive, and lateral nucleus of the cerebellum, but not in the cerebellar granule cell layers.

In contrast, the tryo-2 gene exhibited a much more restricted pattern of expression. Hybridization was again evident throughout all fields of the hippocampus and the dentate gyrus, but signals were restricted to occasional (~1 in 10) cells. This striking, punctate pattern of hippocampal hybridization was not seen for any other PTK gene. A similarly restricted pattern of tyro-2 hybridization was also observed throughout the neocortex. Stronger and more continuous hybridization was evident in the medial habenula and in the reticular nucleus of the thalamus, but in contrast to tyro-1, no signal above background was observed in the remainder of the thalamus. The strongest tyro-2 hybridization signal in the brain was observed in an intercalated nucleus of the amygdala. No signal was evident in the Purkinje cell layer in the cerebellum. The hybridization pattern have observed for tyro-2 is largely consistent with its expression by a subset of 7-amino-n-butyric acid (GABA)-ergic neurons.

In situ hybridization signals corresponding to tyro-3 mRNA presented an equally striking pattern. In the hippocampus, strong hybridization was observed in the CA1 field. However, upon crossing the border from CA1 to the shorter CA2 field an abrupt drop in the tyro-3 hybridization signal was observed. The tyro-3 signal remained much reduced in CA3 (relative to CA1), and no signal at all in the dentate gyrus was observed. Tyro-3 therefore provides an excellent molecular marker for the CA1/CA2 transition, previously defined on the basis of hippocampal cell size and circuitry. Robust tyro-3 hybridization was also evident in large cells throughout neocortex, with the strongest signals being observed in deeper layers. In the cerebellum, strong hybridization was observed to granule cells, but not to Purkinje cells, a pattern that was the opposite of that observed for tyro-1.

Consistent with their developmental expression profiles, tyro-4, tyro-5, and tyro-6 exhibited the most restricted patterns of expression in adult brain. Distinct hybridization to tyro-4 was evident in the facial nucleus of the pons, with more modest signals present in the bed nucleus of the anterior commissure and the triangular nucleus of the septum. The tyro-5 gene was expressed weakly in cortex, at a modest level in all fields of the hippocampus, and in a subset of Purkinje cells in the cerebellum. The tyro-6 gene showed a similar pattern of expression, giving a signal in Purkinje cells and weak signals in the hippocampus.

The two FGF receptor genes examined, those encoding the bFGF receptor and bek, exhibited very different patterns of expression in the brain. mRNA encoding the bFGF receptor was expressed at high levels in hippocampal neurons, but exhibited a field distribution that was nearly the inverse of tyro-3., i.e., expression was reduced in CA1 relative to CA2 and CA3. mRNA levels in the dentate gyrus were lowest of all. The expression of bFGF receptor mRNA in the choroid plexus and in the central nucleus of the amygdala and in a narrow band of cells in layer 6 of neocortex, a region not seen in the previous work of Wanaka, et al. (*Neuron*, 5:267–281, 1990) was also observed. In contrast, expression of bek mRNA was largely confined to non-neuronal cells. High level expression was observed in the choroid plexus, and in the white matter glia of the cerebellum and the pons. Diffusely localized hybridization to a layer of cells that may be Bergmann glia was also apparent in the cerebellum. The cerebellar expression pattern of bek was clearly distinct from the patterns observed for tyro-5 and tyro-6, which marked Purkinje cells, but exhibited no hybridization to white matter glia.

TABLE 2

(SEQ ID NOS: 36–54)

| KINASE SUB-FAMILY | | DEDUCED AMINO ACID SEQUENCES FOR PUTATIVE TYROSINE KINASES | | | | | |
|---|---|---|---|---|---|---|---|
| | | VI | VII | | VIII | IX | INCIDENCE |
| abl | abl | NCLVGENN | LVKVADFGLSRLMTGDTYTAN | | AGAKFPIKWTAPESL | NYNKPSIKS | 6 |
| | arg | NCLVGENN | VVKVADFGLSRLMTGDTYTAN | | AGAKFPIKWTAPESL | NYNTPSIKS | 3 |
| | fos/fps' | NCLVTEKN | VLKISDFGHSREEADGVYAASG | | GLRQVPVKWTAPEAL | NYGRYSSES | |
| | for | NCLVGENN | TLKISDFGMSRQEDGGVYSSS | | GLKQIPIKWTAPEAL | NYGRYSSES | 2 |
| src | Dsrc28' | NCLVGSEN | VVKVADFGLARYVLDDQYTSSG | | GTKFPIKWAPPEVL | NYTRFSSKS | |
| | tyro-8 | NCLVDSDL | SVKVSDFGMTRYVLDDQYVSSV | | GTKFPVKWSAPEVF | NYFKTSSKS | 2 |

TABLE 2-continued (SEQ ID NOS: 36–54)

| KINASE SUB-FAMILY | | DEDUCED AMINO ACID SEQUENCES FOR PUTATIVE TYROSINE KINASES | | | | INCIDENCE |
|---|---|---|---|---|---|---|
| | | VI | VII | VIII | IX | |
| tyro-13 | tyro-13 | NVLVSEDN | VAKVSDFGLTKEASSTQ | DTGKLPVKWTAPEAL | REKKFSTKS | 11 |
| eph/ack/alk | eph' | NILVNQNL | CCKVSDFGLTRLL DDFDGTYET | QGGKIPIRWTAPEAI | AHRIFTTAS | |
| | ack | NILVNSNL | VCKVSDFGLSRVLEDDPEATYTT | SGGKIPIRWTAPEAI | SYRKFTSAS | 5 |
| | tyro-1 | NILVNSNL | VCKVSDFGHSRVLEDDPEAAYTT | RGGKIPIRWTAPEAI | AYRKFTSAS | 1 |
| | tyro-1 | NILINSNL | VCKVSDFGLSRVLEDDPEAAYTT | RGGKIPIRWTSPEAI | AYRKFTSAS | 4 |
| | alk | NILVNSNL | VCKVSDFGLSRYLQDDTSDPTYSS | LGGKIPVRWTAPEAI | AYRKFTSAS | 1 |
| | tyro-5 | NILVNSNL | VCKVSDFGLSRFLEDDTSDPTYTSA | LGGKIPIRWTAPEAI | QYRKFTSAS | (3) |
| | tyro-6 | NILVNSNL | VCKVSDFGLSRFLEDDPSDPTYTSS | LGGKIPIRWTAPEAI | AYRKFTSAS | 3 |
| | tyro-11 | NILVNSNL | VCKVSDFGLSRFLEENSSDPTYTSS | LGGKIPIRWTAPEAI | AFRKFTSAS | (1) |
| EGF-R | EGF-R | NVLVKTPQ | IIVKITDFGLAKLLGAEEKEYNA | EGGKVPIKWMALESI | LNRIYTNQS | 3 |
| | nou | NVLVKSPN | IIVKITDFGLARLLDIDETEYNA | DGGKVPIKWMALESI | LRRRFTNQS | 10 |
| | tyro-2 | NVLVKSPN | IIVKITDFGLARLLEGDEKEYNA | DGGKMPIKHMALECI | NYRKFTNQS | 8 |
| FGF-R | bFGF-R | NVLVTEDN | VMKIADFGLARDINNIDYYKKT | TNGRLPVKWMAPEAL | FDRIYTNQS | 4 |
| | bak | NVLVTENN | VMKIADFGLARDINNIDYYKKT | INGRLPVKWMAPEAL | FDRVYTNQS | 2 |
| | tyro-9 | NVLVTEDD | VMKIADFGLARGVNNIDYYKKT | SNGRLPVKWMAPEAL | FDRVYTNQS | 1 |
| PDGF-R | PDGF-A R | NVLLAQGK | IVKICDFGLARDIMNDSNYVSK | GSTFLPVKWMAPESI | FDNLYTTLS | 3 |
| | PDGF-B R | NMLICEGK | LVKICDFGLARDIMRDSNYISK | GSTFLPLKWMAPESI | FNSLYTTLS | 1 |
| | CSF-1 R | NVLLTSGN | VAKIGDFGLARDIMNDSNYVVK | GNARLPVKWMAPESI | FDCVYTVQS | 20 |
| | flt | NILLSENN | VVKICDGFLARDIYKNPDYVRR | GDTRLPLKWMAPESI | FDKVYSTKS | 5 |
| tyro-3 | tyro-3 | NCMLAEDM | TVCVADFGLSRKIYSGDYYRQG | CASKLPVKHLALESL | ADNLYTVNS | 3 |
| | tyro-7 | NCMLNENM | SVCVADFGLSKKIYNGDYYRQG | PFAKMPVKWIAIESL | ADRVYTSKS | 4 |
| | tyro-12 | NCMLRDDM | TVCVADFGLSKKIYSGDYYRQG | RIAKMPVKWIAIESI | ADRVTYSKS | (3) |
| Insulin-R | trk' | NCLVGQGL | VVKIGDFGMSRDITSTDYYRVG | GRTMLPIRWMPPESI | LYRKFTTES | |
| | trkB' | NCLVGENL | LVKIGDFGMSRDVYSTDYYRVG | GHTMLPIRWMPPESI | MYRKFTTES | |
| | IGRIR | NCMVAEDF | TVKIGDFGMTRDIYETDYYRKG | GKGLLPVRWMSPESL | KDGVFTTNS | 2 |
| | tyro-10 | NCLVGKNY | TIKIADFGMSRNLYSGDYYRYQ | GRAVLPIRWMSWESI | LLGKFTTAS | (6) |

We claim:

1. An isolated polynucleotide selected from the group consisting of Sequence ID Nos. 1, 3, 5, 7, 9, 11, 15, 19, 21 and 23 and degenerate variants thereof, wherein said polynucleotide(s) encodes protein(s) having a tyrosine kinase domain and a tissue expression pattern of a receptor protein-tyrosine kinase subtype selected from tyro-1, tyro-2, tyro-3, tyro-4, tyro-5, tyro-6, tyro-8, tyro-10, tyro-11, and tyro-12, respectively.

2. The polynucleotide of claim 1 which is DNA.

3. The polynucleotide of claim 1 which is RNA.

4. Isolated and purified oocytes capable of expressing the RNA of claim 3.

5. A recombinant expression vector containing the polynucleotide of claim 1.

6. The vector of claim 5 which is incorporated in a carrier system.

7. A isolated host cell containing the expression vector of claim 5.

8. A method for identifying polynucleic acid encoding a protein having a tyrosine kinase domain and a tissue expression pattern a receptor protein-tyrosine kinase subtype selected from the group consisting of tyro-1, tyro-2, tyro-3, tyro-4, tyro-5, tyro-6, tyro-8, tyro-10, tyro-11, and tyro-12, the method comprising:

(a) contacting said polynucleic acid with an isolated polynucleotide according to claim 5, wherein the contacting is carried out under stringent hybridization conditions, and (b) identifying polynucleic acid which hybridizes to said isolated polynucleotide, wherein hybridization of said polynucleic acid to said polynucleotide is indicative of a polynucleic acid encoding a protein having a tyrosine kinase domain.

9. An isolated polynucleic acid selected from the group consisting of Sequence ID Nos. 1, 3, 5, 7, 9, 11, 15, 19, 21, and 23 and sequences fully complementary thereto.

10. An isolated polynucleotide encoding a protein having an amino acid sequence selected from the group consisting of Sequence ID Nos. 2, 4, 6, 8, 10, 12, 16, 20, 22 and 24.

* * * * *